US008664226B2

(12) United States Patent
Miura et al.

(10) Patent No.: US 8,664,226 B2
(45) Date of Patent: Mar. 4, 2014

(54) COMPOUND HAVING 3-HETEROARYLPYRIMIDIN-4-(3H)-ONE STRUCTURE AND PHARMACEUTICAL PREPARATION CONTAINING SAME

(75) Inventors: Toru Miura, Higashimurayama (JP); Kazuhiro Onogi, Higashimurayama (JP); Seiichi Sato, Higashimurayama (JP); Junya Tagashira, Higashimurayama (JP); Gen Watanabe, Higashimurayama (JP); Ryohei Sekimoto, Higashimurayama (JP); Rie Ishida, Higashimurayama (JP); Hitomi Aoki, Higashimurayama (JP); Tadaaki Ohgiya, Higashimurayama (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 214 days.

(21) Appl. No.: 13/263,023

(22) PCT Filed: Apr. 16, 2010

(86) PCT No.: PCT/JP2010/002766
§ 371 (c)(1),
(2), (4) Date: Oct. 5, 2011

(87) PCT Pub. No.: WO2010/119700
PCT Pub. Date: Oct. 21, 2010

(65) Prior Publication Data
US 2012/0028983 A1  Feb. 2, 2012

(30) Foreign Application Priority Data

Apr. 17, 2009  (JP) ................................. 2009-101347

(51) Int. Cl.
*C07D 401/14* (2006.01)
*A61K 31/506* (2006.01)

(52) U.S. Cl.
USPC ...... 514/255.05; 514/269; 544/295; 544/296; 544/319

(58) Field of Classification Search
USPC .............. 544/295, 296, 319; 514/255.05, 269
See application file for complete search history.

(56) References Cited

U.S. PATENT DOCUMENTS 5,565,464 A  10/1996  Salimbeni et al.

FOREIGN PATENT DOCUMENTS

| JP | 4-230370 A | 8/1992 |
| JP | 5-505609 A | 8/1993 |
| JP | 6-199811 A | 7/1994 |
| JP | 6-509349 A | 10/1994 |
| WO | 95/22543 A1 | 8/1995 |
| WO | 2008/062905 A2 | 5/2008 |
| WO | 2008/084303 A1 | 7/2008 |
| WO | 20081084303 A1 | 7/2008 |
| WO | 2008/096820 A1 | 8/2008 |
| WO | 2008/096829 A1 | 8/2008 |
| WO | 20081096820 A1 | 8/2008 |
| WO | 20081096829 A1 | 8/2008 |
| WO | 2008/143262 A1 | 11/2008 |

OTHER PUBLICATIONS

Fayer et al., PubMed Abstract (J Clin Pharmacol. 41(3):305-16), 2001.*
Schupp, M. et al., "Angiotensin Type 1 Receptor Blockers Induce Peroxisome Proliferator-Activated Receptor-g Activity", Circulation, May 2004, pp. 2054-2057, cited in spec.
Notification of Transmittal of Copies of Translation of the International Preliminary Report on Patentability (form PCT/IB/338) of International Application No. PCT/JP2010/002766, mailed Dec. 1, 2011, with Forms PCT/IB373, PCT/IB/326, and PCT/ISA/237.
Nicolaie, E. et al., "Synthesis and angiotensin II receptor antagonist activity of C-linked pyrimidine derivatives", Eur. J. Med. Chem., 1995, vol. 30, pp. 365-375, cited in ISR.
Benson, S. C. et al., "Identification of Telmisartan as a Unique Angiotensin II Receptor Antagonist With Selective PPARg-Modulating Activity", Hypertension, May 2004, vol. 43, pp. 993-1002, cited in spec.
Gross, B. et al., "PPAR agonists: multimodal drugs for the treatment of type-2 diabetes", Best Practice & Research Clinical Endocrinology & Metabolism, 2007, vol. 21, pp. 687-710, cited in spec.
Nesto, R. W. et al., "Thiazolidinedione Use, Fluid Retention, and Congestive Heart Failure: A Consensus Statement from the American Heart Association and American Diabetes Association", Circulation: Journal of the AHA, Dec. 2003, vol. 108, pp. 2941-2948, cited in spec.
Patel, CH. et al., "Thiazolidinediones, peripheral oedama, and congesitve heart failure: what is the evidence?", Diabetes and Vascular Disease Research, May 2005, vol. 2, pp. 61-66, cited in spec.
Pa, S. et al., "Protection of the kidney by thiazolidinediones: An assessment from bench to bedside", Kidney International, 2006, vol. 70, pp. 1223-1233, cited in spec.
Schmieder, R. E. et al., "Mechanisms for the Clinical Benefits of Angiotensin II Receptor Blockers", American Journal of Hypertension, 2005, vol. 18, pp. 720-730, cited in spec.
Schupp, M. et al., "Angiotensin Type 1 Receptor Blockers Induce Peroxisome Proliferator-Activated Receptor-g Activity", Circulation, May 2004, vol. 109, pp. 2054-2057, cited in spec.

(Continued)

*Primary Examiner* — Deepak Rao
(74) *Attorney, Agent, or Firm* — Westerman, Hattori, Daniels & Adrian, LLP

(57) ABSTRACT

Disclosed is a compound which has both an angiotensin-II receptor antagonistic activity and a PPARγ activation activity and is useful as a prophylactic and/or therapeutic agent for hypertension, heart diseases, angina pectoris, cerebrovascular disorders, cerebral circulatory disorders, ischemic peripheral circulatory disorders, renal diseases, arteriosclerosis, inflammatory diseases, type-2 diabetes, diabetic complications, insulin resistance syndrome, syndrome X, metabolic syndrome and hyperinsulinemia. [In the formula, A represents a 5- to 10-membered heteroaryl group; $R^1$ and $R^2$ independently represent a $C_{1-6}$ alkyl group; and each of $R^3$ to $R^5$ is absent or represents H, a halogen atom, OH, $NO_2$, a halo-$C_{1-6}$ alkyl group, a (substituted) $C_{1-6}$ alkoxy group, a (substituted) $C_{3-6}$ cycloalkyloxy group, or a 5- to 10-membered heteroaryl group.]

5 Claims, 1 Drawing Sheet

(56) References Cited

OTHER PUBLICATIONS

Semple, R. K. et al., "PPARg and human metabolic disease", The Journal of Clinical Investigation, Mar. 2006, vol. 116, pp. 581-589, cited in spec.

Siragy, H. M. "Evidence for Benefits of Angiotensin Receptor Blockade Beyond Blood Pressure Control", Antihypertensive Agents: Mechanisms of Drug Action, 2008, pp. 261-267, cited in spec.

The Shiga Microalbuminuria Recuction Trial Group, "Reduction of Microalbuminuria in Patients with Type 2 Diabetes", Diabetes Care, Jun. 2007, vol. 30, pp. 1581-1583, cited in spec.

Sotiropoulos, K. B. et al., "Adipose-specific effect of rosiglitazone on vascular permeability and proteine kinase C activation: novel mechanism for PPARg agonist's effects on edema and weight gain", The FASEB Journal, Jun. 2006, vol. 20, pp. E367-E380, cited in spec.

Walcher, D. et al., "Insulin resistance and cardiovascular disease: the role of PPARg activators beyond their anti-diabetic action", Diabetes and Vascular Disease Research, Oct. 2004, vol. 1, pp. 76-81, cited in spec.

International Search Report of PCT/JP2010/002766, mailing date May 25, 2010.

* cited by examiner

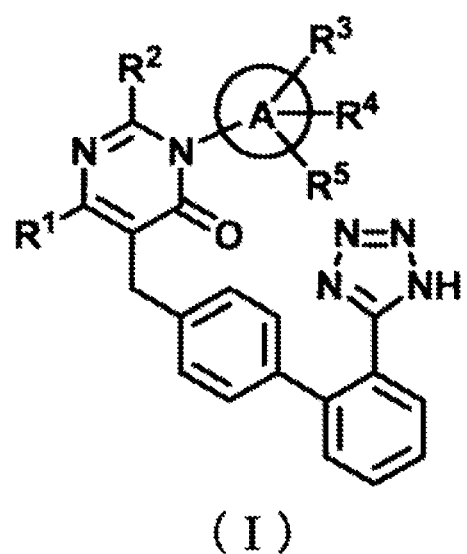
(I)

COMPOUND HAVING 3-HETEROARYLPYRIMIDIN-4-(3H)-ONE STRUCTURE AND PHARMACEUTICAL PREPARATION CONTAINING SAME

TECHNICAL FIELD

The present invention relates to a novel compound having a structure of 3-heteroarylpyrimidin-4-(3H)-one which has both angiotensin II antagonistic activity and PPARγ activation activity, and a pharmaceutical preparation containing the same.

BACKGROUND ART

In recent years, disorders like diabetes, hypertension, dyslipidemia and obesity which can be a risk factor for arteriosclerotic disorders have been rapidly increasing due to changes in life style with improvements in living standard, i.e., high calorie and high cholesterol type diet, obesity, lack of exercise, aging, and the like. It is known that, although being a risk factor independent of each other, overlap of the disorders can cause an occurrence of arteriosclerotic disorders at higher frequency or aggravation of the disorders. As such, with the understanding of a condition having a plurality of risk factors for arteriosclerotic disorders as metabolic syndrome, efforts have been made to elucidate the cause of the syndrome and to develop a therapeutic method therefor.

Angiotensin II (herein below, it may be also abbreviated as AII) is a peptide that is found to be an intrinsic pressor substance produced by renin-angiotensin system (i.e., RA system). It is believed that pharmacological inhibition of angiotensin II activity can lead to treatment or prevention of circulatory disorders like hypertension. Accordingly, an inhibitor for angiotensin converting enzyme (ACE) which inhibits the enzyme promoting the conversion of angiotensin I (AI) to angiotensin II (AII) has been clinically used as an inhibitory agent for RA system. Furthermore, an orally administrable AII receptor blocker (Angiotensin Receptor Blocker: ARB) has been developed, and losartan, candesartan, telmisartan, valsartan, olmesartan, and irbesartan are already clinically used as a hypotensive agent. It is reported by many clinical or basic studies that, as having not only a hypotensive activity but also other various activities including an anti-inflammatory activity, an endothelial function improving activity, a cardiovascular remodeling inhibiting activity, an oxidation stress inhibiting activity, a proliferation factor inhibiting activity, and insulin resistance improving activity, ARB is useful for cardiovascular disorders, renal diseases, and arteriosclerosis, etc. (Non-Patent Document 1 and 2). Most recently, it is also reported that ARB particularly has a kidney protecting activity which does not depend on a hypotensive activity (Non-Patent Document 3).

Meanwhile, three isoforms, i.e., α, γ, and δ, are identified so far as peroxisome proliferaor-activated receptors (PPARs) which belong to a nuclear receptor superfamily. Among them, PPARγ is an isoform that is most abundantly expressed in an adipose tissue and it plays an important role in differentiation of adipocytes or metabolism of glycolipids. Currently, thiazolidinedione derivatives (i.e., TZD) like pioglitazone or rosiglitazone are clinically used as a therapeutic agent for diabetes having PPARγ activation activity, and they are known to have an activity of improving insulin resistance, glucose tolerance, and lipid metabolism, etc. Further, it is recently reported that, based on activation of PPARγ, TZD exhibits various activities including a hypotensive activity, an anti-inflammatory activity, an endothelial function improving activity, a proliferation factor inhibiting activity, and an activity of interfering RA system, etc. It is also reported that, according to such multiple activities, TZD shows a kidney protecting activity particularly in diabetic nephropathy without depending on blood sugar control (Non-Patent Document 4, 5, 6, 7, and 8). Meanwhile, there is also a concern regarding adverse effects of TZD caused by PPARγ activation like body fluid accumulation, body weight gain, peripheral edema, and pulmonary edema (Non-Patent Document 9 and 10).

It has been recently reported that telmisartan has a PPARγ activation activity (Non-Patent Document 11). It has been also reported that the irbesartan has the same activity (Non-Patent Document 12). These compounds have both a RA system inhibiting activity and a PPARγ activation activity, and thus are expected to be used as an integrated agent for prevention and/or treatment of circulatory disorders (e.g., hypertension, heart disease, angina pectoris, cerebrovascular disorders, cerebral circulatory disorders, ischemic peripheral circulatory disorders, and renal diseases, etc.) or diabetes-related disorders (e.g., type 2 diabetes, diabetic complications, insulin resistant syndrome, metabolic syndrome, and hyperinsulinemia, etc.) without increasing a risk of body fluid accumulation, body weight gain, peripheral edema, pulmonary edema, or congestive heart failure that are concerned over the use of TZD (Patent Document 1). Among them, for diabetic nephropathy, a synergistic prophylactic and/or therapeutic effect is expected from multiple kidney protecting activity based on activities of RA system inhibition and PPARγ activation.

As a compound having the activities above, the pyrimidine and triazine derivatives (Patent Document 1), imidazopyridine derivatives (Patent Document 2), indole derivatives (Patent Document 3), and imidazole derivatives (Patent Document 4) have been reported. Of these, a group of compounds that are characterized by having an oxadiazolidinone ring or a thiadiazolidinone ring on biphenyl ring is described in Patent Document 1, and a compound having the pyrimidinone skeleton like the following formula (A) is disclosed (see, Example 219 of Patent Document 1):

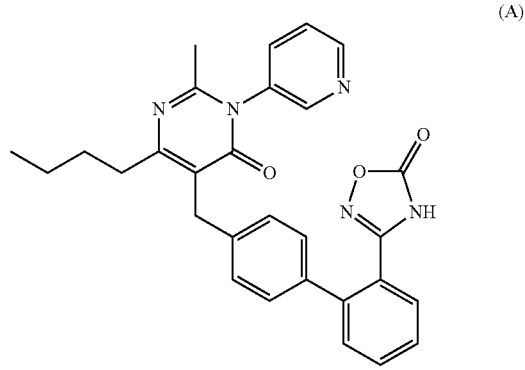 [SMILES: CCCCc1nc(C)n(-c2cccnc2)c(=O)c1Cc1ccc(-c2ccccc2-c2noc(=O)[nH]2)cc1]

(A)

However, according to the group of compounds described in Patent Document 1, no tetrazolyl group is present on the biphenyl ring.

The compounds represented by the following formula (B) which have angiotensin II antagonistic activity and are useful for treatment of hypertension, heart failure, intraocular hypertension, etc. have been reported (Patent Document 5):

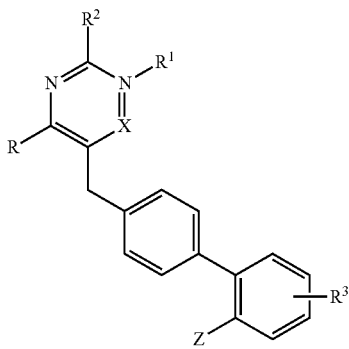

(B)

[in the formula, R represents $C_{1-4}$ alkyl, $R^1$ represents a hydrogen, $C_{1-4}$ alkyl, aryl, or aryl alkyl (herein, aryl represents phenyl, naphthyl, 2-thienyl, or 2-furanyl) and the like, $R^2$ represents $C_{1-4}$ alkyl and the like, $R^3$ represents a hydrogen and the like, X represents CO and the like, and Z represents carboxyl or tetrazolyl and the like]. However, in the document, a compound in which a heteroaryl group like thienyl group or furanyl group is directly bonded to $R^1$ is not specifically described. Further, with respect to pharmacological activity, there is no description or suggestion regarding the PPARγ activation activity or treatment of diabetes, obesity, or a metabolic syndrome.

The compounds represented by, the following formula (C) which have angiotensin II antagonistic activity and are useful for treatment of hypertension and heart failure have been reported (Patent Document 6):

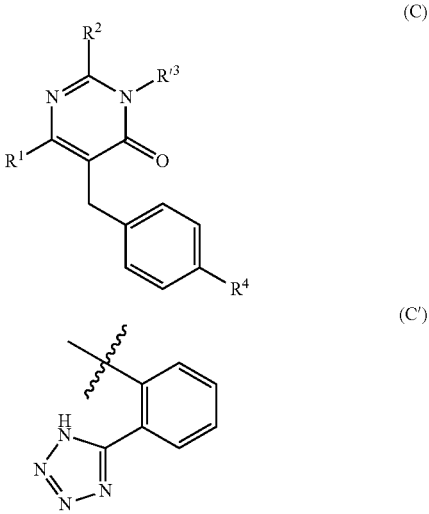

(C)

[in the formula, $R^1$ represents a $C_{1-6}$ alkyl group and the like, $R^2$ represents a hydrogen atom, a halogen atom, a $C_{1-6}$ alkyl group and the like, $R'^3$ represents —$(CH_2)$n-heterocyclic group (herein, n represents an integer of from 0 to 5) and the like, and $R^4$ represents the above formula C' and the like]. However, even in this document, a compound in which a heteroaryl group is directly bonded to $R'^3$ is not specifically described. Further, with respect to pharmacological activity, there is no description or suggestion regarding the PPARγ activation or treatment of diabetes, obesity, or a metabolic syndrome.

PRIOR ART LITERATURE

Patent Document

Patent Document 1: WO 2008/062905
Patent Document 2: WO 2008/084303
Patent Document 3: WO 2008/096820
Patent Document 4: WO 2008/096829
Patent Document 5: Japanese Patent Application National Publication (Laid-Open) No. 6-509349
Patent Document 6] Japanese Patent Application Laid-Open (JP-A) No. 4-230370

Non-Patent Document

Non-Patent Document 1: AMER. J. Hypertension, 18, 720 (2005)
Non-Patent Document 2: Current Hypertension Report, 10, 261 (2008)
Non-Patent Document 3: Diabetes Care, 30, 1581 (2007)
Non-Patent Document 4: Kidney Int., 70, 1223 (2006)
Non-Patent Document 5: Circulation, 108, 2941 (2003)
Non-Patent Document 6: Best Pract. Res. Clin. Endocrinol. Metab., 21 (4), 687 (2007)
Non-Patent Document 7: Diab. Vasc. Dis. Res., 1 (2), 76 (2004)
Non-Patent Document 8: Diab. Vasc. Dis. Res., 2 (2), 61 (2005)
Non-Patent Document 9: J. Clin. Invest., 116 (3), 581 (2006)
Non-Patent Document 10: FASEB J., 20 (8), 1203 (2006)
Non-Patent Document 11: Hypertension, 43, 993 (2004)
Non-Patent Document 12: Circulation, 109, 2054 (2004)

SUMMARY OF THE INVENTION

Problems to be Solved by the Invention

Object of the invention is to provide a novel compound that is useful as a pharmaceutical agent for preventing and/or treating hypertension as a circulatory disorder and diabetes as a metabolic disorder.

BRIEF DESCRIPTION OF DRAWING

FIGURE represents 3-heteroarylpyrimidin-4-(3H)-one derivatives of formula (I).

MEANS FOR SOLVING THE PROBLEMS

As a result of intensive studies to achieve the purpose described above, the inventors of the invention found that the 3-heteroarylpyrimidin-4(3H)-one derivative represented by the formula (I) below has both an excellent angiotensin II antagonistic activity and an excellent PPARγ activation activity, and therefore completed the invention.

Specifically, the invention relates to the following inventions.

[1] 3-heteroarylpyrimidin-4(3H)-one derivative represented by the formula (I) below or salt thereof, or solvate thereof:

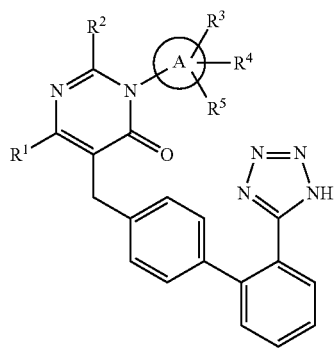

(I)

[in the formula, A represents a 5- to 10-membered heteroaryl group, $R^1$ and $R^2$, which may be the same or different from each other, represent a $C_{1-6}$ alkyl group, $R^3$, $R^4$, and $R^5$ each is independently absent or represents a hydrogen atom, a halogen atom, a $C_{1-6}$ alkyl group, a halo $C_{1-6}$ alkyl group, a $C_{1-6}$ alkoxy group which may have a substituent group, a $C_{3-6}$ cycloalkyloxy group which may have a substituent group, a 5- to 10-membered heteroaryl group, a hydroxyl group, or a nitro group.].

[2] The 3-heteroarylpyrimidin-4(3H)-one derivative described in the above [1] or salt thereof or solvate thereof, in which ring A in the formula (I) is a pyridyl group, a pyrimidinyl group, a pyrazinyl group, a triazinyl group, a thiazolyl group, an isoxazolyl group, a pyrazolyl group, a triazolyl group, a quinolynyl group, an isoquinolynyl group, a benzimidazolyl group, or a benzothiazolyl group.

[3] The 3-heteroarylpyrimidin-4(3H)-one derivative described in the above [1] or [2] or salt thereof, or solvate thereof, in which the substituent group for the $C_{1-6}$ alkoxy group which may have a substituent group in $R^3$, $R^4$ or $R^5$ of the formula (I) is a phenyl group; a hydroxyl group; a $C_{1-6}$ alkylthio group; a $C_{1-6}$ alkylsulfonyl group; an oxazolyl group which may be substituted with a 5- to 10-membered heteroaryl group which may be substituted with a $C_{1-6}$ alkyl group, a $C_{6-10}$ aryl group, or a halogen atom; a pyridyl group which may be substituted with a $C_{1-6}$ alkyl group; a $C_{1-6}$ alkoxycarbonyl group; a carboxyl group; a carbamoyl group which may be substituted with a $C_{1-6}$ alkyl group; a $C_{1-6}$ alkanoylamino group; a $C_{1-6}$ alkylsulfonylamino group; or halo $C_{1-6}$ alkylsulfonylamino group.

[4] The 3-heteroarylpyrimidin-4(3H)-one derivative described in any of the above [1] to [3] or salt thereof, or solvate thereof, in which the substituent group for the $C_{3-6}$ cycloalkyloxy group which may have a substituent group in $R^3$, $R^4$ or $R^5$ of the formula (I) is an oxo group.

[5] The 3-heteroarylpyrimidin-4(3H)-one derivative described in any of the above [1] to [4] or salt thereof, or solvate thereof, in which the compound represented by the formula (I) is a compound selected from a group consisting of:

5-{[2'-(1H-tetrazol-5-yl)biphenyl-4-yl]methyl}-6-butyl-2-methyl-3-(pyridin-2-yl)pyrimidin-4(3H)-one,
5-{[2'-(1H-tetrazol-5-yl)biphenyl-4-yl]methyl}-6-butyl-2-methyl-3-(5-methylpyridin-2-yl)pyrimidin-4(3H)-one,
5-{[2'-(1H-tetrazol-5-yl)biphenyl-4-yl]methyl}-6-butyl-3-(5-methoxypyridin-2-yl)-2-methylpyrimidin-4(3H)-one,
5-{[2'-(1H-tetrazol-5-yl)biphenyl-4-yl]methyl}-6-butyl-3-(3-fluoropyridin-2-yl)-2-methylpyrimidin-4(3H)-one,
5-{[2'-(1H-tetrazol-5-yl)biphenyl-4-yl]methyl}-6-butyl-3-(5-fluoropyridin-2-yl)-2-methylpyrimidin-4(3H)-one,
5-{[2'-(1H-tetrazol-5-yl)biphenyl-4-yl]methyl}-6-butyl-3-(3-chloropyridin-2-yl)-2-methylpyrimidin-4(3H)-one,
5-{[2'-(1H-tetrazol-5-yl)biphenyl-4-yl]methyl}-6-butyl-3-(5-chloropyridin-2-yl)-2-methylpyrimidin-4(3H)-one,
5-{[2'-(1H-tetrazol-5-yl)biphenyl-4-yl]methyl}-3-(6-bromopyridin-2-yl)-6-butyl-2-methylpyrimidin-4(3H)-one,
5-{[2'-(1H-tetrazol-5-yl)biphenyl-4-yl]methyl}-6-butyl-2-methyl-3-[3-(trifluoromethyl)pyridin-2-yl]pyrimidin-4(3H)-one,
5-{[2'-(1H-tetrazol-5-yl)biphenyl-4-yl]methyl}-6-butyl-2-methyl-3-[4-(trifluoromethyl)pyridin-2-yl]pyrimidin-4(3H)-one,
5-{[2'-(1H-tetrazol-5-yl)biphenyl-4-yl]methyl}-6-butyl-2-methyl-3-[5-(trifluoromethyl)pyridin-2-yl]pyrimidin-4(3H)-one,
5-{[2'-(1H-tetrazol-5-yl)biphenyl-4-yl]methyl}-6-butyl-2-methyl-3-[6-(trifluoromethyl)pyridin-2-yl]pyrimidin-4(3H)-one,
5-{[2'-(1H-tetrazol-5-yl)biphenyl-4-yl]methyl}-6-butyl-3-[3-chloro-5-(trifluoromethyl)pyridin-2-yl]-2-methylpyrimidin-4(3H)-one,
5-{[2'-(1H-tetrazol-5-yl)biphenyl-4-yl]methyl}-6-butyl-2-methyl-3-(5-nitropyridin-2-yl)pyrimidin-4(3H)-one,
5-{[2'-(1H-tetrazol-5-yl)biphenyl-4-yl]methyl}-3-[5-(1H-tetrazol-5-yl)pyridin-2-yl]-6-butyl-2-methylpyrimidin-4(3H)-one,
5-{[2'-(1H-tetrazol-5-yl)biphenyl-4-yl]methyl}-3-(5-bromopyrimidin-2-yl)-6-butyl-2-methylpyrimidin-4(3H)-one,
5-{[2'-(1H-tetrazol-5-yl)biphenyl-4-yl]methyl}-6-butyl-2-methyl-3-(pyrimidin-2-yl)pyrimidin-4(3H)-one,
5-{[2'-(1H-tetrazol-5-yl)biphenyl-4-yl]methyl}-6-butyl-3-(5-methoxypyrimidin-2-yl)-2-methylpyrimidin-4(3H)-one,
5-{[2'-(1H-tetrazol-5-yl)biphenyl-4-yl]methyl}-3-[5-(benzyloxy)pyrimidin-2-yl]-6-butyl-2-methylpyrimidin-4(3H)-one,
5-{[2'-(1H-tetrazol-5-yl)biphenyl-4-yl]methyl}-6-butyl-3-(5-hydroxypyrimidin-2-yl)-2-methylpyrimidin-4(3H)-one,
5-{[2'-(1H-tetrazol-5-yl)biphenyl-4-yl]methyl}-6-butyl-3-(5-ethoxypyrimidin-2-yl)-2-methylpyrimidin-4(3H)-one,
5-{[2'-(1H-tetrazol-5-yl)biphenyl-4-yl]methyl}-6-butyl-2-methyl-3-(5-propoxypyrimidin-2-yl)pyrimidin-4(3H)-one,
5-{[2'-(1H-tetrazol-5-yl)biphenyl-4-yl]methyl}-6-butyl-3-(5-isopropoxypyrimidin-2-yl)-2-methylpyrimidin-4(3H)-one,
5-{[2'-(1H-tetrazol-5-yl)biphenyl-4-yl]methyl}-3-(5-butoxypyrimidin-2-yl)-6-butyl-2-methylpyrimidin-4(3H)-one,
5-{[2'-(1H-tetrazol-5-yl)biphenyl-4-yl]methyl}-6-butyl-3-[5-(3-hydroxypropoxy)pyrimidin-2-yl]-2-methylpyrimidin-4(3H)-one,
5-{[2'-(1H-tetrazol-5-yl)biphenyl-4-yl]methyl}-6-butyl-2-methyl-3-{5-[2-(methylthio)ethoxy]pyrimidin-2-yl}pyrimidin-4(3H)-one,
5-{[2'-(1H-tetrazol-5-yl)biphenyl-4-yl]methyl}-6-butyl-2-methyl-3-{5-[2-(methylsulfonyl)ethoxy]pyrimidin-2-yl}pyrimidin-4(3H)-one,
5-{[2'-(1H-tetrazol-5-yl)biphenyl-4-yl]methyl}-6-butyl-3-[5-(cyclohexyloxy)pyrimidin-2-yl]-2-methylpyrimidin-4(3H)-one, 5-{[2'-(1H-tetrazol-5-yl)biphenyl-4-yl]methyl}-6-butyl-2-methyl-3-[5-(4-oxocyclohexyloxy)pyrimidin-2-yl]pyrimidin-4(3H)-one, 5-{[2'-(1H-tetrazol-5-yl)biphenyl-4-yl]methyl}-6-butyl-3-(4,6-dichloropyrimidin-2-yl)-2-methylpyrimidin-4(3H)-one, 5-{[2'-(1H-tetrazol-5-yl)biphenyl-4-yl]methyl}-6-butyl-2-methyl-3-{5-[(5-methyl-2-phenyloxazol-4-yl)methoxy]pyrimidin-2-y}pyrimidin-4(3H)-one, 5-{[2'-(1H-tetrazol-5-yl)biphenyl-4-yl]methyl}-3-{5-{[2-(5-bromofuran-2-yl)-5-methyloxazol-4-yl]methoxy}pyrimidin-2-yl}-6-butyl-2-methylpyrimidin-4(3H)-one, 5-{[2'-(1H-tetrazol-5-yl)biphenyl-4-yl]methyl}-6-butyl-3-{5-{[2-(furan-2-yl)-5-methyloxazol-4-yl]methoxy}pyrimidin-2-yl}-2-methylpyrimidin-4(3H)-one, 5-{[2'-(1H-tetrazol-5-yl)biphenyl-4-yl]methyl}-6-butyl-2-methyl-3-{5-{[5-methyl-2-(naphthalen-2-yl)oxazol-4-yl]methoxy}pyrimidin-2-yl}-pyrimidin-4(3H)-one, 5-{[2'-(1H-tetrazol-5-yl)biphenyl-4-yl]methyl}-6-butyl-2-methyl-3-{5-[2-(5-methyl-2-phenyloxazol-4-yl)ethoxy]pyrimidin-2-yl}pyrimidin-4(3H)-one, 5-{[2'-(1H-tetrazol-5-yl)biphenyl-4-yl]methyl}-6-butyl-3-{5-[2-(5-ethylpyridin-2-yl)ethoxy]pyrimidin-2-yl}-2-methylpyrimidin-4(3H)-one, ethyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetate, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetic acid, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetamide, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylacetamide, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylacetamide, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetic acid, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-3-phenylpropionic acid, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetamide, ethyl 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanoate, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanoic acid, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-methylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-propylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-isopropylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylbutanamide, 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}pentanamide, 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylpentanamide, 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylpentanamide, N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}acetamide, N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}methane sulfonamide, N-{3-{2-{5-{[2 (1H-tetrazol-5-yl)biphenyl-4-yl]methyl}-4-butyl-2-methyl-6-oxopyrimidin-1(6H)-yl}pyrimidin-5-yl oxy}propyl}-1,1,1-trifluoromethane sulfonamide, 5-{[2'-(1H-tetrazol-5-yl)biphenyl-4-yl]-6-butyl-3-(2,6-dimethoxypyrimidin-4-yl)-2-methylpyrimidin-4(3H)-one, 5-{[2'-(1H-tetrazol-5-yl)biphenyl-4-yl]methyl}-6-butyl-2-methyl-3-(pyrazin-2-yl)pyrimidin-4(3H)-one, 5-{[2'-(1H-tetrazol-5-yl)biphenyl-4-yl]methyl}-6-butyl-3-(5,6-dimethyl-1,2,4-triazin-3-yl)-2-methylpyrimidin-4(3H)-one, 5-{[2'-(1H-tetrazol-5-yl)biphenyl-4-yl]methyl}-6-butyl-2-methyl-3-(thiazol-2-yl)pyrimidin-4(3H)-one, 5-{[2'-(1H-tetrazol-5-yl)biphenyl-4-yl]methyl}-6-butyl-3-(isoxazol-3-yl)-2-methylpyrimidin-4(3H)-one, 5-{[2'-(1H-tetrazol-5-yl)biphenyl-4-yl]methyl}-6-butyl-2-methyl-3-(1-methyl-1H-pyrazol-5-yl)pyrimidin-4(3H)-one, 5-{[2'-(1H-tetrazol-5-yl)biphenyl-4-yl]methyl}-6-butyl-2-methyl-3-(1-methyl-1H-1,2,4-triazol-3-yl)pyrimidin-4(3H)-one, 5-{[2'-(1H-tetrazol-5-yl)biphenyl-4-yl]methyl}-6-butyl-2-methyl-3-(quinolin-2-yl)pyrimidin-4(3H)-one, 5-{[2'-(1H-tetrazol-5-yl)biphenyl-4-yl]methyl}-6-butyl-3-(isoquinolin-1-yl)-2-methylpyrimidin-4(3H)-one, 5-{[2'-(1H-tetrazol-5-yl)biphenyl-4-yl]methyl}-6-butyl-3-(isoquinolin-3-yl)-2-methylpyrimidin-4(3H)-one, 5-{[2'-(1H-tetrazol-5-yl)biphenyl-4-yl]methyl}-6-butyl-2-methyl-3-(1-methyl-1H-benzimidazol-2-yl)pyrimidin-4(3H)-one, and 5-{[2'-(1H-tetrazol-5-yl)biphenyl-4-yl]methyl}-3-(benzothiazol-2-yl)-6-butyl-2-methylpyrimidin-4(3H)-one.

Further, the alkyl group like butyl and propyl for describing the above compounds indicates a linear chain (i.e., normal), unless specifically described otherwise.

[6] A pharmaceutical composition containing the 3-heteroarylpyrimidin-4-(3H)-one derivative described in any of the above [1] to [5] or salt thereof, or solvate thereof, and a pharmaceutically acceptable carrier.

[7] A pharmaceutical composition which has both angiotensin II receptor antagonistic activity and PPARγ activation activity and contains as an effective component the 3-heteroarylpyrimidin-4-(3H)-one derivative described in any of the above [1] to [5] or salt thereof, or solvate thereof.

[8] An agent for preventing and/or treating a circulatory disorder which contains as an effective component the 3-heteroarylpyrimidin-4-(3H)-one derivative described in any of the above [1] to [5] or salt thereof, or solvate thereof.

[9] The agent for preventing and/or treating a circulatory disorder described in the above [8], wherein the circulatory disorder is hypertension, heart diseases, angina pectoris, cerebrovascular disorders, cerebral circulatory disorders, ischemic peripheral circulatory disorders, renal diseases, or arteriosclerosis.

[10] An agent for preventing and/or treating a metabolic disorder which contains as an effective component the 3-heteroarylpyrimidin-4-(3H)-one derivative described in any of the above [1] to [5] or salt thereof, or solvate thereof.

[11] The agent for preventing and/or treating a metabolic disorder described in the above [10], wherein the metabolic disorder is type 2 diabetes, diabetic complications (diabetic retinopathy, diabetic neuropathy, or diabetic nephropathy), insulin resistance syndrome, metabolic syndrome, or hyperinsulinemia.

[12] A method of preventing and/or treating a circulatory disorder, characterized in that an effective amount of the 3-heteroarylpyrimidin-4-(3H)-one derivative described in any of the above [1] to [5] or salt thereof, or solvate thereof is administered to a patient who is in need of treatment.

[13] A method of preventing and/or treating a metabolic disorder, characterized in that an effective amount of the 3-heteroarylpyrimidin-4-(3H)-one derivative described in any of the above [1] to [5] or salt thereof, or solvate thereof is administered to a patient who is in need of treatment.

[14] Use of the 3-heteroarylpyrimidin-4-(3H)-one derivative described in any of the above [1] to [5] or salt thereof, or solvate thereof for producing a preparation for preventing and/or treating a circulatory disorder.

[15] Use of the 3-heteroarylpyrimidin-4-(3H)-one derivative described in any of the above [1] to [5] or salt thereof, or solvate thereof for producing a preparation for preventing and/or treating a metabolic disorder.

[16] The 3-heteroarylpyrimidin-4-(3H)-one derivative described in any of the above [1] to [5] or salt thereof, or solvate thereof as a prophylactic and/or therapeutic agent having both angiotensin II receptor antagonistic activity and PPARγ activation activity.

Effects of the Invention

The 3-heteroarylpyrimidin-4-(3H)-one derivative represented by the formula (I) of the invention, or salt or solvate thereof exhibits a potent antagonistic activity for an angiotensin II receptor, and can be appropriately used as an effective component of an agent for preventing and/or treating a disorder related with angiotensin II, for example a circulatory disorder like hypertension, heart diseases, angina pectoris, cerebrovascular disorders, cerebral circulatory disorders, ischemic peripheral circulatory disorders, renal diseases, and arteriosclerosis.

Further, the 3-heteroarylpyrimidin-4-(3H)-one derivative represented by the formula (I) of the invention, or salt or solvate thereof has a PPARγ activation activity and can be appropriately used as an effective component of an agent for preventing and/or treating a disorder related with PPARγ, for example a metabolic disorder like arteriosclerosis, type 2 diabetes, diabetic complications (diabetic retinopathy, diabetic neuropathy, or diabetic nephropathy), insulin resistance syndrome, Syndrome X, metabolic syndrome, and hyperinsulinemia.

Still further, the 3-heteroarylpyrimidin-4-(3H)-one derivative represented by the formula (I) of the invention, or salt or solvate thereof has both an antagonistic activity for an angiotensin II receptor and a PPARγ activation activity and can be appropriately used as an effective component of an agent for preventing and/or treating a disorder related with both angiotensin II and PPARγ, for example arteriosclerosis, diabetic nephropathy, insulin resistance syndrome, Syndrome X, and metabolic syndrome.

Modes For Carrying Out The Invention

The "halogen atom" as used herein includes a fluorine atom, a chlorine atom, a bromine atom or an iodine atom.

The "$C_{1-6}$ alkyl group" as used herein means a linear or a branched hydrocarbon group having 1 to 6 carbon atoms, and examples thereof include a methyl group, an ethyl group, a n-propyl group, an isopropyl group, a n-butyl group, an isobutyl group, a t-butyl group, a n-pentyl group, a 2-methylbutyl group, a 2,2-dimethylpropyl group, and a n-hexyl group.

The "halo $C_{1-6}$ alkyl group" as used herein means a linear or a branched alkyl group having 1 to 6 carbon atoms substituted with one to largest possible number of halogen atoms, which are the same or different from each other, and examples thereof include a monofluoromethyl group, a trifluoromethyl group, a monochloromethyl group, a monobromomethyl group, a monoiodomethyl group, and a 2,2,2-trifluoroethyl group and the like.

The "$C_{1-6}$ alkoxy group" as used herein means a linear or a branched alkoxy group having 1 to 6 carbon atoms and examples thereof include a methoxy group, an ethoxy group, a propoxy group, an isopropoxy group, a butoxy group, an isobutoxy group, a sec-butoxy group, a tert-butoxy group, a pentoxy group, an isopentoxy group, a neopentoxy group, a hexyloxy group, and an isohexyloxy group.

The "substituent group" for the "$C_{1-6}$ alkoxy group which may have a substituent group" may be the same or different from each other and the alkoxy group may be substituted with one to largest possible number of the substituent group. Examples of the "substituent group" include a phenyl group; a hydroxyl group; a $C_{1-6}$ alkylthio group; a $C_{1-6}$ alkylsulfonyl group; an oxazolyl group which may be substituted with a 5- to 10-membered heteroaryl group which may be substituted with a $C_{1-6}$ alkyl group, a $C_{6-10}$ aryl group, or a halogen atom; a pyridyl group which may be substituted with a $C_{1-6}$ alkyl group; a $C_{1-6}$ alkoxycarbonyl group; a carboxyl group; a carbamoyl group; a mono $C_{1-6}$ alkylcarbamoyl group; a di $C_{1-6}$ alkylcarbamoyl group; a $C_{1-6}$ alkanoylamino group; a $C_{1-6}$ alkylsulfonylamino group; a halo $C_{1-6}$ alkylsulfonylamino group; an amide group; and a sulfonamide group.

Examples of the "$C_{3-6}$ cycloalkyloxy group" as used herein include a cyclopropyloxy group, a cyclobutyloxy group, a cyclopentyloxy group, and a cyclohexyloxy group.

Examples of the "substituent group" for the "$C_{3-6}$ cycloalkyloxy group which may have a substituent group" include an oxo group. Examples of the $C_{3-6}$ cycloalkyloxy group which may have a substituent group include a 4-oxo-cyclohexyloxy group.

The "5- to 10-membered heteroaryl group" as used herein means a 5- to 10-membered monocyclic heteroaromatic group or fused heteroaromatic group which contains, as a ring-constituting atom, 1 to 4 heteroatoms selected from a nitrogen atom, an oxygen atom, or a sulfur atom in addition to the carbon atoms. Examples of the monocyclic heteroaromatic group include a pyridyl group (pyridin-2-yl group and the like), a pyrimidinyl group (a pyrimidin-2-yl group, a pyrimidin-4-yl group and the like), a pyrazinyl group (pyrazin-2-yl group and the like), a triazinyl group (1,2,4-triazin-3-yl group and the like), a thiazolyl group (thiazol-2-yl group and the like), an isoxazolyl group (isoxazol-3-yl group and the like), a pyrazolyl group (pyrazol-3-yl group), a triazolyl group (1,2,4-triazol-2-yl group and the like), a tetrazolyl group, and a furanyl group. Examples of the fused heteroaromatic group include a quinolynyl group (quinolin- 2-yl group and the like), an isoquinolynyl group (isoquinolin-1-yl group and the like), a benzimidazolyl group (a benzimidazol-2-yl group and the like) and a benzothiazolyl group (benzothiazol-2-yl group and the like).

The "$C_{1-6}$ alkylthio group" as used herein means a linear or branched alkylthio group having 1 to 6 carbon atoms and examples thereof include a methylthio group, an ethylthio group, a n-propylthio group, an isopropylthio group, a n-butylthio group, an isobutylthio group, a sec-butylthio group, a tert-butylthio group, a n-pentylthio group, an isopentylthio group, a neopentylthio group, a 1-methylbutylthio group, a 1-ethylpropylthio group, a n-hexylthio group, an isohexylthio group, a 3-methylpentylthio group, a 2-methylpentylthio group, a 1-methylpentylthio group, a 3,3-dimethylbutylthio group, a 2,2-dimethylbutylthio group, a 1,1-dimethylbutylthio group, a 1,2-dimethylbutylthio group, a 1,3-dimethylbutylthio group, a 2,3-dimethylbutylthio group, a 1-ethylbutylthio group, and a 2-ethylbutylthio group.

The "$C_{1-6}$ alkylsulfonyl group" as used herein means a linear or branched alkylsulfonyl group having 1 to 6 carbon atoms and examples thereof include a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a n-pentylsulfonyl group, an isopentylsulfonyl group, a neopentylsulfonyl group, a 1-methylbutylsulfonyl group, a 1-ethylpropylsulfonyl group, a n-hexylsulfonyl group, an isohexylsulfonyl group, a 3-methylpentylsulfonyl group, a 2-methylpentylsulfonyl group, a 1-methylpentylsulfonyl group, a 3,3-dimethylbutylsulfonyl group, a 2,2-dimethylbutylsulfonyl group, a 1,1-dimethylbutylsulfonyl group, a 1,2-dimethylbutylsulfonyl group, a 1,3-dimethylbutylsulfonyl group, a 2,3-dimethylbutylsulfonyl group, a 1-ethylbutylsulfonyl group, and a 2-ethylbutylsulfonyl group.

Examples of the "$C_{1-6}$ alkoxycarbonyl group" as used herein include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentoxycarbonyl group, an isopentoxycarbonyl group (3-methylbutoxycarbonyl group), a neopentoxycarbonyl group (2,2-dimethylpropoxycarbonyl group), a 1-methylbutoxycarbonyl group, a 1-ethylpropoxycarbonyl group, a n-hexyloxycarbonyl group, an isohexyloxycarbonyl group, a 3-methylpentoxycarbonyl group, a 2-methylpentoxycarbonyl group, a 1-methylpentoxycarbonyl group, a 3,3-dimethylbutoxycarbonyl group, a 2,2-dimethylbutoxycarbonyl group, a 1,1-dimethylbutoxycarbonyl group, a 1,2-dimethylbutoxycarbonyl group, a 1,3-dimethylbutoxycarbonyl group, a 2,3-dimethylbutoxycarbonyl group, a 1-ethylbutoxycarbonyl group, and a 2-ethylbutoxycarbonyl group.

The "carbamoyl group which may be substituted with $C_{1-6}$ alkyl" as used herein means an unsubstituted carbamoyl group or a carbamoyl group wherein one or two $C_{1-6}$ alkyl(s) are substituted on the nitrogen atom. Specific examples thereof include a carbamoyl group, a N-methylcarbamoyl group, a N,N-dimethylcarbamoyl group, a N-ethylcarbamoyl group, a N,N-diethylcarbamoyl group, a N-propylcarbamoyl group, a N-isopropylcarbamoyl group, a N,N-dipropylcarbamoyl group, a N-butylcarbamoyl group, and a N,N-dibutylcarbamoyl group.

Examples of the "$C_{1-6}$ alkanoylamino group" as used herein include a formylamino group, an acetylamino group, a propionylamino group, a butyrylamino group, an isobutyrylamino group, a valerylamino group, an isovalerylamino group, and a pyvaloylamino group.

Examples of the "$C_{1-6}$ alkylsulfonylamino group" as used herein include a methylsulfonylamino group, an ethylsulfonylamino group, a n-propylsulfonylamino group, an isopropylsulfonylamino group, a n-butylsulfonylamino group, an isobutylsulfonylamino group, a t-butylsulfonylamino group, a n-pentylsulfonylamino group, a 2-methylbutylsulfonylamino group, a 2,2-dimethylpropylsulfonylamino group, and a n-hexylsulfonylamino group.

Examples of the "halo $C_{1-6}$ alkylsulfonylamino group" as used herein include a monofluoromethylsulfonylamino group, a trifluoromethylsulfonylamino group, a monochloromethylsulfonylamino group, a monobromomethylsulfonylamino group, a monoiodomethylsulfonylamino group, and a 2,2,2-trifluoroethylsulfonylamino group.

Preferred examples of the invention include the followings.

As for the heterocyclic group in A of the formula (I), any one heterocyclic group selected from the following formulae is preferable.

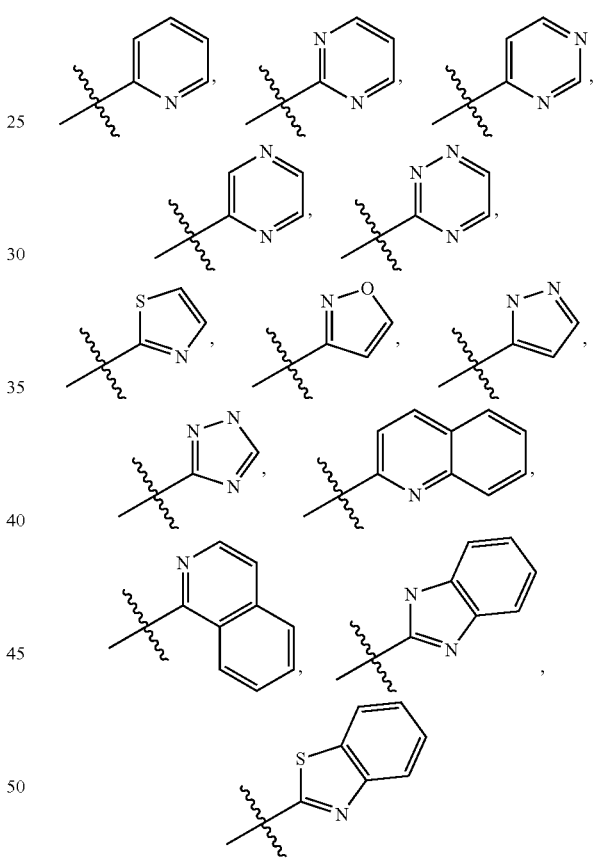

As for $R^1$ of the formula (I), preferred examples of the $C_{1-6}$ alkyl group include a linear or branched hydrocarbon group having 1 to 4 carbon atoms, i.e., a $C_{1-4}$ alkyl group, and more preferred examples include an n-butyl group.

As for $R^2$ of the formula (I), preferred examples of the $C_{1-6}$ alkyl group include a $C_{1-4}$ alkyl group, and more preferred examples include a methyl group.

As for $R^3$, $R^4$, and $R^5$ of the formula (I), preferred examples of the halogen atom include a fluorine atom, a chlorine atom, and a bromine atom.

As for $R^3$, $R^4$, and $R^5$ of the formula (I), preferred examples of the $C_{1-6}$ alkyl group include a $C_{1-4}$ alkyl group, and more preferred examples include a methyl group.

As for $R^3$, $R^4$, and $R^5$ of the formula (I), preferred examples of the halo $C_{1-6}$ alkyl group include a halo $C_{1-4}$ alkyl group, and more preferred examples include a trifluoromethyl group.

As for $R^3$, $R^4$, and $R^5$ of the formula (I), preferred examples of the "$C_{1-6}$ alkoxy group" in the $C_{1-6}$ alkoxy group which may have a substituent group include a $C_{1-4}$ alkoxy group, and more preferred examples include a methoxy group, an ethoxy group, a propoxy group, an isopropoxy group, and a n-butoxy group. As for the substituent group, preferred examples of the "substituent group" include a phenyl group, a hydroxyl group, a $C_{1-6}$ alkylthio group (in particular, a methylthio group), a $C_{1-6}$ alkylsulfonyl group (in particular, a methylsulfonyl group), an oxazolyl group, a substituted oxazolyl group (preferred examples of the substituent group include a $C_{1-6}$ alkyl group, a $C_{6-10}$ aryl group, and a 5- to 10-membered heteroaryl group which may be substituted with a halogen atom, more preferred examples include a $C_{1-4}$ alkyl group, a phenyl group, a naphthyl group, and a furanyl group which may be substituted with a halogen atom, and particularly preferred examples include a 5-methyl-2-phenyloxazol-4-yl group, a 2-(furan-2-yl)-5-methyloxazol-4-yl group, a 2-(5-bromofuran-2-yl)-5-methyloxazol-4-yl group, and a 2-(naphthalen-2-yl)-5-methyloxazol-4-yl group), a substituted or unsubstituted pyridyl group (in particular, a pyridin-2-yl group, a 5-ethylpyridin-2-yl group and the like are preferable), a $C_{1-6}$ alkoxycarbonyl group (in particular, an ethoxycarbonyl group), a carboxyl group, a carbamoyl group which may be substituted with $C_{1-6}$ alkyl (in particular, a carbamoyl group, a N-methylcarbamoyl group, a N,N-dimethylcarbamoyl group, a N-ethylcarbamoyl group, a N,N-diethylcarbamoyl group, a N-propylcarbamoyl group, a N-isopropylcarbamoyl group and the like are preferable), a $C_{1-6}$ alkanoylamino group (in particular, an acetylamino group and the like are preferable), a $C_{1-6}$ alkylsulfonylamino group (in particular, a methylsulfonylamino group and the like are preferable), and a halo $C_{1-6}$ alkylsulfonylamino group (in particular, a trifluoromethylsulfonylamino group and the like are preferable).

More preferred examples of the 3-heteroarylpyrimidin-4-(3H)-one derivative compounds that are represented by the formula (I) include a compound that is selected from a group consisting of following compounds:

5-{[2'-(1H-tetrazol-5-yl)biphenyl-4-yl]methyl}-6-butyl-2-methyl-3-(pyridin-2-yl)pyrimidin-4(3H)-one (see, Example 1), 5-{[2'-(1H-tetrazol-5-yl)biphenyl-4-yl]methyl}-6-butyl-2-methyl-3-(5-methylpyridin-2-yl)pyrimidin-4(3H)-one (see, Example 2), 5-{[2'-(1H-tetrazol-5-yl)biphenyl-4-yl]methyl}-6-butyl-3-(5-methoxypyridin-2-yl)-2-methylpyrimidin-4(3H)-one (see, Example 3), 5-{[2'-(1H-tetrazol-5-yl)biphenyl-4-yl]methyl}-6-butyl-3-(3-fluoropyridin-2-yl)-2-methylpyrimidin-4(3H)-one (see, Example 4), 5-{[2'-(1H-tetrazol-5-yl)biphenyl-4-yl]methyl}-6-butyl-3-(5-fluoropyridin-2-yl)-2-methylpyrimidin-4(3H)-one (see, Example 5), 5-{[2'-(1H-tetrazol-5-yl)biphenyl-4-yl]methyl}-6-butyl-3-(3-chloropyridin-2-yl)-2-methylpyrimidin-4(3H)-one (see, Example 6), 5-{[2'-(1H-tetrazol-5-yl)biphenyl-4-yl]methyl}-6-butyl-3-(5-chloropyridin-2-yl)-2-methylpyrimidin-4(3H)-one (see, Example 7), 5-{[2'-(1H-tetrazol-5-yl)biphenyl-4-yl]methyl}-3-(6-bromopyridin-2-yl)-6-butyl-2-methylpyrimidin-4(3H)-one (see, Example 8), 5-{[2'-(1H-tetrazol-5-yl)biphenyl-4-yl]methyl}-6-butyl-2-methyl-3-[3-(trifluoromethyl)pyridin-2-yl]pyrimidin-4(3H)-one (see, Example 9), 5-{[2'-(1H-tetrazol-5-yl)biphenyl-4-yl]methyl}-6-butyl-2-methyl-3-[4-(trifluoromethyl)pyridin-2-yl]pyrimidin-4(3H)-one (see, Example 10), 5-{[2'-(1H-tetrazol-5-yl)biphenyl-4-yl]methyl}-6-butyl-2-methyl-3-[5-(trifluoromethyl)pyridin-2-yl]pyrimidin-4(3H)-one (see, Example 11), 5-{[2'-(1H-tetrazol-5-yl)biphenyl-4-yl]methyl}-6-butyl-2-methyl-3-[6-(trifluoromethyl)pyridin-2-yl]pyrimidin-4(3H)-one (see, Example 12), 5-{[2'-(1H-tetrazol-5-yl)biphenyl-4-yl]methyl}-6-butyl-3-[3-chloro-5-(trifluoromethyl)pyridin-2-yl]-2-methylpyrimidin-4(3H)-one (see, Example 13), 5-{[2'-(1H-tetrazol-5-yl)biphenyl-4-yl]methyl}-6-butyl-2-methyl-3-(5-nitropyridin-2-yl)pyrimidin-4(3H)-one (see, Example 14), 5-{[2'-(1H-tetrazol-5-yl)biphenyl-4-yl]methyl}-3-[5-(1H-tetrazol-5-yl)pyridin-2-yl]-6-butyl-2-methylpyrimidin-4(3H)-one (see, Example 15), 5-{[2'-(1H-tetrazol-5-yl)biphenyl-4-yl]methyl}-3-(5-bromopyrimidin-2-yl)-6-butyl-2-methylpyrimidin-4(3H)-one (see, Example 16), 5-{[2'-(1H-tetrazol-5-yl)biphenyl-4-yl]methyl}-6-butyl-2-methyl-3-(pyrimidin-2-yl)pyrimidin-4(3H)-one (see, Example 17), 5-{[2'-(1H-tetrazol-5-yl)biphenyl-4-yl]methyl}-6-butyl-3-(5-methoxypyrimidin-2-yl)-2-methylpyrimidin-4(3H)-one (see, Example 18), 5-{[2'-(1H-tetrazol-5-yl)biphenyl-4-yl]methyl}-3-[5-(benzyloxy)pyrimidin-2-yl]-6-butyl-2-methylpyrimidin-4(3H)-one (see, Example 19), 5-{[2'-(1H-tetrazol-5-yl)biphenyl-4-yl]methyl}-6-butyl-3-(5-hydroxypyrimidin-2-yl)-2-methylpyrimidin-4(3H)-one (see, Example 20), 5-{[2'-(1H-tetrazol-5-yl)biphenyl-4-yl]methyl}-6-butyl-3-(5-ethoxypyrimidin-2-yl)-2-methylpyrimidin-4(3H)-one (see, Example 21), 5-{[2'-(1H-tetrazol-5-yl)biphenyl-4-yl]methyl}-6-butyl-2-methyl-3-(5-propoxypyrimidin-2-yl)pyrimidin-4(3H)-one (see, Example 22), 5-{[2'-(1H-tetrazol-5-yl)biphenyl-4-yl]methyl}-6-butyl-3-(5-isopropoxypyrimidin-2-yl)-2-methylpyrimidin-4(3H)-one (see, Example 23), 5-{[2'-(1H-tetrazol-5-yl)biphenyl-4-yl]methyl}-3-(5-butoxypyrimidin-2-yl)-6-butyl-2-methylpyrimidin-4(3H)-one (see, Example 24), 5-{[2'-(1H-tetrazol-5-yl)biphenyl-4-yl]methyl}-6-butyl-3-[5-(3-hydroxypropoxy)pyrimidin-2-yl]-2-methylpyrimidin-4(3H)-one (see, Example 25), 5-{[2'-(1H-tetrazol-5-yl)biphenyl-4-yl]methyl}-6-butyl-2-methyl-3-{5-[2-(methylthio)ethoxy]pyrimidin-2-yl}pyrimidin-4(3H)-one (see, Example 26), 5-{[2'-(1H-tetrazol-5-yl)biphenyl-4-yl]methyl}-6-butyl-2-methyl-3-{5-[2-(methylsulfonyl)ethoxy]pyrimidin-2-yl}pyrimidin-4(3H)-one (see, Example 27), 5-{[2'-(1H-tetrazol-5-yl)biphenyl-4-yl]methyl}-6-butyl-3-[5-(cyclohexyloxy)pyrimidin-2-yl]-2-methylpyrimidin-4(3H)-one (see, Example 28), 5-{[2'-(1H-tetrazol-5-yl)biphenyl-4-yl]methyl}-6-butyl-2-methyl-3-[5-(4-oxocyclohexyloxy)pyrimidin-2-yl]pyrimidin-4(3H)-one (see, Example 29), 5-{[2'-(1H-tetrazol-5-yl)biphenyl-4-yl]methyl}-6-butyl-3-(4,6-dichloropyrimidin-2-yl)-2-methylpyrimidin-4(3H)-one (see, Example 30), 5-{[2'-(1H-tetrazol-5-yl)biphenyl-4-yl]methyl}-6-butyl-2-methyl-3-{5-[(5-methyl-2-phenyloxazol-4-yl)methoxy]pyrimidin-2-yl}pyrimidin-4(3H)-one (see, Example 31), 5-{[2'-(1H-tetrazol-5-yl)biphenyl-4-yl]methyl}-3-{5-{[2-(5-bromofuran-2-yl)-5-methyloxazol-4-yl]methoxy}pyrimidin-2-yl}-6-butyl-2-methylpyrimidin-4(3H)-one (see, Example 32), 5-{[2'-(1H-tetrazol-5-yl)biphenyl-4-yl]methyl}-6-butyl-3-{5-{[2-(furan-2-yl)-5-methyloxazol-4-yl]methoxy}pyrimidin-2-yl}-2-methylpyrimidin-4(3H)-one (see, Example 33), 5-{[2'-(1H-tetrazol-5-yl)biphenyl-4-yl]methyl}-6-butyl-2-methyl-3-{5-{[5-methyl-2-(naphthalen-2-yl)oxazol-4-yl]methoxy}pyrimidin-2-yl}-pyrimidin-4(3H)-one (see, Example 34), 5-{[2'-(1H-tetrazol-5-yl)biphenyl-4-yl]methyl}-6-butyl-2-methyl-3-{5-[2-(5-methyl-2-phenyloxazol-4-yl)ethoxy]pyrimidin-2-yl}pyrimidin-4(3H)-one (see, Example 35), 5-{[2'-(1H-tetrazol-5-yl)biphenyl-4-yl]methyl}-6-butyl-3-{5-[2-(5-ethylpyridin-2-yl)ethoxy]pyrimidin-2-yl}-2-methylpyrimidin-4(3H)-one (see, Example 36), ethyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetate (see, Example 37), 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetic acid (see, Example 38), 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetamide (see, Example 39), 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylacetamide (see, Example 40), 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylacetamide (see, Example 41), 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetic acid (see, Example 42), 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-3-phenylpropionic acid (see, Example 43), 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetamide (see, Example 44), ethyl 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanoic acid (see, Example 45), 4-{2-{5-{[2'-(1H-tetrazol-5-yl)biphenyl-4-yl]methyl}-4-butyl-2-methyl-6-oxopyrimidin-1(6H)-yl}pyrimidin-5-yl Oxy}butanoic acid (see, Example 46), 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanamide (see, Example 47), 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-methylbutanamide (see, Example 48), 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylbutanamide (see, Example 49), 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-propylbutanamide (see, Example 50), 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-isopropylbutanamide (see, Example 51), 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylbutanamide (see, Example 52), 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}pentanamide (see, Example 53), 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylpentanamide (see, Example 54), 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylpentanamide (see, Example 55), N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}acetamide (see, Example 56), N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}methane sulfonamide (see, Example 57), N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}-1,1,1-trifluoromethane sulfonamide (see, Example 58), 5-{[2'-(1H-tetrazol-5-yl)biphenyl-4-yl]-6-butyl-3-(2,6-dimethoxypyrimidin-4-yl)-2-methylpyrimidin-4(3H)-one (see, Example 59), 5-{[2'-(1H-tetrazol-5-yl)biphenyl-4-yl]methyl}-6-butyl-2-methyl-3-(pyrazin-2-yl)pyrimidin-4(3H)-one (see, Example 60)

5-{[2'-(1H-tetrazol-5-yl)biphenyl-4-yl]methyl}-6-butyl-3-(5,6-dimethyl-1,2,4-triazin-3-yl)-2-methylpyrimidin-4(3H)-one (see, Example 61), 5-{[2'-(1H-tetrazol-5-yl)biphenyl-4-yl]methyl}-6-butyl-2-methyl-3-(thiazol-2-yl)pyrimidin-4(3H)-one (see, Example 62), 5-{[2'-(1H-tetrazol-5-yl)biphenyl-4-yl]methyl}-6-butyl-3-(isoxazol-3-yl)-2-methylpyrimidin-4(3H)-one (see, Example 63), 5-{[2'-(1H-tetrazol-5-yl)biphenyl-4-yl]methyl}-6-butyl-2-methyl-3-(1-methyl-1H-pyrazol-5-yl)pyrimidin-4(3H)-one (see, Example 64), 5-{[2'-(1H-tetrazol-5-yl)biphenyl-4-yl]methyl}-6-butyl-2-methyl-3-(1-methyl-1H-1,2,4-triazol-3-yl)pyrimidin-4(3H)-one (see, Example 65), 5-{[2'-(1H-tetrazol-5-yl)biphenyl-4-yl]methyl}-6-butyl-2-methyl-3-(quinolin-2-vl)pyrimidin-4(3H)-one (see, Example 66), 5-{[2'-(1H-tetrazol-5-yl)biphenyl-4-yl]methyl}-6-butyl-3-(isoquinolin-1-yl)-2-methylpyrimidin-4(3H)-one (see, Example 67), 5-{[2'-(1H-tetrazol-5-yl)biphenyl-4-yl]methyl}-6-butyl-3-(isoquinolin-3-yl)-2-methylpyrimidin-4(3H)-one (see, Example 68), 5-{[2'-(1H-tetrazol-5-yl)biphenyl-4-yl]methyl}-6-butyl-2-methyl-3-(1-methyl-1H-benzimidazol-2-yl)pyrimidin-4(3H)-one (see, Example 69), and 5-{[2'-(1H-tetrazol-5-yl)biphenyl-4-yl]methyl}-3-(benzothiazol-2-yl)-6-butyl-2-methylpyrimidin-4(3H)-one (see, Example 70).

Still more preferred examples of the pyrimidin-4(3H)-one derivatives that are represented by the formula (I) include a compound that is selected from a group consisting of following compounds:

5-{[2'-(1H-tetrazol-5-yl)biphenyl-4-yl]methyl}-6-butyl-2-methyl-3-(5-methylpyridin-2-yl)pyrimidin-4(3H)-one, (see, Example 2)

5-{[2'-(1H-tetrazol-5-yl)biphenyl-4-yl]methyl}-6-butyl-3-(5-methoxypyridin-2-yl)-2-methylpyrimidin-4(3H)-one, (see, Example 3)

5-{[2'-(1H-tetrazol-5-yl)biphenyl-4-yl]methyl}-6-butyl-3-(3-fluoropyridin-2-yl)-2-methylpyrimidin-4(3H)-one, (see, Example 4)

5-{[2'-(1H-tetrazol-5-yl)biphenyl-4-yl]methyl}-6-butyl-3-(5-fluoropyridin-2-yl)-2-methylpyrimidin-4(3H)-one, (see, Example 5)

5-{[2'-(1H-tetrazol-5-yl)biphenyl-4-yl]methyl}-6-butyl-3-(3-chloropyridin-2-yl)-2-methylpyrimidin-4(3H)-one, (see, Example 6)

5-{[2'-(1H-tetrazol-5-yl)biphenyl-4-yl]methyl}-6-butyl-3-(5-chloropyridin-2-yl)-2-methylpyrimidin-4(3H)-one, (see, Example 7)

5-{[2'-(1H-tetrazol-5-yl)biphenyl-4-yl]methyl}-3-(6-bromopyridin-2-yl)-6-butyl-2-methylpyrimidin-4(3H)-one, (see, Example 8)

5-{[2'-(1H-tetrazol-5-yl)biphenyl-4-yl]methyl}-6-butyl-2-methyl-3-[4-(trifluoromethyl)pyridin-2-yl]pyrimidin-4(3H)-one, (see, Example 10)

5-{[2'-(1H-tetrazol-5-yl)biphenyl-4-yl]methyl}-6-butyl-2-methyl-3-[5-(trifluoromethyl)pyridin-2-yl]pyrimidin-4(3H)-one, (see, Example 11)

5-{[2'-(1H-tetrazol-5-yl)biphenyl-4-yl]methyl}-6-butyl-3-[3-chloro-5-(trifluoromethyl)pyridin-2-yl]-2-methylpyrimidin-4(3H)-one, (see, Example 13)

5-{[2'-(1H-tetrazol-5-yl)biphenyl-4-yl]methyl}-3-5-bromopyrimidin-2-yl)-6-butyl-2-methylpyrimidin-4(3H)-one, (see, Example 16)

5-{[2'-(1H-tetrazol-5-yl)biphenyl-4-yl]methyl}-3-[5-(benzyloxy)pyrimidin-2-yl]-6-butyl-2-methylpyrimidin-4(3H)-one, (see, Example 19)

5-{[2'-(1H-tetrazol-5-yl)biphenyl-4-yl]methyl}-6-butyl-3-(5-ethoxypyrimidin-2-yl)-2-methylpyrimidin-4(3H)-one, (see, Example 21)

5-{[2'-(1H-tetrazol-5-yl)biphenyl-4-yl]methyl}-6-butyl-2-methyl-3-(5-propoxypyrimidin-2-yl)pyrimidin-4(3H)-one, (see, Example 22)

5-{[2'-(1H-tetrazol-5-yl)biphenyl-4-yl]methyl}-6-butyl-3-(5-isopropoxypyrimidin-2-yl)-2-methylpyrimidin-4(3H)-one, (see, Example 23)

5-{[2'-(1H-tetrazol-5-yl)biphenyl-4-yl]methyl}-3-(5-butoxypyrimidin-2-yl)-6-butyl-2-methylpyrimidin-4(3H)-one, (see, Example 24)

5-{[2'-(1H-tetrazol-5-yl)biphenyl-4-yl]methyl}-6-butyl-2-methyl-3-{5-[2-(methylthio)ethoxy]pyrimidin-2-yl}pyrimidin-4(3H)-one, (see, Example 26)

5-{[2'-(1H-tetrazol-5-yl)biphenyl-4-yl]methyl}-6-butyl-3-[5-(cyclohexyloxy)pyrimidin-2-yl]-2-methylpyrimidin-4(3H)-one, (see, Example 28)

5-{[2'-(1H-tetrazol-5-yl)biphenyl-4-yl]methyl}-6-butyl-3-{5-[2-(5-ethylpyridin-2-yl)ethoxy]pyrimidin-2-yl}-2-methylpyrimidin-4(3H)-one, (see, Example 36)

2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetic acid, (see, Example 42)

4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanamide, (see, Example 47)

4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylbutanamide, (see, Example 49)

4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylbutanamide, (see, Example 52)

N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}-1,1,1-trifluoromethane sulfonamide, (see, Example 58)

5-{[2'-(1H-tetrazol-5-yl)biphenyl-4-yl]-6-butyl-3-(2,6-dimethoxypyrimidin-4-yl)-2-methylpyrimidin-4(3H)-one, (see, Example 59)

5-{[2'-(1H-tetrazol-5-yl)biphenyl-4-yl]methyl}-6-butyl-2-methyl-3-(thiazol-2-yl)pyrimidin-4(3H)-one, (see, Example 62)

5-{[2'-(1H-tetrazol-5-yl)biphenyl-4-yl]methyl}-6-butyl-3-(isoxazol-3-yl)-2-methylpyrimidin-4(3H)-one, (see, Example 63)

5-{[2'-(1H-tetrazol-5-yl)biphenyl-4-yl]methyl}-6-butyl-2-methyl-3-(1-methyl-1H-pyrazol-5-yl)pyrimidin-4 (3H)-one, (see, Example 64)

5-{[2'-(1H-tetrazol-5-yl)biphenyl-4-yl]methyl}-6-butyl-2-methyl-3-(quinolin-2-yl)pyrimidin-4(3H)-one, (see, Example 66)

5-{[2'-(1H-tetrazol-5-yl)biphenyl-4-yl]methyl}-6-butyl-3-(isoquinolin-1-yl)-2-methylpyrimidin-4(3H)-one, (see, Example 67)

5-{[2'-(1H-tetrazol-5-yl)biphenyl-4-yl]methyl}-6-butyl-3-(isoquinolin-3-yl)-2-methylpyrimidin-4(3H)-one, (see, Example 68)

5-{[2'-(1H-tetrazol-5-yl)biphenyl-4-yl]methyl}-6-butyl-2-methyl-3-(1-methyl-1H-benzimidazol-2-yl)pyrimidin-4 (3H)-one, (see, Example 69), and 5-{[2'-(1H-tetrazol-5-yl)biphenyl-4-yl]methyl}-3-(benzothiazol-2-yl)-6-butyl-2-methylpyrimidin-4(3H)-one, (see, Example 70).

If the compound of the invention has geometrical isomers or optical isomers, the invention encompasses all of such isomers.

Salts of the compound represented by the formula (I) are not specifically limited, if they are pharmaceutically acceptable salts. When the compound is processed as an acidic compound, a metal salt like sodium salt, potassium salt, magnesium salt, and calcium salt; and a salt with an organic base like trimethylamine, triethylamine, pyridine, picoline, N-methylpyrrolidine, N-methyl piperidine, and N-methyl morpholine can be mentioned. When the compound is processed as a basic compound, an acid addition salt and the like including a salt with a mineral acid, for example, hydrochloric acid salt, hydrobromic acid salt, hydroiodic acid salt, sulfuric acid salt, nitric acid salt, phosphoric acid salt and the like, or an organic acid addition salt, for example, benzoic acid salt, methanesulfonic acid salt, ethanesulfonic acid salt, benzene sulfonic acid salt, p-toluene sulfonic acid salt, maleic acid salt, fumaric acid salt, tartaric acid salt, citric acid salt, and acetic acid salt can be mentioned.

Examples of the solvate of the compound represented by the formula (I) or salt thereof include a hydrate, but not limited thereto.

In addition, compounds which are metabolized in a living body and converted into the compounds represented by the aforementioned formula (I), so called prodrugs, all fall within the scope of the compounds of the invention. Examples of groups which form the prodrugs of the compounds of the invention include the groups described in "Progress in Medicine", Vol. 5, pp. 2157-2161, 1985, Life Science Medica, and the groups described in "Development of Drugs", Vol. 7, Molecular Designs, pp. 163-198, 1990, Hirokawa Shoten.

The compounds represented by the formula (I), or salts or solvates thereof can be produced according to various known methods, and the production method is not specifically limited. For example, the compounds can be produced according to the following reaction step. Further, when each reaction shown below is performed, functional groups other than the reaction sites may be protected beforehand as required, and deprotected in an appropriate stage. Furthermore, the reaction in each step may be performed by an ordinarily used method, and isolation and purification can be performed by a method suitably selected from conventional methods such as crystallization, recrystallization, chromatography, or the like, or a combination thereof.

Method for production of the compounds represented by the formula (I), or salts or solvates thereof:

The compounds represented by the formula (I) of the invention can be produced according to the following method. Specifically, as illustrated in the Reaction pathway 1 below, oxocarboxylic acid ester represented by the formula (II) is reacted with ammonium acetate, and subsequently reacted with acid anhydride represented by the formula (III) to give an acylamino compound represented by the formula (IV). The acylamino compound represented by the formula (IV) is reacted with an amine compound represented by the formula (V) to give a pyrimidinone derivative represented by the formula (VI). The pyrimidinone derivative represented by the formula (VI) is reacted with an azide compound to produce the compound represented by the formula (I) of the invention. This reaction pathway can be expressed with the following chemical reaction scheme.

[Reaction pathway 1]

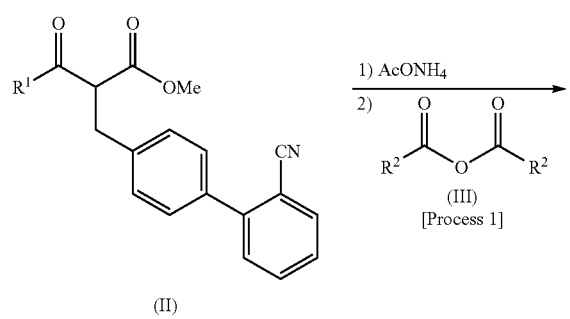

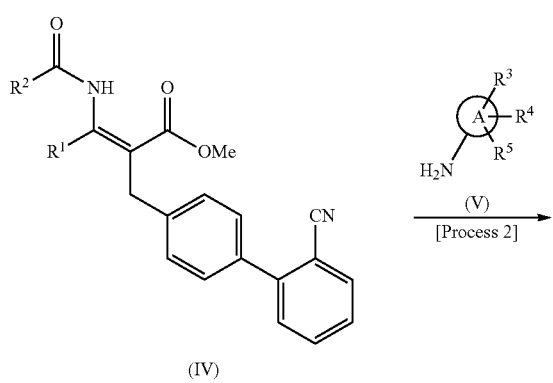

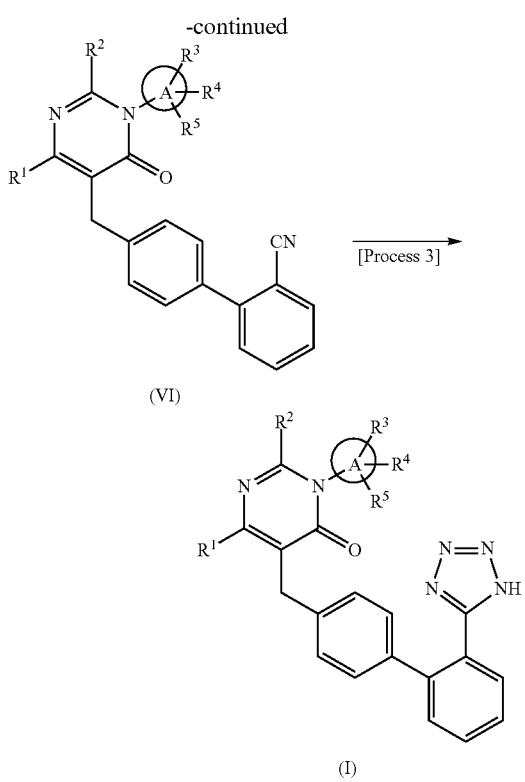

(in the formula, A, $R^1$, $R^2$, $R^3$, $R^4$, and $R^5$ are as defined above).

[Process 1] The reaction between the oxocarboxylic acid ester (II) and ammonium acetate may be carried out in a solvent in the presence of an acid. The solvent is not specifically limited, and methanol, ethanol, isopropanol, ethyl acetate, isopropyl acetate, toluene, benzene, dioxane, tetrahydrofuran, acetonitrile, propionitrile, N,N-dimethylformamide, N-methylpyrrolidone, and dimethyl sulfoxide may be used either alone or in combination thereof. The acid is not specifically limited, and the examples thereof include a protonic acid like acetic acid, trifluoro acetic acid, propionic acid, and benzoic acid and Lewis acid like titanium tetrachloride, boron trifluoride, and stannic chloride. The reaction condition may vary depending on the reaction materials used. However, the reaction is generally carried out at 0 to 180° C., and preferably 50° C. to 120° C., for 1 min to 24 hrs, and preferably for 5 min to 12 hrs.

The reaction with the acid anhydride (III) may be carried out in the presence of an acid. The acid is not particularly limited, and examples thereof include a protonic acid like acetic acid, trifluoro acetic acid, propionic acid, and benzoic acid. The reaction condition may vary depending on the reaction materials used. However, the reaction is generally carried out at 0 to 180° C., and preferably 50° C. to 120° C., for 1 min to 24 hrs, and preferably for 5 min to 12 hrs to obtain the acylamino compound (IV).

[Process 2] The reaction between the acylamino compound (IV) obtained according to the method above and the amine compound (V) may be carried out in a solvent in the presence of trialkyl aluminum. The solvent is not specifically limited, and 1,2-dichloroethane, chloroform, dichloromethane, ethyl acetate, isopropyl acetate, toluene, benzene, tetrahydrofuran, dioxane, acetonitrile, and propionitrile may be used either alone or in combination thereof. Examples of the trialkyl aluminum include trimethyl aluminum, triethyl aluminum, and tripropyl aluminum. The reaction condition may vary depending on the reaction materials used. However, the reaction is generally carried out at 0 to 120° C., and preferably 50° C. to 100° C., for 1 min to 24 hrs, and preferably for 5 min to 18 hrs to obtain the pyrimidinone derivative (VI).

[Process 3] The reaction between pyrimidinone derivative (VI) and an azide compound may be carried out in a solvent. Examples of the azide compound include trimethyl tin azide, tributyl tin azide, triphenyl tin azide, sodium azide, and hydrazoic acid. Further, trimethylsilyl azide may be used in the presence of dibutyltin oxide. The solvent is not specifically limited, and methanol, ethanol, isopropanol, ethyl acetate, isopropyl acetate, toluene, benzene, dioxane, tetrahydrofuran, acetonitrile, propionitrile, N,N-dimethylformamide, N-methylpyrrolidone, and dimethyl sulfoxide may be used either alone or in combination thereof. The reaction condition may vary depending on the reaction materials used. However, the reaction is generally carried out at 0 to 180° C., and preferably 50° C. to 120° C., for 1 min to 2 weeks, and preferably for 1 hr to 3 days to obtain the target compound.

Furthermore, among the compounds (I), the compounds represented by the formula (Ia) may be produced according to the method illustrated by the Reaction pathway 2, but it is not limited thereto.

[Reaction pathway 2]

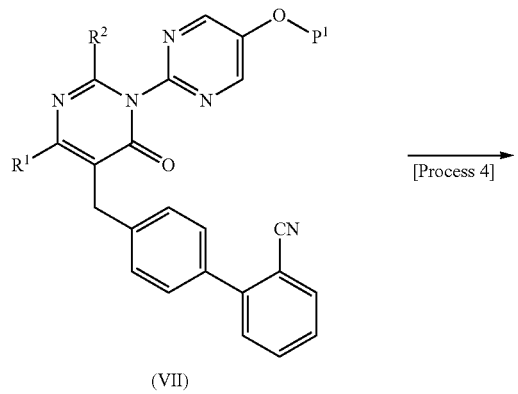

(VII)

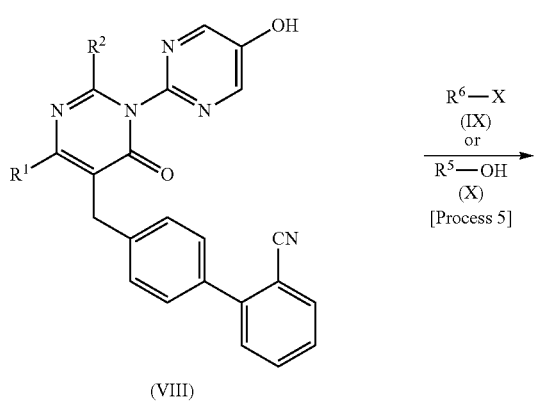

(VIII)

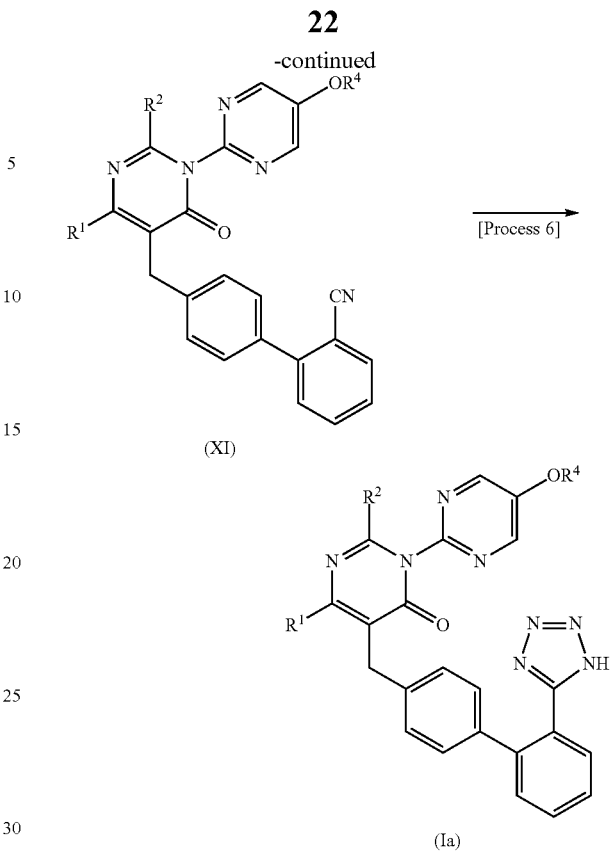

(in the formula, $R^1$ and $R^2$ are as defined above, $R^G$ represents a $C_{1-6}$ alkyl group which may have a substituent group, $P^1$ represents a protective group for hydroxyl group, for example, benzyl, and X represents a halogen atom).

[Process 4] The protective group like benzyl group which is introduced to an oxygen-containing functional group of the compound (VII) may be deprotected by a contact hydrogen addition method. The hydrogen source is not specifically limited, and the examples of the hydrogen source that can be used include hydrogen, formic acid, ammonium formate, and cyclohexadiene. The catalyst is not specifically limited, and the examples of the catalyst that can be used include palladium carbon, palladium black, platinum black, platinum dioxide, Raney nickel, palladium hydroxide, and carbon powder. The solvent is not specifically limited, and methanol, ethanol, isopropanol, ethyl acetate, isopropyl acetate, N,N-dimethylformamide, tetrahydrofuran, dioxane, acetonitrile, acetic acid, and water may be used either alone or in combination thereof. The reaction condition may vary depending on the reaction materials used. However, the reaction is generally carried out at 0 to 150° C., and preferably 0° C. to 100° C., for 30 min to 3 days, and preferably for 30 min to 50 hrs to obtain the compound (VIII).

[Process 5] The reaction between the compound (VIII) and the alkyl halide (IX) may be carried out in a solvent in the presence or absence of a base. The solvent is not specifically limited, and tetrahydrofuran, toluene, dioxane, N,N-dimethylformamide, N-methylpyrrolidone, dichloromethane, chloroform, acetonitrile, and propionitrile may be used either alone or in combination thereof. The base is not specifically limited, and the examples thereof include an organic base like pyridine, N,N-dimethylaminopyridine (DMAP), collidine, lutidine, 1,8-diazabicyclo[5.4.0]-7-undecene (DBU), 1,5-diazabicyclo[4.3.0]-5-nonene (DBN), 1,4-diazabicyclo[2.2.2]

octane (DABCO), triethylamine, diisopropylamine, diisopropylethylamine, diisopropylpentylamine, and trimethylamine, an alkali metal hydride like lithium hydride, sodium hydride, and potassium hydride, an alkali metal hydroxide like lithium hydroxide, sodium hydroxide, and potassium hydroxide, an alkali metal carbonate like lithium carbonate, sodium carbonate, potassium carbonate, and cesium carbonate, and sodium hydrogen carbonate. The reaction condition may vary depending on the reaction materials used. However, the reaction is generally carried out at −20 to 100° C., and preferably 15° C. to 80° C., for 5 min to 24 hrs, and preferably for 30 min to 12 hrs to obtain the compound (XI).

The compounds represented by the formula (XI) can be also produced according to Mitsunobu method by using the alcohol compound (X).

The reaction between the compound (VIII) and the alcohol compound (X) may be carried out in a solvent by using a phosphine reagent and an azo reagent or an ethylene dicarboxylic acid reagent, or a phosphonium ylide reagent. The phosphine reagent is not specifically limited, and examples include trialkyl phosphine and triaryl phosphine.

Specific examples include trimethyl phosphine, triethyl phosphine, tripropyl phosphine, triisopropyl phosphine, tributyl phosphine, triisobutyl phosphine, tricyclohexyl phosphine, triphenylphosphine, and diphenylphosphiono polystyrene. The azo reagent is not specifically limited, and examples of the azo reagent that can be used include diethyl azodicarboxylic acid (DEAD), diisopropyl azodicarboxylic acid, 1,1'-(azodicarbonyl)piperidine (ADDP), 1,1'-azobis(N,N'-diisopropylformamide) (TIPA), and 1,6-dimethyl-1,5,7-hexahydro-1,4,6-tetrazocine-2,5-dione (DHAD). The ethylene dicarboxylic acid reagent is not specifically limited, and examples include dimethyl maleate, diethyl maleate, dimethyl fumarate, and diethyl fumarate. The solvent is not specifically limited, and N,N'-dimethylformamide, tetrahydrofuran, dioxane, acetonitrile, propionitrile, nitromethane, acetone, ethyl acetate, isopropyl acetate, benzene, toluene, chlorobenzene, chloroform, dichloromethane, and 1,2-dichloroethane may be used either alone or in combination thereof. The reaction condition may vary depending on the reaction materials used. However, the reaction is generally carried out at 0 to 120° C., and preferably 0° C. to 100° C., for 30 min to 3 days, and preferably for 30 min to 50 hrs to obtain the target compound.

[Process 6] The reaction between the compound (VIII) or the compound (XI) and an azide compound may be carried out in a solvent. The reagents and solvent used for the reaction and the reaction condition are the same as those described in the Process 3 above.

The alkyl halide (IX) and the alcohol compound (X) may be obtained as a commercially available product and used without any processing. Alternatively, they may be appropriately produced according to a method known in the art. Further, among the alkyl halides (IX), the compound represented by the formula (IXa) may be produced according to the method given below, but it is not limited thereto.

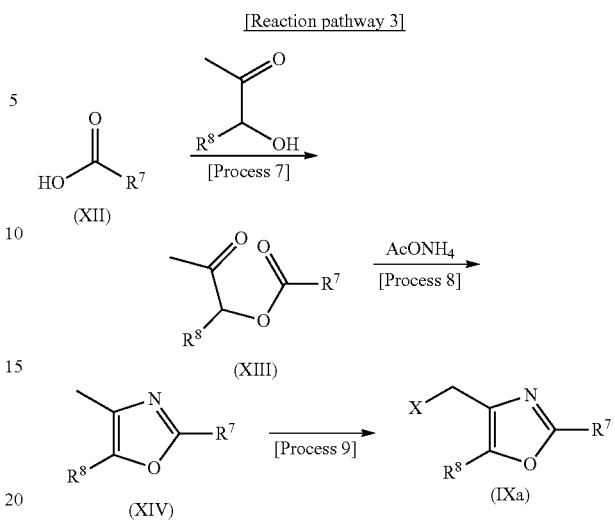

[Reaction pathway 3]

($R^7$ represents a $C_{6-10}$ aryl group or a 5- to 10-membered heteroaryl group, $R^8$ represents a hydrogen atom or a $C_{1-6}$ alkyl group, and X represents a halogen atom).

[Process 7] The dehydration condensation reaction between the compound (XII) and an acetoin compound may be carried out by using a condensation agent in a solvent in the presence or absence of a base and/or a condensation promoting agent. The solvent is not specifically limited, and 1,2-dichloroethane, chloroform, dichloromethane, ethyl acetate, isopropyl acetate, toluene, benzene, tetrahydrofuran, dioxane, acetonitrile, propionitrile, N,N-dimethylformamide, and N-methylpyrrolidone may be used. The base is not specifically limited, and examples thereof include an organic base like pyridine, DMAP, collidine, lutidine, DBU, DBN, DABCO, triethylamine, diisopropylethylamine, diisopropylpentylamine, and trimethylamine, an alkali metal hydride like lithium hydride, sodium hydride, and potassium hydride, an alkali metal hydroxide like lithium hydroxide, sodium hydroxide, and potassium hydroxide, an alkali metal carbonate like lithium carbonate, sodium carbonate, potassium carbonate, and cesium carbonate, and an alkali metal bicarbonate like sodium hydrogen carbonate and potassium hydrogen carbonate. The condensation promoting agent is not specifically limited, and examples of the agent that can be used include DMAP, 1-hydroxy-7-azabenzotriazol (HOAt), 1-hydroxybenzotriazol (HOBt), 3-hydroxy-3,4-dihydro-4-oxo-1, 2,3-benzotriazol (HODhbt), N-hydroxy-5-norbornene-2,3-dicarboxylmide (HONB), pentafluorophenol (HOPfp), N-hydroxyphthalimide (HOPht), and N-hydroxysuccinicimide (HOSu). The condensation agent is not specifically limited, and examples thereof include N,N'-dicyclohexylcarbodiimide (DCC), N,N'-diisopropylcarbodiimide (DIPCI), 1-ethyl-3-(3-dimethylaminopropyl)carbodiimide (WSCI), 1-ethyl-3-(3-dimethylaminopropyl)carbodiimide hydrochloride salt (WSC.HCl), cyano diethyl phosphate (DEPC), benzotriazol-1-yloxy-tris(dimethylamino)phosphonium-hexafluorophosphate (BOP), benzotriazol-1-yloxy-tris(pyrrolidinylamino)phosphoniumhexafluorophosphate (PyBOP), and 2-(1H-benzotriazol-1-yl)-1,1,3,3-tetramethyluronium tetrafluoroborate (TBTU). The reaction condition may vary depending on the reaction materials used. However, the reaction is generally carried out at −20 to 100° C., and preferably 0° C. to 40° C., for 5 min to 30 hrs, and preferably for 2 hrs to 20 hrs to obtain the compound (XIII).

[Process 8] The reaction between the compound (XIII) and ammonium acetate may be carried out in the presence of an acid with or without a solvent. The solvent is not specifically limited, and methanol, ethanol, isopropanol, acetic acid, ethyl acetate, isopropyl acetate, toluene, benzene, dioxane, tetrahydrofuran, acetonitrile, propionitrile, N,N-dimethylformamide, N-methylpyrrolidone, and dimethyl sulfoxide may be used either alone or in combination thereof. The acid is not specifically limited, and the examples thereof include a protonic acid like acetic acid, trifluoroacetic acid, propionic acid, and benzoic acid and Lewis acid like titanium tetrachloride, boron trifluoride, and stannic chloride. When the acid is used, for example acetic acid is used as an acid, it may be also used as a solvent. The reaction condition may vary depending on the reaction materials used. However, the reaction is generally carried out at 0 to 180° C., and preferably 50° C. to 120° C., for 1 min to 24 hrs, and preferably for 5 min to 12 hrs to obtain the compound (XIV).

[Process 9] The halogenation reaction of the compound (XIV) may be carried out in a solvent. The halogenating agent is not specifically limited, and examples thereof include a chlorinating agent, a brominating agent and an iodinating agent like N-chlorosuccinimide (NCS), N-bromosuccinimide (NBS), and N-iodosuccinimide (NIS). As the solvent, 1,2-dichloroethane, chloroform, dichloromethane, diethyl ether, ethyl acetate, isopropyl acetate, toluene, benzene, tetrahydrofuran, dioxane, acetonitrile, and propionitrile may be used either alone or in combination thereof. The reaction condition may vary depending on the reaction materials used. However, the reaction is generally carried out at 0 to 180° C., and preferably 20° C. to 80° C., for 1 min to 24 hrs, and preferably for 5 min to 12 hrs to obtain the compound (IXa).

Preferred examples of $R^7$ group in the above steps include a phenyl group which may have a substituent group, a naphthyl group which may have a substituent group, and a furanyl group which may have a substituent group, and in particular, a 2-furanyl group and the like.

Further, among the compounds (Ia), a compound in which $R^6$ is a lower alkylsulfinyl lower alkyl group is obtained by oxidizing the sulfur atom of the compound (Ia) in which $R^6$ is a lower alkylthio lower alkyl group.

As for the method of oxidation, a general method of converting a sulfur atom to a sulfinyl group or a sulfonyl group can be employed. For example, an oxidation reaction using hydrogen peroxide solution with a catalytic amount of sodium tungstate, molybdenum dichlorodioxide, or tantalum pentachloride, or sodium periodate, potassium periodate, meta-chloroperbenzoic acid (mCPBA), pyridinium chlorochromate (PCC), pyridinium dichromate (PDC), NCS, NBS, NIS, iodine, and bromine, etc. may be used. The solvent is not specifically limited, and water, methanol, ethanol, isopropanol, acetonitrile, acetone, tetrahydrofuran, dichloromethane, chloroform, 1,2-dichloroethane, carbon tetrachloride, N,N-dimethylformamide, and acetic acid may be used either alone or in combination thereof.

Further, the compound (Ia) in which $R^6$ is a lower alkylsulfonyl lower alkyl group can be also produced from a compound (Ia) in which $R^6$ is a lower alkylsulfinyl lower alkyl group with the same oxidation condition.

Further, among the compounds (I), the compound represented by the formula (Ib) can be produced according to the method described below, but it is not limited thereto.

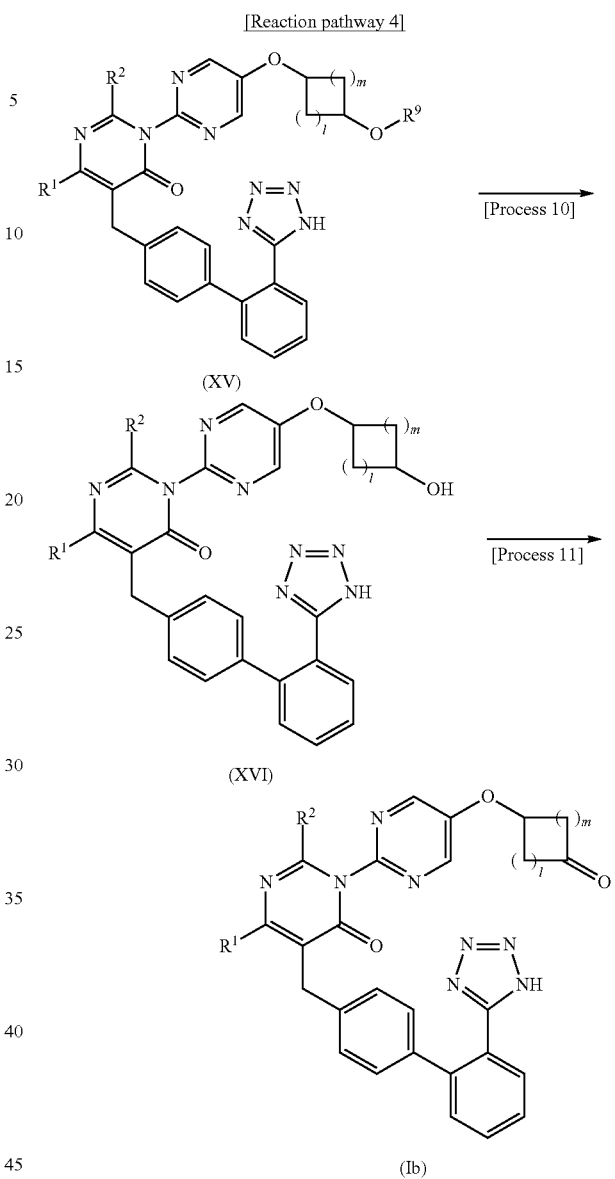

(in the formula, $R^1$ and $R^2$ are as defined above, $R^9$ represents a protecting group, and 1+m represents an integer from 1 to 4).

[Process 10] Deprotection of the protecting group $R^9$ in the compound (XV) is not specifically limited, and it can be carried out with reference to the method that is generally used for deprotection of the protecting group described above (Protective Groups in Organic Synthesis Forth Edition, John Wiley & Sons, Inc).

[Process 11] Oxidation of the compound (XVI) to the compound (Ib) may be carried out according to a method that is commonly used for oxidizing a hydroxyl group to ketone. For example, oxidation condition like Swern oxidation, Moffat oxidation, and Dess-Martin oxidation, or PCC, PDC, manganese dioxide, tetrapropyl ammoniumperruthenate (TPAP) and the like may be used. The solvent is not specifically limited, and tetrahydrofuran, dichloromethane, chloroform, 1,2-dichloroethane, and N,N-dimethylformamide may be used either alone or in combination thereof. The reaction condition may vary depending on the reaction materials used.

However, the reaction is generally carried out at 0 to 180° C., and preferably 20° C. to 100° C., for 1 min to 2 weeks, and preferably for 1 hr to 3 days to obtain the target compound.

Further, among the compounds (I), the compound represented by the formula (Ic) can be produced according to the method described below, but it is not limited thereto.

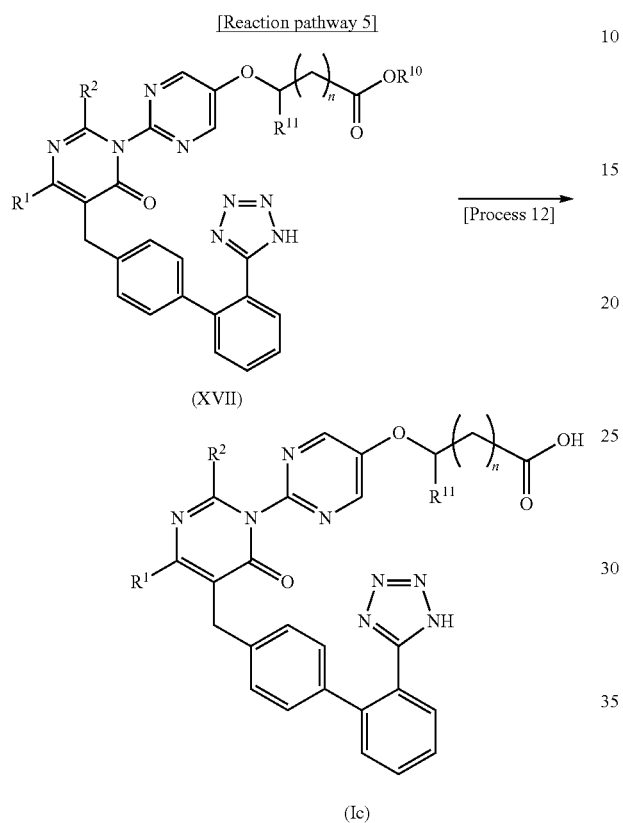

(in the formula, $R^1$ and $R^2$ are as defined above, $R^{10}$ represents a $C_{1-6}$ alkyl group, $R^{11}$ represents a hydrogen atom or a $C_{1-6}$ alkyl group which may have a substituent group, and n represents an integer from 0 to 6).

[Process 12] According to general hydrolysis of the carboxylic acid derivatives (XVII), the compound (Ic) is obtained. The reaction can be carried out in a solvent in the presence of a base or an acid. The solvent is not specifically limited, and tetrahydrofuran, dioxane, methanol, ethanol, and water may be used either alone or in combination thereof. The base is not specifically limited, and examples thereof include an alkali metal hydroxide like sodium hydroxide and potassium hydroxide, an alkali metal carbonate like lithium carbonate, sodium carbonate, potassium carbonate, and cesium carbonate, and potassium trimethylsilyloxide. The acid is not specifically limited, and examples thereof include hydrochloric acid, acetic acid, trifluoroacetic acid, boron tribromide, and aluminum chloride. The reaction condition may vary depending on the reaction materials used. However, the reaction is generally carried out at −20 to 100° C., and preferably 15° C. to 80° C., for 5 min to 1 day, and preferably for 30 min to 13 hrs to obtain the compound (Ic).

Further, among the compounds (I), the compound represented by the formula (Id) can be produced according to the method described below, but it is not limited thereto.

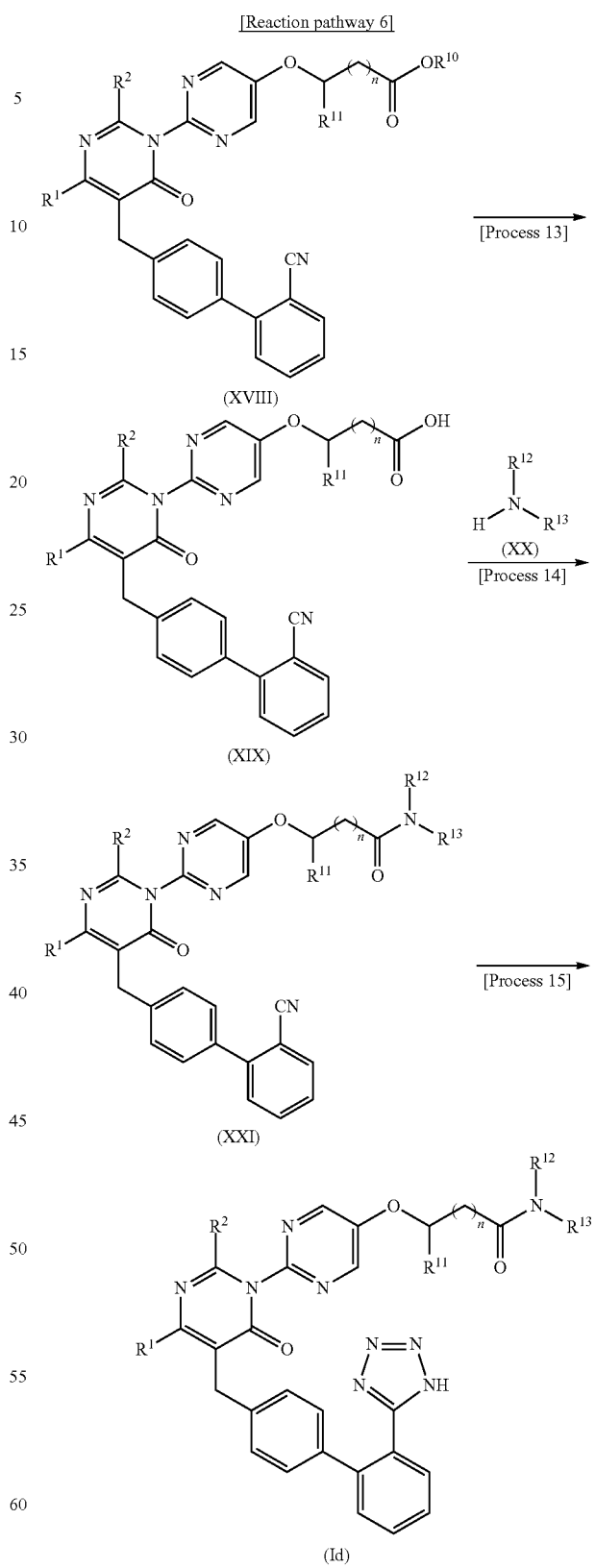

(in the formula, $R^1$, $R^2$, $R^{10}$, $R^{11}$, and n are as defined above, $R^{12}$ and $R^{13}$, which may be the same or different from each other, represent a hydrogen atom or a $C_{1-6}$ alkyl group).

[Process 13] According to general hydrolysis of the carboxylic acid derivatives (XVIII), the compound (XIX) is obtained. The reagents and solvent used for the reaction and the reaction condition are the same as those described in the Process 12 above.

[Process 14] The dehydration condensation reaction between the carboxylic acid compound (XIX) and the amine compound (XX) may be carried out using a condensation agent in a solvent in the presence or absence of a base and/or a condensation-promoting agent. The solvent is not specifically limited, and 1,2-dichloroethane, chloroform, dichloromethane, ethyl acetate, isopropyl acetate, toluene, benzene, tetrahydrofuran, dioxane, acetonitrile, propionitrile, N,N-dimethylformamide, or N-methylpyrrolidone may be used. The base is not specifically limited, and examples thereof include an organic base like pyridine, DMAP, collidine, lutidine, DBU, DBN, DABCO, triethylamine, diisopropylethylamine, diisopropylpentylamine, and trimethylamine, an alkali metal hydride like lithium hydride, sodium hydride, and potassium hydride, an alkali metal hydroxide like lithium hydroxide, sodium hydroxide, and potassium hydroxide, an alkali metal carbonate like lithium carbonate, sodium carbonate, potassium carbonate, and cesium carbonate, and an alkali metal bicarbonate like sodium hydrogen carbonate and potassium hydrogen carbonate. The condensation promoting agent is not specifically limited, and examples thereof include DMAP, HOAt, HOBt, HODhbt, HONB, HOPfp, HOPht, and HOSu. The condensation agent is not specifically limited, and examples thereof include DCC, DIPCI, WSCI, WSC.HCl, DEPC, BOP, PyBOP, and TBTU. The reaction condition may vary depending on the reaction materials used. However, the reaction is generally carried out at −20 to 100° C., and preferably 0° C. to 40° C., for 5 min to 30 hrs, and preferably for 2 hrs to 20 hrs to obtain the compound (XXI). Further, the carboxylic acid compound (XIX) used for the reaction may be first derivatized to an acid halide, and then reacted with the amine compound (XX).

[Process 15] The reaction between the compound (XXI) and an azide compound may be carried out in a solvent. The reagents and solvent used for the reaction and the reaction condition are the same as those described in the Process 3 above.

Further, among the compounds (I), the compound represented by the formula (Ie) can be produced according to the method described below, but it is not limited thereto.

[Reaction pathway 7]

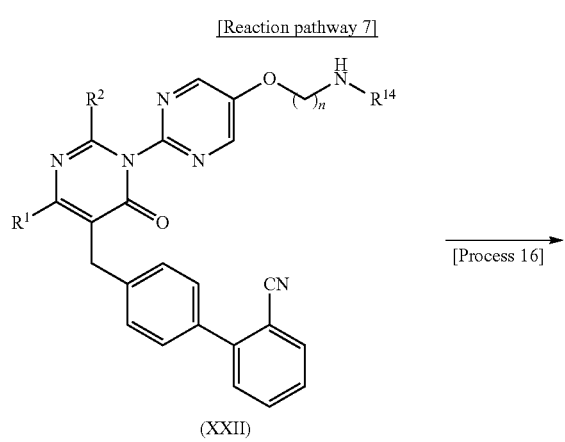

(XXII)

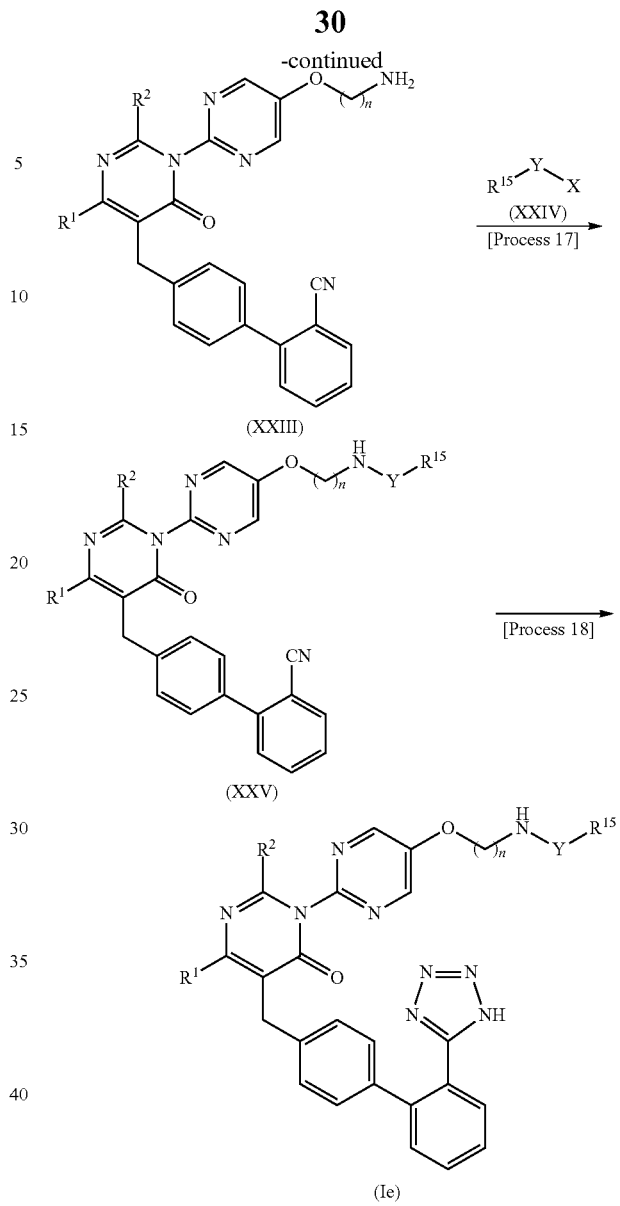

(in the formula, $R^1$, $R^2$, and n are as defined above, $R^{14}$ represents a protecting group for an amino group, $R^{15}$ represents a $C_{1-6}$ alkyl group which may have a substituent group, X represents a halogen atom, and Y represents —CO— or —SO$_2$—).

[Process 16] Deprotection of the protecting group $R^{14}$ in the compound (XXII) is not specifically limited, and it can be carried out with reference to the method that is generally used for deprotection of the protecting group (Protective Groups in Organic Synthesis Forth Edition, John Wiley & Sons, Inc). The protecting group is not specifically limited, and the examples thereof that can be used include a benzyl group, a 9-fluorenylmethyloxycarbonyl group (Fmoc group), a 2,2,2-trichloroethyloxycarbonyl group (Troc group), a 2-trimethylsilylethyloxycarbonyl (Teoc group), a t-butyloxycarbonyl group (Boc group), an allyloxycarbonyl group (Alloc group), a vinyloxycarbonyl group, a benzyloxycarbonyl group (Cbz group), a p-methoxybenzyloxycarbonyl group, a p-nitrobenzyloxycarbonyl group, an allyl group, a [2-(trimethylsilyl)ethoxy]methyl group (SEM group), a 4-methoxybenzyl group, a triphenylmethyl group, a benzenesulfonyl group, and an o-nitrobenzenesulfonyl group. In particular, a Boc group, a Fmoc group, and a Cbz group are preferable.

[Process 17] The condensation reaction between the amine compound (XXIII) and the acid halide (XXIV) may be carried out in a solvent in the presence or absence of a base. The solvent is not specifically limited, and tetrahydrofuran, toluene, dioxane, N,N-dimethylformamide, N-methylpyrrolidone, dichloromethane, chloroform, acetonitrile, and propionitrile may be used either alone or in combination thereof. The base is not specifically limited, and examples thereof include an organic base like pyridine, DMAP, collidine, lutidine, DBU, DBN, DABCO, triethylamine, diisopropylamine, diisopropylpentylamine, and trimethylamine, an alkali metal hydride like lithium hydride, sodium hydride, and potassium hydride, an alkali metal hydroxide like lithium hydroxide, sodium hydroxide, and potassium hydroxide, an alkali metal carbonate like lithium carbonate, sodium carbonate, potassium carbonate, and cesium carbonate, and sodium hydrogen carbonate. The reaction condition may vary depending on the reaction materials used. However, the reaction is generally carried out at −20 to 100° C., and preferably 15° C. to 80° C., for 5 min to 24 hrs, and preferably for 5 hrs to 12 hrs to obtain the amide derivative (XXV).

[Process 18] The reaction between the amide derivative (XXV) and an azide compound may be carried out in a solvent. The reagents and solvent used for the reaction and the reaction condition are the same as those described in the Process 3 above.

If necessary, the intermediates and target compounds that are obtained from the each reaction above can be isolated and purified by a purification method that is generally used in a field of organic synthesis chemistry, e.g., filtration, extraction, washing, drying, concentration, re-crystallization, and various chromatographic methods. Furthermore, the intermediates may be used for the next reaction without any specific purification.

Various isomers may be isolated by applying a general method based on a difference in physicochemical properties among the isomers. For example, a racemic mixture may be resolved into an optically pure isomer by common racemic resolution like optical resolution by which a diastereomer salt is formed with a common optically active acid like tartaric acid or a method of using optically active column chromatography. Further, a mixture of diastereomers can be resolved by fractional crystallization or various chromatographic methods, for example. Furthermore, an optically active compound can be also produced by using an appropriate starting compound that is optically active.

The compound (I) obtained may be converted into a salt according to a common method. Furthermore, it may be converted into a solvate with a solvent like a solvent for reaction or a solvent for re-crystallization, or into a hydrate.

Examples of dosage form of the pharmaceutical agent containing the compounds of the invention, salts or solvates thereof as an effective component include, for example, those for oral administration such as tablet, capsule, granule, powder or syrup, and those for parenteral administration such as intravenous injection, intramuscular injection, suppository, inhalant, transdermal preparation, eye drop or nasal drop. In order to prepare a pharmaceutical preparation in the various dosage forms, the effective component may be used alone, or may be used in appropriate combination with other pharmaceutically acceptable carriers such as excipients, binders, extending agents, disintegrating agents, surface active agents, lubricants, dispersing agents, buffering agents, preservatives, corrigents, perfumes, coating agents and diluents to give a pharmaceutical composition.

Although the administration amount of the pharmaceutical agent of the invention may vary depending on the weight, age, sex, symptoms and the like of a patient, in terms of the compound represented by the formula (I), generally 0.1 to 1000 mg, especially 1 to 300 mg, may be administered orally or parenterally at one time or several times as divided portions per day for an adult.

EXAMPLES

Hereinbelow, the invention will be explained in greater detail with reference to examples. However, the invention is not limited to these examples. The abbreviations used in the examples have the following meanings.
s: singlet
d: doublet
t: triplet
q: quartet
m: multiplet
br: broad
J: coupling constant
Hz: hertz
$CDCl_3$: deuterated chloroform
$CD_3OD$: deuterated methanol
$d_6$-DMSO: deuterated dimethyl sulfoxide
$^1$H-NMR: proton nuclear magnetic resonance
IR: infrared absorption spectrum Example 1

Production of 5-{[2'-(1H-tetrazol-5-yl)biphenyl-4-yl]methyl}-6-butyl-2-methyl-3-(pyridin-2-yl)pyrimidin-4(3H)-one

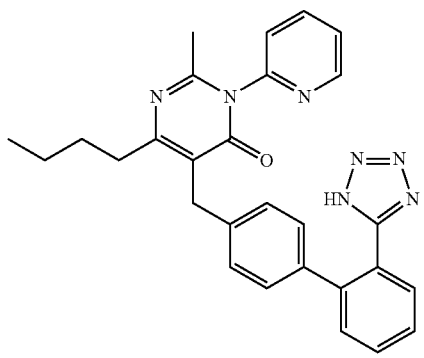 [SMILES: CCCCc1nc(C)n(-c2ccccn2)c(=O)c1Cc1ccc(-c2ccccc2-c2nnn[nH]2)cc1]

Process 1: The toluene (40.5 mL)-acetic acid (4.5 mL) solution of methyl 2-[(2'-cyanobiphenyl-4-yl)methyl]-3-oxoheptanoate (2.11 g, 6.04 mmol), which has been synthesized according to the method described in Journal of Medicinal Chemistry, 38 (24), 4806 (1995), and ammonium acetate (2.79 g, 36.2 mmol) was refluxed for 4 hrs under heating. The solvent was distilled off and the resulting residues were added acetic anhydride (4.5 mL) and acetic acid (1.0 mL) at room temperature, and stirred at 70° C. for 3 hrs. The reaction mixture was added water under ice cooling and extracted with ethyl acetate. The organic layer was combined, washed with water and brine, dried over anhydrous sodium sulfate, and concentrated in vacuo. The residues obtained were subjected to silica gel column chromatography (hexane/ethyl acetate) to obtain methyl(Z)-3-acetamide-2-[(2'-cyanobiphenyl-4-yl)methyl]heptanoate (1.29 g, 55%) as a pale yellow oil.

$^1$H-NMR (CDCl$_3$) δ:
0.89 (3H, t, J=7 Hz), 1.28-1.55 (4H, m), 2.17 (3H, s), 2.92 (2H, t, J=8 Hz), 3.70 (3H, s), 3.76 (2H, s), 7.25 (2H, d, J=8 Hz), 7.42 (1H, t, J=8 Hz), 7.45-7.53 (3H, m), 7.63 (1H, t, J=8 Hz), 7.74 (1H, d, J=8 Hz), 11.9 (1H, s).

Process 2: Under argon atmosphere, trimethyl aluminum (2 mol/L heptane solution, 1.53 mL, 3.1 mmol) was added to 1,2-dichloroethane (8 mL) solution of 2-aminopyridine (288 mg, 3.1 mmol) at room temperature, and stirred at the same temperature for 75 min. 1,2-Dichloroethane (10 mL) solution of methyl(Z)-3-acetamide-2-[(2'-cyanobiphenyl-4-yl)methyl]heptanoate (400 mg, 1.02 mmol) was added dropwise thereto at room temperature followed by reflux for 12 hrs under heating. An aqueous solution of ammonium chloride and chloroform were added to the reaction mixture, which was then filtered through a pad of celite. The organic layer in the filtrate was separated, and the aqueous layer was extracted with chloroform. The organic layer was combined, washed with water and brine, dried over anhydrous sodium sulfate, and concentrated in vacuo. The residues obtained were subjected to silica gel column chromatography (hexane/acetone) to obtain 4'-{[4-butyl-2-methyl-6-oxo-1-(pyridin-2-yl)-1,6-dihydropyrimidin-5-yl]methyl}biphenyl-2-carbonitrile (337 mg, 76%) as a pale yellow amorphous.

$^1$H-NMR (CDCl$_3$) δ:

0.94 (3H, t, J=7 Hz), 1.33-1.47 (2H, m), 1.53-1.66 (2H, m), 2.17 (3H, s), 2.67 (2H, t, J=8 Hz), 3.98 (2H, s), 7.33-7.51 (8H, m), 7.61 (1H, td, J=8, 2 Hz), 7.74 (1H, dd, J=8, 2 Hz), 7.92 (1H, td, J=8, 2 Hz), 8.67 (1H, dt, J=5, 1 Hz).

Process 3: To the toluene (3 mL) solution of 4'-{[4-butyl-2-methyl-6-oxo-1-(pyridin-2-yl)-1,6-dihydropyrimidin-5-yl]methyl}biphenyl-2-carbonitrile (335 mg, 0.77 mmol), trimethylsilylazide (2.64 g, 22.9 mmol) and dibutyltin oxide (96 mg, 0.386 mmol) were added, and stirred at 80° C. for 24 hrs under argon atmosphere. The reaction solvent was distilled off and the resulting residues were separated and purified by silica gel column chromatography (chloroform:methanol=100:1) to obtain the target compound (224 mg, 61%) as a pale yellow amorphous.

$^1$H-NMR (d$_6$-DMSO) δ:

0.76 (3H, t, J=7 Hz), 1.13-1.27 (2H, m), 1.33-1.44 (2H, m), 1.92 (3H, s), 2.43 (2H, t, J=8 Hz), 3.72 (2H, s), 6.89 (2H, d, J=8 Hz), 7.05 (2H, d, J=8 Hz), 7.34-7.57 (6H, m), 7.97 (1H, td, J=8, 2 Hz), 8.52-8.57 (1H, m).

Example 2

Production of 5-{[2'-(1H-tetrazol-5-yl)biphenyl-4-yl]methyl}-6-butyl-2-methyl-3-(5-methylpyridin-2-yl)pyrimidin-4(3H)-one

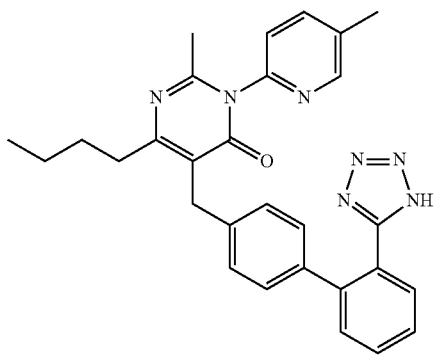 [SMILES: CCCCc1nc(C)n(-c2ccc(C)cn2)c(=O)c1Cc1ccc(-c2ccccc2-c2nnn[nH]2)cc1]

4'-{[4-butyl-2-methyl-1-(5-methylpyridin-2-yl)-6-oxo-1,6-dihydropyrimidin-5-yl]methyl}biphenyl-2-carbonitrile was obtained according to the same reaction and treatment as the Process 2 of Example 1 by using 2-amino-5-methylpyridine instead of 2-aminopyridine.

$^1$H-NMR (CDCl$_3$) δ:

0.93 (3H, t, J=7 Hz), 1.31-1.49 (2H, m), 1.51-1.71 (2H, m), 2.17 (3H, s), 2.42 (3H, s), 2.66 (2H, t, J=8 Hz), 3.97 (2H, s), 7.26 (1H, d, J=8 Hz), 7.34-7.56 (6H, m), 7.61 (1H, td, J=8, 2 Hz), 7.66-7.80 (2H, m), 8.48 (1H, d, J=2 Hz).

The target compound was obtained according to the same reaction and treatment as the Process 3 of Example 1 by using 4'-{[4-butyl-2-methyl-1-(5-methylpyridin-2-yl)-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CD$_3$OD) δ:

0.90 (3H, t, J=7 Hz), 1.29-1.43 (2H, m), 1.46-1.59 (2H, m), 2.12 (3H, s), 2.45 (3H, s), 2.60 (2H, t, J=8 Hz), 3.91 (2H, s), 7.02 (2H, d, J=8 Hz), 7.18 (2H, d, J=8 Hz), 7.40 (1H, d, J=8 Hz), 7.52 (2H, t, J=7 Hz), 7.57-7.67 (2H, m), 7.89 (1H, dd, J=8, 2 Hz), 8.48 (1H, d, J=2 Hz).

Example 3

Production of 5-{[2'-(1H-tetrazol-5-yl)biphenyl-4-yl]methyl}-6-butyl-3-(5-methoxypyridin-2-yl)-2-methylpyrimidin-4(3H)-one

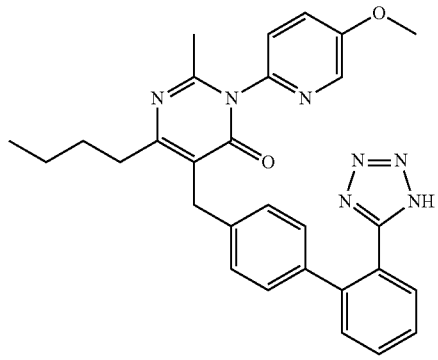

4'-{[4-butyl-1-(5-methoxypyridin-2-yl)-2-methyl-6-oxo-1,6-dihydropyrimidin-5-yl]methyl}biphenyl-2-carbonitrile was obtained according to the same reaction and treatment as the Process 2 of Example 1 by using 2-amino-5-methoxypyridine instead of 2-aminopyridine.

$^1$H-NMR (CDCl$_3$) δ:

0.93 (3H, t, J=7 Hz), 1.33-1.49 (2H, m), 1.53-1.66 (2H, m), 2.17 (3H, s), 2.66 (2H, t, J=8 Hz), 3.92 (3H, s), 3.97 (2H, s), 7.29 (1H, d, J=8 Hz), 7.33-7.54 (8H, m), 7.61 (1H, td, J=8, 2 Hz), 7.74 (1H, dd, J=8, 2 Hz), 8.30 (1H, d, J=3 Hz).

The target compound was obtained according to the same reaction and treatment as the Process 3 of Example 1 by using 4'-{[4-butyl-1-(5-methoxypyridin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.96 (3H, t, J=7 Hz), 1.35-1.52 (2H, m), 1.58-1.73 (2H, m), 2.17 (3H, S), 2.69 (2H, t, J=8 Hz), 3.92 (5H, s), 7.11 (2H, d, J=8 Hz), 7.20-7.32 (3H, m), 7.33-7.45 (2H, m), 7.47-7.61 (2H, m), 8.15 (1H, d, J=8 Hz), 8.26 (1H, d, J=3 Hz).

Example 4

Production of 5-{[2'-(1H-tetrazol-5-yl)biphenyl-4-yl]methyl}-6-butyl-3-(3-fluoropyridin-2-yl)-2-methylpyrimidin-4(3H)-one

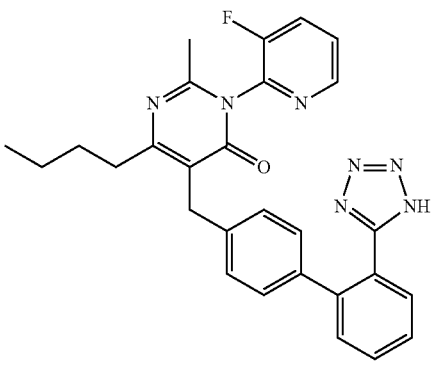 [SMILES: CCCCc1nc(C)n(-c2ncccc2F)c(=O)c1Cc1ccc(-c2ccccc2-c2nnn[nH]2)cc1]

4'-{[4-butyl-1-(3-fluoropyridin-2-yl)-2-methyl-6-oxo-1,6-dihydropyrimidin-5-yl]methyl}biphenyl-2-carbonitrile was obtained according to the same reaction and treatment as the Process 2 of Example 1 by using 2-amino-3-fluoropyridine instead of 2-aminopyridine.

$^1$H-NMR (CDCl$_3$) δ:
0.93 (3H, t, J=7 Hz), 1.40 (2H, sextet, J=8 Hz), 1.55-1.66 (2H, m), 2.19 (3H, s), 2.63-2.67 (2H, m), 3.99 (2H, s), 7.37-7.52 (7H, m), 7.59-7.66 (2H, m), 7.74 (1H, d, J=7 Hz), 8.48 (1H, d, J=5 Hz).

The target compound was obtained according to the same reaction and treatment as the Process 3 of Example 1 by using 4'-{[4-butyl-1-(3-fluoropyridin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.95 (3H, t, J=7 Hz), 1.43 (2H, sextet, J=8 Hz), 1.63-1.70 (2H, m), 2.19 (3H, s), 2.66-2.70(2H, m), 3.93 (2H, s), 7.10 (2H, d, J=8 Hz), 7.25 (2H, d, J=8 Hz), 7.40-7.69 (5H, m), 8.12 (1H, d, J=8 Hz), 8.45 (1H, d, J=5 Hz).

Example 5

Production of 5-{[2'-(1H-tetrazol-5-yl)biphenyl-4-yl]methyl}-6-butyl-3-(5-fluoropyridin-2-yl)-2-methylpyrimidin-4(3H)-one

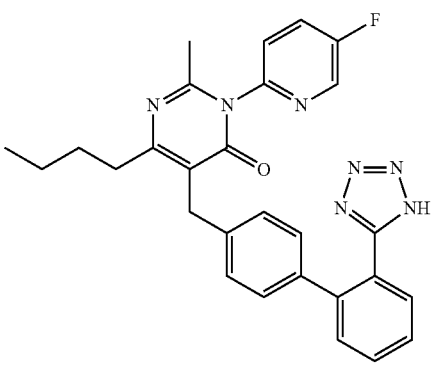 [SMILES: CCCCc1nc(C)n(-c2ccc(F)cn2)c(=O)c1Cc1ccc(-c2ccccc2-c2nnn[nH]2)cc1]

4'-{[4-butyl-1-(5-fluoropyridin-2-yl)-2-methyl-6-oxo-1,6-dihydropyrimidin-5-yl]methyl}biphenyl-2-carbonitrile was obtained according to the same reaction and treatment as the Process 2 of Example 1 by using 2-amino-5-fluoropyridine instead of 2-aminopyridine.

$^1$H-NMR (CDCl$_3$) δ:
0.94 (3H, t, J=7 Hz), 1.41 (2H, sextet, J=8 Hz), 1.52-1.68 (2H, m), 2.17 (3H, s), 2.65-2.69 (2H, m), 3.97 (2H, s), 7.34-7.50 (7H, m), 7.60-7.66 (2H, m), 7.74 (1H, dd, J=8, 1 Hz), 8.51 (1H, d, J=3 Hz).

The target compound was obtained according to the same reaction and treatment as the Process 3 of Example 1 by using 4'-{[4-butyl-1-(5-fluoropyridin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.95 (3H, t, J=7 Hz), 1.43 (2H, sextet, J=8 Hz), 1.63-1.70 (2H, m), 2.18 (3H, s), 2.66-2.70 (2H, m), 3.90 (2H, s), 7.08 (2H, d, J=8 Hz), 7.22 (2H, d, J=8 Hz), 7.30-7.67 (4H, m), 7.87 (1H, d, J=2 Hz), 8.09 (1H, d, J=8 Hz), 8.48 (1H, d, J=3 Hz).

Example 6

Production of 5-{[2'-(1H-tetrazol-5-yl)biphenyl-4-yl]methyl}-6-butyl-3-(3-chloropyridin-2-yl)-2-methylpyrimidin-4(3H)-one

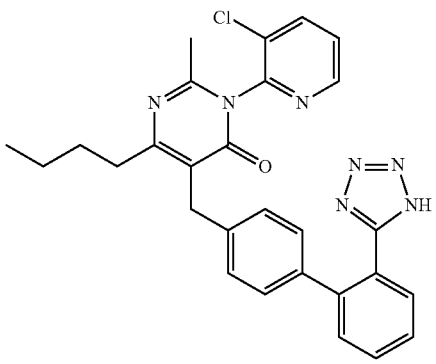 [SMILES: CCCCc1nc(C)n(-c2ncccc2Cl)c(=O)c1Cc1ccc(-c2ccccc2-c2nnn[nH]2)cc1]

4'-{[4-butyl-1-(3-chloropyridin-2-yl)-2-methyl-6-oxo-1,6-dihydropyrimidin-5-yl]methyl}biphenyl-2-carbonitrile was obtained according to the same reaction and treatment as the Process 2 of Example 1 by using 2-amino-3-chloropyridine instead of 2-aminopyridine.

$^1$H-NMR (CDCl$_3$) δ:
0.93 (3H, t, J=7 Hz), 1.40 (2H, sextet, J=8 Hz), 1.56-1.64 (2H, m), 2.14 (3H, s), 2.59-2.71 (2H, m), 3.96 (1H, d, J=15 Hz), 4.04 (1H, d, J=15 Hz), 7.36-7.48 (7H, m), 7.61 (1H, m), 7.74 (1H, dd, J=8, 1 Hz), 7.95(1H, dd, J=8, 1 Hz), 8.58(1H, dd, J=5, 2 Hz).

The target compound was obtained according to the same reaction and treatment as the Process 3 of Example 1 by using 4'-{[4-butyl-1-(3-chloropyridin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.96 (3H, t, J=7 Hz), 1.45 (2H, sextet, J=8 Hz), 1.64-1.72 (2H, m), 2.14 (3H, s), 2.67-2.72 (2H, m), 3.56 (2H, s), 7.12 (2H, d, J=8 Hz), 7.29 (2H, d, J=8 Hz), 7.42-7.59 (4H, m), 7.95 (1H, dd, J=8, 2 Hz), 8.17 (1H, d, J=8 Hz), 8.56 (1H, dd, J=5, 2 Hz).

Example 7

Production of 5-{[2'-(1H-tetrazol-5-yl)biphenyl-4-yl]methyl}-6-butyl-3-(5-chloropyridin-2-yl)-2-methylpyrimidin-4(3H)-one

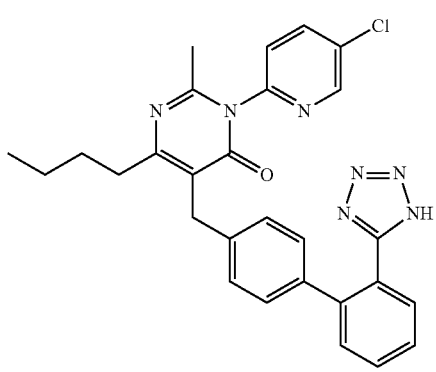 [SMILES: CCCCc1nc(C)n(-c2ccc(Cl)cn2)c(=O)c1Cc1ccc(-c2ccccc2-c2nnn[nH]2)cc1]

4'-{[4-butyl-1-(5-chloropyridin-2-yl)-2-methyl-6-oxo-1,6-dihydropyrimidin-5-yl]methyl}biphenyl-2-carbonitrile was obtained according to the same reaction and treatment as the Process 2 of Example 1 by using 2-amino-5-chloropyridine instead of 2-aminopyridine.

¹H-NMR (CDCl₃) δ:
0.94 (3H, t, J=7 Hz), 1.41 (2H, sextet, J=8 Hz), 1.57-1.65 (2H, m), 2.18 (3H, s), 2.65-2.69 (2H, m), 3.96 (2H, s), 7.35-7.48 (7H, m), 7.62 (1H, m), 7.74 (1H, dd, J=8, 1 Hz), 7.89 (1H, dd, J=8, 3 Hz), 8.62(1H, dd, J=8, 2 Hz).

The target compound was obtained according to the same reaction and treatment as the Process 3 of Example 1 by using 4'-{[4-butyl-1-(5-chloropyridin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.95 (3H, t, J=7 Hz), 1.42 (2H, sextet, J=8 Hz), 1.62-1.69 (2H, m), 2.17 (3H, s), 2.65-2.69 (2H, m), 3.89 (2H, s), 7.07 (2H, d, J=8 Hz), 7.22 (2H, d, J=8 Hz), 7.28-7.60 (4H, m), 7.84 (1H, dd, J=8, 2 Hz), 8.08 (1H, d, J=8 Hz), 8.56 (1H, d, J=2 Hz).

Example 8

Production of 5-{[2'-(1H-tetrazol-5-yl)biphenyl-4-yl]methyl}-3-(6-bromopyridin-2-yl)-6-butyl-2-methylpyrimidin-4(3H)-one

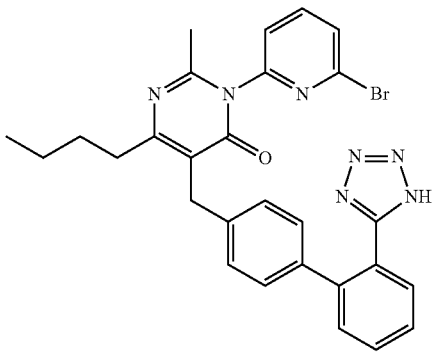 [SMILES: CCCCc1nc(C)n(-c2cccc(Br)n2)c(=O)c1Cc1ccc(-c2ccccc2-c2nnn[nH]2)cc1]

4'-{[1-(6-bromopyridin-2-yl)-4-butyl-2-methyl-6-oxo-1,6-dihydropyrimidin-5-yl]methyl}biphenyl-2-carbonitrile was obtained according to the same reaction and treatment as the Process 2 of Example 1 by using 2-amino-6-bromopyridine instead of 2-aminopyridine.

¹H-NMR (CDCl₃) δ:
0.94 (3H, t, J=7 Hz), 1.41 (2H, sextet, J=8 Hz), 1.55-1.68 (2H, m), 2.21 (3H, s), 2.64-2.68 (2H, m), 3.95 (2H, s), 7.37-7.49 (7H, m), 7.60-7.64 (2H, m), 7.73-7.80 (2H, m).

The target compound was obtained according to the same reaction and treatment as the Process 3 of Example 1 by using 4'-{[1-(6-bromopyridin-2-yl)-4-butyl-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.94 (3H, t, J=7 Hz), 1.42 (2H, sextet, J=8 Hz), 1.59-1.67 (2H, m), 2.18 (3H, s), 2.63-2.67(2H, m), 3.86 (2H, s), 7.04 (2H, d, J=8 Hz), 7.18 (2H, d, J=8 Hz), 7.30-7.60 (5H, m), 7.75 (1H, t, J=8 Hz), 8.01 (1H, dd, J=8, 1 Hz).

Example 9

5-{[2'-(1H-tetrazol-5-yl)biphenyl-4-yl]methyl}-6-butyl-2-methyl-3-[3-(trifluoromethyl)pyridin-2-yl]pyrimidin-4(3H)-one

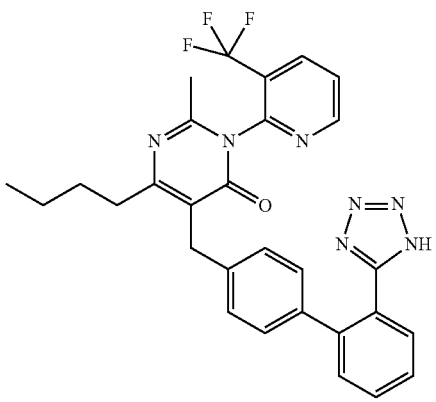 [SMILES: CCCCc1nc(C)n(-c2ncccc2C(F)(F)F)c(=O)c1Cc1ccc(-c2ccccc2-c2nnn[nH]2)cc1]

4'-{{4-butyl-2-methyl-6-oxo-1-[3-(trifluoromethyl)pyridin-2-yl]-1,6-dihydropyrimidin-5-yl}methyl}biphenyl-2-carbonitrile was obtained according to the same reaction and treatment as the Process 2 of Example 1 by using 2-amino-3-(trifluoromethyl)pyridine instead of 2-aminopyridine.

¹H-NMR (CDCl₃) δ:
0.93 (3H, t, J=7 Hz), 1.39 (2H, sextet, J=8 Hz), 1.57-1.66 (2H, m), 2.11 (3H, s), 2.60-2.68 (2H, m), 3.91 (1H, d, J=15 Hz), 4.05(1H, d, J=15 Hz), 7.34-7.49(6H, m), 7.59-7.64(2H, m), 7.74(1H, dd, J=7, 1 Hz), 8.22(1H, dd, J=8, 2 Hz), 8.88 (1H, d, J=5 Hz).

The target compound was obtained according to the same reaction and treatment as the Process 3 of Example 1 by using 4'-{{4-butyl-2-methyl-6-oxo-1-[3-(trifluoromethyl)pyridin-2-yl]-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.92 (3H, t, J=7 Hz), 1.32-1.43 (2H, m), 1.57-1.63 (2H, m), 2.09 (3H, s), 2.54-2.67(2H, m), 3.83 (1H, d, J=15 Hz), 3.91 (1H, d, J=15 Hz), 7.07 (2H, d, J=8 Hz), 7.17 (2H, d, J=8 Hz), 7.37-7.70(5H, m), 8.20 (1H, d, J=6 Hz), 8.85 (1H, d, J=3 Hz).

Example 10

Production of 5-{[2'-(1H-tetrazol-5-yl)biphenyl-4-yl]methyl}-6-butyl-2-methyl-3-[4-(trifluoromethyl)pyridin-2-yl]pyrimidin-4(3H)-one

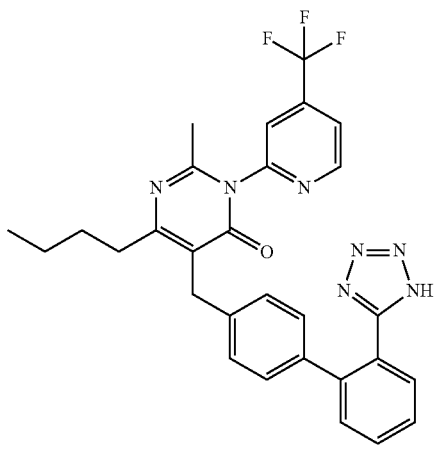 [SMILES: CCCCc1nc(C)n(-c2cc(C(F)(F)F)ccn2)c(=O)c1Cc1ccc(-c2ccccc2-c2nnn[nH]2)cc1]

4'-{{4-butyl-2-methyl-6-oxo-1-[4-(trifluoromethyl)pyridin-2-yl]-1,6-dihydropyrimidin-5-yl}methyl}biphenyl-2-carbonitrile was obtained according to the same reaction and treatment as the Process 2 of Example 1 by using 2-amino-4-(trifluoromethyl)pyridine instead of 2-aminopyridine.

¹H-NMR (CDCl₃) δ:
0.94 (3H, t, J=7 Hz), 1.41 (2H, sextet, J=8 Hz), 1.58-1.66 (2H, m), 2.18 (3H, s), 2.66-2.70 (2H, m), 3.98 (2H, s), 7.38-7.48(6H, m), 7.60-7.66 (3H, m), 7.74(1H, dd, J=8, 2 Hz), 8.86(1H, dd, J=6, 3 Hz).

The target compound was obtained according to the same reaction and treatment as the Process 3 of Example 1 by using 4'-{{4-butyl-2-methyl-6-oxo-1-[4-(trifluoromethyl)pyridin-2-yl]-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.95 (3H, t, J=8 Hz), 1.42 (2H, sextet, J=7 Hz), 1.62-1.70 (2H, m), 2.17 (3H, s), 2.67-2.71(2H, m), 3.93 (2H, s), 7.11 (2H, d, J=8 Hz), 7.28 (2H, d, J=8 Hz), 7.40 (1H, dd, J=8, 1 Hz), 7.50-7.67(4H, m), 8.15 (1H, dd, J=1, 8 Hz), 8.44 (1H, d, J=5 Hz).

Example 11

Production of 5-{[2'-(1H-tetrazol-5-yl)biphenyl-4-yl]methyl}-6-butyl-2-methyl-3-[5-(trifluoromethyl)pyridin-2-yl]pyrimidin-4(3H)-one

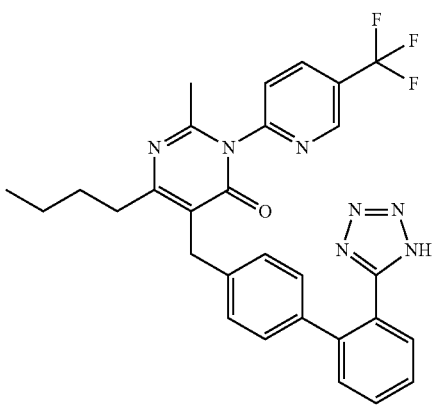 [SMILES: CCCCc1nc(C)n(-c2ccc(C(F)(F)F)cn2)c(=O)c1Cc1ccc(-c2ccccc2-c2nnn[nH]2)cc1]

4'-{{4-butyl-2-methyl-6-oxo-1-[5-(trifluoromethyl)pyridin-2-yl]-1,6-dihydropyrimidin-5-yl}methyl}biphenyl-2-carbonitrile was obtained according to the same reaction and treatment as the Process 2 of Example 1 by using 2-amino-5-(trifluoromethyl)pyridine instead of 2-aminopyridine.

¹H-NMR (CDCl₃) δ:
0.95 (3H, t, J=7 Hz), 1.42 (2H, sextet, J=8 Hz), 1.58-1.66 (2H, m), 2.19 (3H, s), 2.67-2.71 (2H, m), 3.97 (2H, s), 7.38-7.64 (8H, m), 7.75 (1H, dd, J=8, 1 Hz), 8.17 (1H, dd, J=8, 3 Hz), 8.95(1H, s).

The target compound was obtained according to the same reaction and treatment as the Process 3 of Example 1 by using 4'-{{4-butyl-2-methyl-6-oxo-1-[5-(trifluoromethyl)pyridin-2-yl]-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.95 (3H, t, J=7 Hz), 1.44 (2H, sextet, J=8 Hz), 1.64-1.72 (2H, m), 2.18 (3H, s), 2.68-2.72 (2H, m), 3.92 (2H, s), 7.10 (2H, d, J=8 Hz), 7.27 (2H, d, J=8 Hz), 7.40-7.60 (4H, m), 8.12-8.18 (2H, m), 8.91 (1H, s).

Example 12

Production of 5-{[2'-(1H-tetrazol-5-yl)biphenyl-4-yl]methyl}-6-butyl-2-methyl-3-[6-(trifluoromethyl)pyridin-2-yl]pyrimidin-4(3H)-one

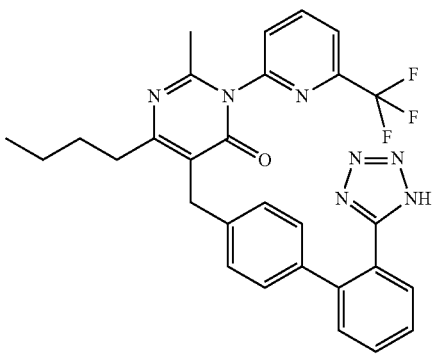 [SMILES: CCCCc1nc(C)n(-c2cccc(C(F)(F)F)n2)c(=O)c1Cc1ccc(-c2ccccc2-c2nnn[nH]2)cc1]

4'-{{4-butyl-2-methyl-6-oxo-1-[6-(trifluoromethyl)pyridin-2-yl]-1,6-dihydropyrimidin-5-yl}methyl}biphenyl-2-carbonitrile was obtained according to the same reaction and treatment as the Process 2 of Example 1 by using 2-amino-6-(trifluoromethyl)pyridine instead of 2-aminopyridine.

$^1$H-NMR (CDCl$_3$) δ:
0.95 (3H, t, J=7 Hz), 1.42 (2H, sextet, J=8 Hz), 1.57-1.65 (2H, m), 2.20 (3H, s), 2.66-2.70 (2H, m), 3.97 (2H, s), 7.35-7.52(6H, m), 7.60-7.64 2H, m), 7.75(1H, d, J=8 Hz), 7.82 (1H, d, J=8 Hz), 8.11 (1H, t, J=8 Hz).

The target compound was obtained according to the same reaction and treatment as the Process 3 of Example 1 by using 4'-{{4-butyl-2-methyl-6-oxo-1-[6-(trifluoromethyl)pyridin-2-yl]-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.96 (3H, t, J=7 Hz), 1.44 (2H, sextet, J=7 Hz), 1.64-1.71 (2H, m), 2.20 (3H, s), 2.68-2.72 (2H, m), 3.92 (2H, s), 7.10 (2H, d, J=8 Hz), 7.27(2H, d, J=8 Hz), 7.41 (1H, dd, J=7, 1 Hz), 7.50-7.60(3H, m), 7.81 (1H, d, J=8 Hz), 8.11-8.16 (2H, m).

Example 13

Production of 5-{[2'-(1H-tetrazol-5-yl)biphenyl-4-yl]methyl}-6-butyl-3-[3-chloro-5-(trifluoromethyl)pyridin-2-yl]-2-methylpyrimidin-4(3H)-one

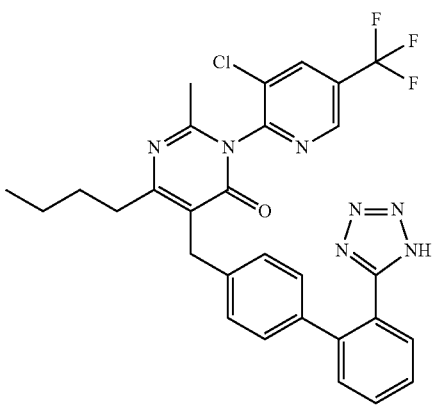 [SMILES: CCCCc1nc(C)n(-c2ncc(C(F)(F)F)cc2Cl)c(=O)c1Cc1ccc(-c2ccccc2-c2nnn[nH]2)cc1]

4'-{{4-butyl-1-[3-chloro-5-(trifluoromethyl)pyridin-2-yl]-2-methyl-6-oxo-1,6-dihydropyrimidin-5-yl}methyl}biphenyl-2-carbonitrile was obtained according to the same reaction and treatment as the Process 2 of Example 1 by using 2-amino-3-chloro-5-(trifluoromethyl)pyridine instead of 2-aminopyridine.

$^1$H-NMR (CDCl$_3$) δ:
0.94 (3H, t, J=7 Hz), 1.41 (2H, sextet, J=8 Hz), 1.56-1.66 (2H, m), 2.15 (3H, s), 2.60-2.72 (2H, m), 3.96 (1H, d, J=15 Hz), 4.02 (1H, d, J=15 Hz), 7.36-7.51 (6H, m), 7.62 (1H, m), 7.74 (1H, d, J=8 Hz), 8.19(1H, d, J=2 Hz), 8.84(1H, d, J=2 Hz).

The target compound was obtained according to the same reaction and treatment as the Process 3 of Example 1 by using 4'-{{4-butyl-1-[3-chloro-5-(trifluoromethyl)pyridin-2-yl]-2-methyl-6-oxo-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.96 (3H, t, J=7 Hz), 1.43 (2H, sextet, J=8 Hz), 1.64-1.72 (2H, m), 2.14 (3H, s), 2.63-2.75(2H, m), 3.95 (2H, s), 7.11 (2H, d, J=8 Hz), 7.27 (2H, d, J=8 Hz), 7.38-7.60 (3H, m), 8.15 (1H, dd, J=8, 2 Hz), 8.19 (1H, d, J=2 Hz), 8.83(1H, d, J=2 Hz).

Example 14

Production of 5-{[2'-(1H-tetrazol-5-yl)biphenyl-4-yl]methyl}-6-butyl-2-methyl-3-(5-nitropyridin-2-yl)pyrimidin-4 (3H)-one

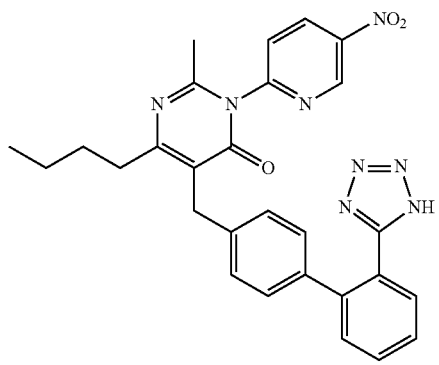 [SMILES: CCCCc1nc(C)n(-c2ccc([N+](=O)[O-])cn2)c(=O)c1Cc1ccc(-c2ccccc2-c2nnn[nH]2)cc1]

4'-{[4-butyl-2-methyl-1-(5-nitropyridin-2-yl)-6-oxo-1,6-dihydropyrimidin-5-yl]methyl}biphenyl-2-carbonitrile was obtained according to the same reaction and treatment as the Process 2 of Example 1 by using 2-amino-5-nitropyridine instead of 2-aminopyridine.

$^1$H-NMR (CDCl$_3$) δ:
0.95 (3H, t, J=7 Hz), 1.42 (2H, sextet, J=8 Hz), 1.60-1.67 (2H, m), 2.21 (3H, s), 2.66-2.70 (2H, m), 3.97 (2H, s), 7.37-7.49 (6H, m), 7.60-7.66 (2H, m), 7.74 (1H, dd, J=8, 1 Hz), 8.68 (1H, dd, J=8, 3 Hz), 9.47(1H, d, J=3 Hz).

The target compound was obtained according to the same reaction and treatment as the Process 3 of Example 1 by using 4'-{[4-butyl-2-methyl-1-(5-nitropyridin-2-yl)-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.96 (3H, t, J=7 Hz), 1.44 (2H, sextet, J=8 Hz), 1.64-1.72 (2H, m), 2.20 (3H, s), 2.68-2.72(2H, m), 3.92 (2H, s), 7.09 (2H, d, J=8 Hz), 7.26 (2H, d, J=8 Hz), 7.42-7.62 (4H, m), 8.12 (1H, d, J=9 Hz), 8.69 (1H, dd, J=9, 3 Hz), 9.44 (1H, d, J=3 Hz).

Example 15

Production of 5-{[2'-(1H-tetrazol-5-yl)biphenyl-4-yl]methyl}-3-[5-(1H-tetrazol-5-yl)pyridin-2-yl]-6-butyl-2-methylpyrimidin-4 (3H)-one

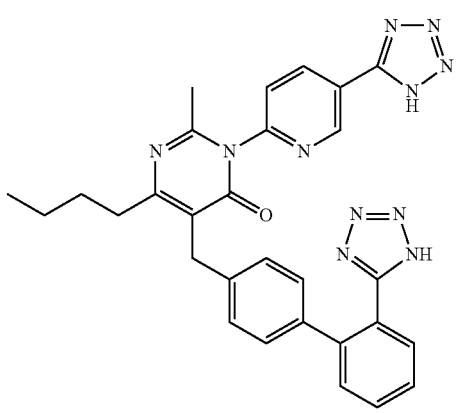 [SMILES: CCCCc1nc(C)n(-c2ccc(-c3nnn[nH]3)cn2)c(=O)c1Cc1ccc(-c2ccccc2-c2nnn[nH]2)cc1]

6-{4-butyl-5-[2'-cyanobiphenyl-4-yl)methyl]-2-methyl-6-oxopyrimidin-1(6H)-yl}nicotinonitrile was obtained according to the same reaction and treatment as the Process 2 of Example 1 by using 2-amino-5-cyanopyridine instead of 2-aminopyridine.

¹H-NMR (CDCl₃) δ:

0.94 (3H, t, J=7 Hz), 1.41 (2H, sextet, J=8 Hz), 1.50-1.66 (2H, m), 2.19 (3H, s), 2.66-2.70 (2H, m), 3.96 (2H, s), 7.36-7.48 (6H, m), 7.56-7.62 (2H, m), 7.74 (1H, d, J=8 Hz), 8.18 (1H, dd, J=8, 2 Hz), 8.95(1H, d, J=2 Hz).

The target compound was obtained according to the same reaction and treatment as the Process 3 of Example 1 by using 6-{(4-butyl-5-[(2'-cyanobiphenyl-4-yl)methyl]-2-methyl-6-oxopyrimidin-1(6H)-yl}nicotinonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃+CD₃OD) δ:

0.89 (3H, t, J=7 Hz), 1.35-1.40 (2H, m), 1.60-1.70 (2H, m), 2.07 (3H, s), 2.60-2.70(2H, m), 3.92 (2H, s), 7.30-7.41 (7H, m), 7.57 (1H, m), 7.68 (1H, d, J=8 Hz), 8.22 (1H, brs), 9.00 (1H, brs).

Example 16

Production of 5-{[2'-(1H-tetrazol-5-yl)biphenyl-4-yl]methyl}-3-(5-bromopyrimidin-2-yl)-6-butyl-2-methylpyrimidin-4 (3H)-one

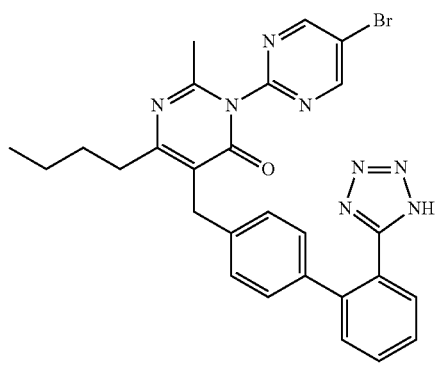 [SMILES: CCCCc1nc(C)n(-c2ncc(Br)cn2)c(=O)c1Cc1ccc(-c2ccccc2-c2nnn[nH]2)cc1]

4'-{[1-(5-bromopyrimidin-2-yl)-4-butyl-2-methyl-6-oxo-1,6-dihydropyrimidin-5-yl]methyl}biphenyl-2-carbonitrile was obtained according to the same reaction and treatment as the Process 2 of Example 1 by using 2-amino-5-bromopyrimidine instead of 2-aminopyridine.

¹H-NMR (CDCl₃) δ:

0.93 (3H, t, J=7 Hz), 1.32-1.46 (2H, m), 1.53-1.6 (2H, m), 2.18 (3H, s), 2.66 (2H, t, J=8 Hz), 3.97 (2H, s), 7.33-7.50 (6H, m), 7.61 (1H, td, J=8, 1 Hz), 7.74 (1H, dd, J=8, 1 Hz), 8.98 (2H, s).

The target compound was obtained according to the same reaction and treatment as the Process 3 of Example 1 by using 4'-{[1-(5-bromopyrimidin-2-yl)-4-butyl-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.93 (3H, t, J=7 Hz), 1.32-1.47 (2H, m), 1.55-1.67 (2H, m), 2.15 (3H, s), 2.63 (2H, t, J=8 Hz), 3.86 (2H, s), 7.01 (2H, d, J=7 Hz), 7.16 (2H, d, J=7 Hz), 7.37 (1H, d, J=8 Hz), 7.42-7.58 (2H, m), 8.01 (1H, br), 8.92 (2H, s).

Example 17

Production of 5-{[2'-(1H-tetrazol-5-yl)biphenyl-4-yl]methyl}-6-butyl-2-methyl-3-(pyrimidin-2-yl)pyrimidin-4 (3H)-one

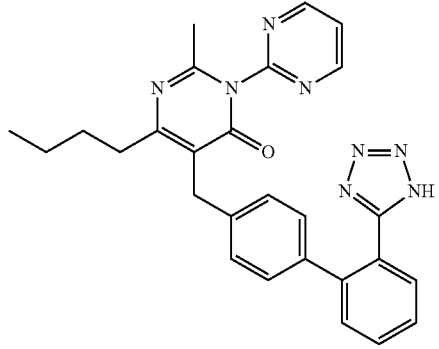 [SMILES: CCCCc1nc(C)n(-c2ncccn2)c(=O)c1Cc1ccc(-c2ccccc2-c2nnn[nH]2)cc1]

To the methanol (20 mL) solution of 4'-{[1-(5-bromopyrimidin-2-yl)-4-butyl-2-methyl-6-oxo-1,6-dihydropyrimidin-5-yl]methyl}biphenyl-2-carbonitrile (100 mg, 0.194 mmol), which has been produced in Example 16, 10% Pd-C (containing 50% moisture, 20 mg) was added for hydrogenation. After stirring at room temperature for 1 hr, the reaction mixture was filtered through a pad of celite and washed with methanol. The filtrate was distilled off and the resulting residues were subjected to silica gel column chromatography (chloroform:methanol=10:1) to obtain 4'-{[4-butyl-2-methyl-6-oxo-1-(pyrimidin-2-yl)-1,6-dihydropyrimidin-5-yl]methyl}biphenyl-2-carbonitrile (85 mg, 100%) as a pale yellow solid.

$^1$H-NMR (CDCl$_3$) δ:

0.93 (3H, t, J=7 Hz), 1.34-1.46 (2H, m), 1.52-1.68 (2H, m), 2.16 (3H, s), 2.66 (2H, t, J=8 Hz), 3.99 (2H, s), 7.32-7.50 (7H, m), 7.61 (1H, td, J=8, 2 Hz), 7.73 (1H, dd, J=8, 2 Hz), 8.95 (2H, d, J=5 Hz).

The target compound was obtained according to the same reaction and treatment as the Process 3 of Example 1 by using 4'-{[4-butyl-2-methyl-6-oxo-1-(pyrimidin-2-yl)-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.92 (3H, t, J=7 Hz), 1.30-1.48 (2H, m), 1.52-1.70 (2H, m), 2.13 (3H, s), 2.63 (2H, br), 3.86 (2H, s), 7.02 (2H, br), 7.16 (2H, br), 7.30-7.57 (4H, m), 7.98 (1H, br), 8.87 (2H, d, J=5 Hz).

Example 18

Production of 5-{[2'-(1H-tetrazol-5-yl)biphenyl-4-yl]methyl}-6-butyl-3-(5-methoxypyrimidin-2-yl)-2-methylpyrimidin-4 (3H)-one

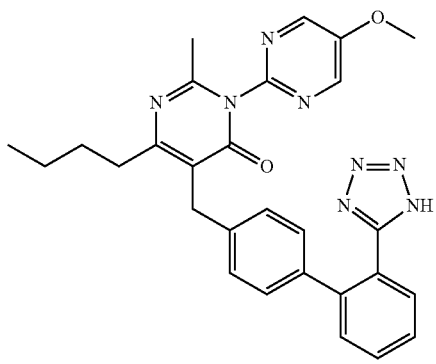

4'-{[4-butyl-1-(5-methoxypyrimidin-2-yl)-2-methyl-6-oxo-1,6-dihydropyrimidin-5-yl]methyl}biphenyl-2-carbonitrile was obtained according to the same reaction and treatment as the Process 2 of Example 1 by using 2-amino-5-methoxypyrimidine instead of 2-aminopyridine.

$^1$H-NMR (CDCl$_3$) δ:

0.93 (3H, t, 7 Hz), 1.33-1.45 (2H, m), 1.52-1.67, (2H, m), 2.16 (3H, s), 2.65 (2H, t, J=8 Hz), 3.98 (2H, s), 4.00 (3H, s), 7.34-7.49 (6H, m), 7.61 (1H, td, J=8, 2 Hz), 7.74 (1H, dd, J=8, 2 Hz), 8.54 (2H, s).

The target compound was obtained according to the same reaction and treatment as the Process 3 of Example 1 by using 4'-{[4-butyl-1-(5-methoxypyrimidin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (d$_6$-DMSO) δ:

0.77 (3H, t, J=7 Hz), 1.13-1.28 (2H, m), 1.33-1.47 (2H, m), 1.94 (3H, s), 2.46 (2H, t, J=8 Hz), 3.72 (2H, s), 3.92 (3H, s), 6.91 (2H, d, J=8 Hz), 7.03 (2H, d, J=8 Hz), 7.36-7.47 (2H, m), 7.49-7.57 (2H, m), 8.68 (2H, s).

Example 19

Production of 5-{[2'-(1H-tetrazol-5-yl)biphenyl-4-yl]methyl}-3-[5-(benzyloxy)pyrimidin-2-yl]-6-butyl-2-methylpyrimidin-4 (3H)-one

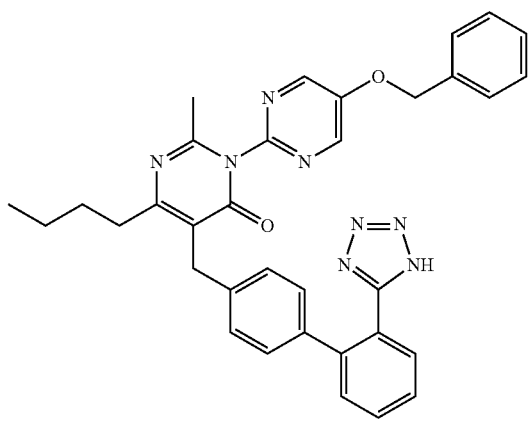 [SMILES: CCCCc1nc(C)n(-c2ncc(OCc3ccccc3)cn2)c(=O)c1Cc1ccc(-c2ccccc2-c2nnn[nH]2)cc1]

4'-{{1-[5-(benzyloxy)pyrimidin-2-yl]-4-butyl-2-methyl-6-oxo-1,6-dihydropyrimidin-5-yl}methyl}biphenyl-2-carbonitrile was obtained according to the same reaction and treatment as the Process 2 of Example 1 by using 2-amino-5-benzyloxypyrimidine instead of 2-aminopyridine.

$^1$H-NMR(CDCl$_3$) δ:

0.92 (3H, t, d=7.4 Hz), 1.33-1.47 (2H, m), 1.51-1.68 (2H, m), 2.16 (3H, s), 2.65 (2H, t, J=7.9 Hz), 3.97 (2H, s), 5.22 (2H, s), 7.32-7.52 (11H, m), 7.61 (1H, t, J=7.7 Hz), 7.73 (1H, d, J=7.7 Hz), 8.60 (2H, s).

The target compound was obtained according to the same reaction and treatment as the Process 3 of Example 1 by using 4'-{{1-[5-(benzyloxy)pyrimidin-2-yl]-4-butyl-2-methyl-6-oxo-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ: 0.92 (3H, t, J=7 Hz), 1.30-1.46 (2H, m), 1.50-1.67 (2H, m), 2.11 (3H, s), 2.61 (2H, t, J=8 Hz), 3.85 (2H, s), 5.18 (2H, s), 7.01 (2H, d, J=8 Hz), 7.16 (2H, d, J=8 Hz), 7.30-7.59 (8H, m), 7.98 (1H, d, J=7 Hz), 8.51 (2H, s).

Example 20

Production of 5-{[2'-(1H-tetrazol-5-yl)biphenyl-4-yl]methyl}-6-butyl-3-(5-hydroxypyrimidin-2-yl)-2-methylpyrimidin-4 (3H)-one

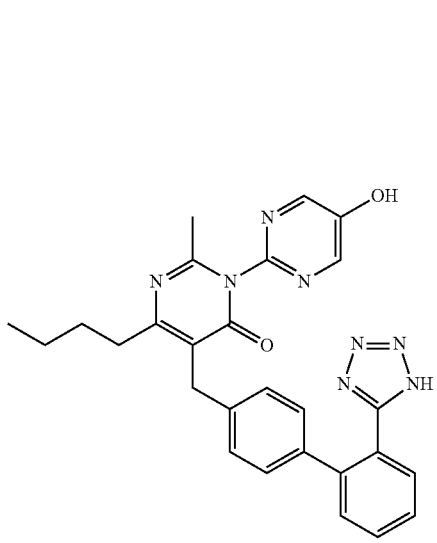 [SMILES: CCCCc1nc(C)n(-c2ncc(O)cn2)c(=O)c1Cc1ccc(-c2ccccc2-c2nnn[nH]2)cc1]

To the methanol (10 mL) solution of 4'-{[1-[5-(benzyloxy)pyrimidin-2-yl]-4-butyl-2-methyl-6-oxo-1,6-dihydropyrimidin-5-yl]methyl}biphenyl-2-carbonitrile (235 mg, 0.434 mmol), 10% Pd—C (containing 50% moisture, 120 mg) was added for hydrogenation. After stirring at room temperature for 1 hr, the reaction mixture was filtered through a pad of celite and washed with methanol. The filtrate was distilled off and the resulting residues were subjected to silica gel column chromatography (chloroform:methanol=10:1) to obtain 4'-{[4-butyl-1-(5-hydroxypyrimidin-2-yl)-2-methyl-6-oxo-1,6-dihydropyrimidin-5-yl]methyl}biphenyl-2-carbonitrile.

$^1$H-NMR (CDCl$_3$) δ:

0.93 (3H, t, d=7 Hz), 1.33-1.48 (2H, m), 1.53-1.67 (2H, m), 2.17 (3H, s), 2.69 (2H, t, J=8 Hz), 4.05 (2H, s), 7.32-7.46 (3H, m), 7.49 (2H, d, J=8 Hz), 7.62 (1H, t, J=8 Hz), 7.75 (1H, d, J=8 Hz), 8.16 (2H, s), 9.20 (1H, br s).

The target compound was obtained according to the same reaction and treatment as the Process 3 of Example 1 by using 4'-{[4-butyl-1-(5-hydroxypyrimidin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CD$_3$OD) δ:

0.91 (3H, t, J=7 Hz), 1.30-1.44 (2H, m), 1.46-1.60 (2H, m), 2.13 (3H, s), 2.59 (2H, t, J=8 Hz), 3.89 (2H, s), 7.02 (2H, d, J=8 Hz), 7.12 (2H, d, J=8 Hz), 7.43-7.49 (2H, m), 7.52-7.59 (2H, m), 8.47 (2H, s).

Example 21

Production of 5-{[2'-(1H-tetrazol-5-yl)biphenyl-4-yl]methyl}-6-butyl-3-(5-ethoxypyrimidin-2-yl)-2-methylpyrimidin-4 (3H)-one

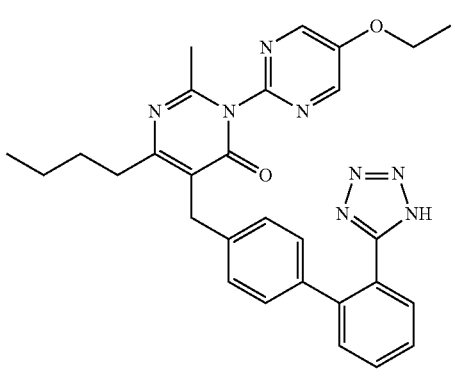 [SMILES: CCCCc1nc(C)n(-c2ncc(OCC)cn2)c(=O)c1Cc1ccc(-c2ccccc2-c2nnn[nH]2)cc1]

Process 1: To the acetonitrile (1 mL) solution of 4'-{[4-butyl-1-(5-hydroxypyrimidin-2-yl)-2-methyl-6-oxo-1,6-dihydropyrimidin-5-yl]methyl}biphenyl-2-carbonitrile (68 mg, 0.15 mmol), potassium carbonate (41 mg, 0.30 mmol) and iodoethane (70 mg, 0.448 mmol) were added and stirred at 60° C. for 5 hrs. After that, the reaction mixture was filtered and washed with ethyl acetate. The filtrate was distilled off to obtain 4'-{[4-butyl-1-(5-ethoxypyrimidin-2-yl)-2-methyl-6-oxo-1,6-dihydropyrimidin-5-yl]methyl}biphenyl-2-carbonitrile.

$^1$H-NMR (CDCl$_3$) δ:

0.92 (3H, t, 7 Hz), 1.35-1.44 (2H, m), 1.50 (3H, t, 7 Hz), 1.56-1.63 (2H, m), 2.16 (3H, s), 2.65 (2H, t, J=8 Hz), 3.98 (2H, s), 4.21 (2H, q, J=7 Hz), 7.38-7.47 (6H, m), 7.60 (1H, td, J=8, 1 Hz), 7.73 (1H, dd, J=8, 1 Hz), 8.52 (2H, s).

Process 2: The target compound was obtained according to the same reaction and treatment as the Process 3 of Example 1 by using 4'-{[4-butyl-1-(5-ethoxypyrimidin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ: 0.91 (3H, t, J=7 Hz), 1.34-1.41 (2H, m, J=7 Hz), 1.50 (3H, t, J=7 Hz), 1.56-1.62 (2H, m), 2.10 (3H, s), 2.61 (2H, t, J=8 Hz), 3.85 (2H, s), 4.19 (2H, q, J=7 Hz), 7.01 (2H, d, J=8 Hz), 7.16 (2H, d, J=8 Hz), 7.39-7.55 (3H, m), 7.94 (1H, d, J=8 Hz), 8.43 (2H, s).

Example 22

Production of 5-{[2'-(1H-tetrazol-5-yl)biphenyl-4-yl]methyl}-6-butyl-2-methyl-3-(5-propoxypyrimidin-2-yl)pyrimidin-4 (3H)-one

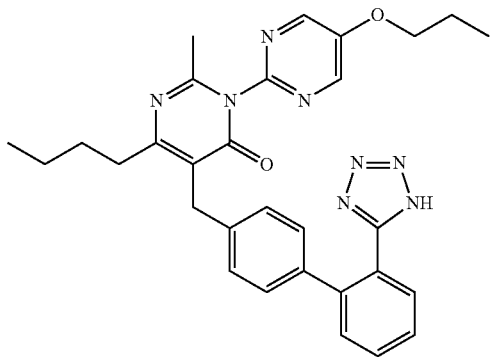 [SMILES: CCCCc1nc(C)n(-c2ncc(OCCC)cn2)c(=O)c1Cc1ccc(-c2ccccc2-c2nnn[nH]2)cc1]

4'-{[4-butyl-2-methyl-6-oxo-1-(5-propoxypyrimidin-2-yl)-1,6-dihydropyrimidin-5-yl]methyl}biphenyl-2-carbonitrile was obtained according to the same reaction and treatment as the Process 1 of Example 21 by using 1-iodopropane instead of iodoethane.

$^1$H-NMR (CDCl$_3$) δ:

0.93 (3H, t, J=7 Hz), 1.08 (3H, t, J=7 Hz), 1.35-1.44 (2H, m), 1.56-1.64 (2H, m), 1.80-1.93 (2H, m), 2.16 (3H, s), 2.65 (2H, t, J=8 Hz), 3.98 (2H, s), 4.09 (2H, t, J=6 Hz), 7.38-7.47 (6H, m), 7.61 (1H, td, J=8, 1 Hz), 7.73 (1H, dd, J=8, 2 Hz), 8.52 (2H, s).

The target compound was obtained according to the same reaction and treatment as the Process 3 of Example 1 by using 4'-{[4-butyl-2-methyl-6-oxo-1-(5-propoxypyrimidin-2-yl)-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.92 (3H, t, J=7 Hz), 1.08 (3H, t, J=7 Hz), 1.32-1.43 (2H, m), 1.58-1.66 (2H, m), 1.84-1.95 (2H, m), 2.12 (3H, s), 2.63 (2H, t, J=8 Hz), 3.86 (2H, s), 4.08 (2H, t, J=6 Hz), 7.02 (2H, d, J=8 Hz), 7.17 (2H, d, J=8 Hz), 7.38-7.56 (3H, m), 7.98 (1H, d, J=7 Hz), 8.45 (2H, s).

Example 23

Production of 5-{[2'-(1H-tetrazol-5-yl)biphenyl-4-yl]methyl}-6-butyl-3-(5-isopropoxypyrimidin-2-yl)-2-methylpyrimidin-4 (3H)-one

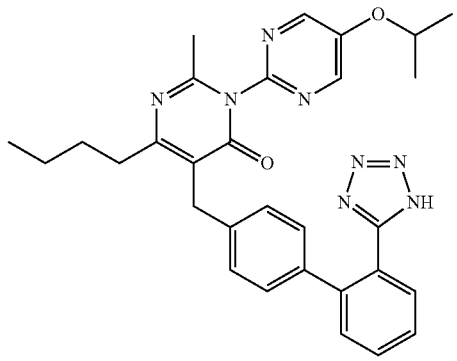 [SMILES: CCCCc1nc(C)n(-c2ncc(OC(C)C)cn2)c(=O)c1Cc1ccc(-c2ccccc2-c2nnn[nH]2)cc1]

4'-{[4-butyl-1-(5-isopropoxypyrimidin-2-yl)-2-methyl-6-oxo-1,6-dihydropyrimidin-5-yl]methyl}biphenyl-2-carbonitrile was obtained according to the same reaction and treatment as the Process 1 of Example 21 by using 2-iodopropane instead of iodoethane.

$^1$H-NMR (CDCl$_3$) δ:

0.93 (3H, t, J=7 Hz), 1.35-1.46 (8H, m), 1.55-1.62 (2H, m), 2.04 (3H, s), 2.65 (2H, t, J=8 Hz), 3.98 (2H, s), 4.66-4.75 (1H, m), 7.38-7.49 (6H, m), 7.61 (1H, td, J=8, 1 Hz), 7.73 (1H, dd, J=8, 1 Hz), 8.49 (2H, s).

The target compound was obtained according to the same reaction and treatment as the Process 3 of Example 1 by using 4'-{[4-butyl-1-(5-isopropoxypyrimidin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.93 (3H, t, J=7 Hz), 1.33-1.43 (8H, m), 1.57-1.64 (2H, m), 2.11 (3H, s), 2.61 (2H, t, J=8 Hz), 3.84 (2H, s), 4.64-4.73 (1H, m), 7.00 (2H, d, J=8 Hz), 7.15 (2H, d, J=8 Hz), 7.39-7.56 (3H, m), 7.92 (1H, d, J=7 Hz), 8.42 (2H, s).

Example 24

Production of 5-{[2'-(1H-tetrazol-5-yl)biphenyl-4-yl]methyl}-3-(5-butoxypyrimidin-2-yl)-6-butyl-2-methylpyrimidin-4 (3H)-one

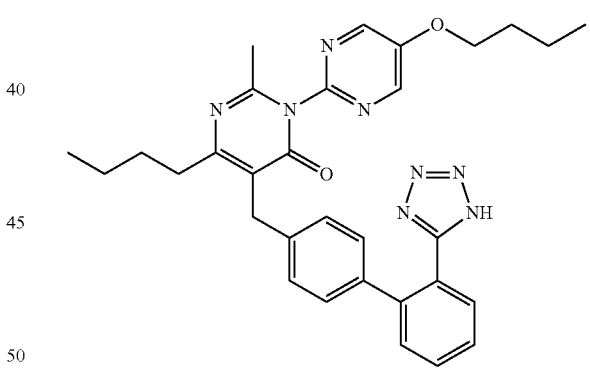

4'-{[1-(5-butoxypyrimidin-2-yl)-4-butyl-2-methyl-6-oxo-1,6-dihydropyrimidin-5-yl]methyl}biphenyl-2-carbonitrile was obtained according to the same reaction and treatment as the Process 1 of Example 21 by using 1-iodobutane instead of iodoethane.

$^1$H-NMR (CDCl$_3$) δ:

0.93 (3H, t, J=7 Hz), 1.00 (3H, t, J=7 Hz), 1.35-1.44 (2H, m), 1.48-1.64 (4H, m), 1.78-1.88 (2H, m), 2.16 (3H, s), 2.65 (2H, t, J=8 Hz), 3.98 (2H, s), 4.15 (2H, t, J=6 Hz), 7.38-7.47 (6H, m), 7.61 (1H, td, J=8, 1 Hz), 7.73 (1H, dd, J=8, 2 Hz), 8.52 (2H, s).

The target compound was obtained according to the same reaction and treatment as the Process 3 of Example 1 by using 4'-{[1-(5-butoxypyrimidin-2-yl)-4-butyl-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.90 (3H, t, J=7 Hz), 0.99 (3H, t, J=7 Hz), 1.32-1.41 (2H, m), 1.46-1.62 (4H, m), 1.78-1.85 (2H, m), 2.09 (3H, s), 2.58 (2H, t, J=8 Hz), 3.81 (2H, s), 4.10 (2H, t, J=6 Hz), 6.94 (2H, d, J=8 Hz), 7.09 (2H, d, J=8 Hz), 7.37-7.54 (3H, m), 7.86 (1H, d, J=8 Hz), 8.42 (2H, s).

Example 25

Production of 5-{[2'-(1H-tetrazol-5-yl)biphenyl-4-yl]methyl}-6-butyl-3-[5-(3-hydroxypropoxy)pyrimidin-2-yl]-2-methylpyrimidin-4 (3H)-one

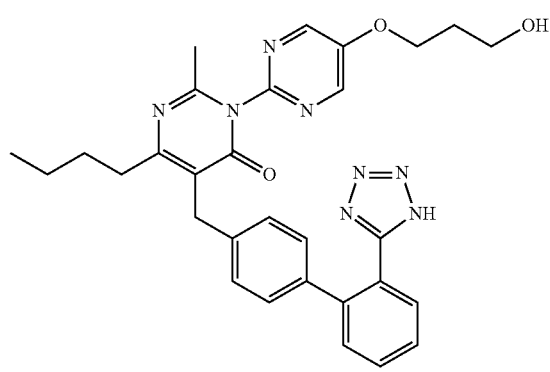 [SMILES: CCCCc1nc(C)n(-c2ncc(OCCCO)cn2)c(=O)c1Cc1ccc(-c2ccccc2-c2nnn[nH]2)cc1]

4'-{{4-butyl-1-[5-(3-hydroxypropoxy)pyrimidin-2-yl]-2-methyl-6-oxo-1,6-dihydropyrimidin-5-yl}methyl}biphenyl-2-carbonitrile was obtained according to the same reaction and treatment as the Process 1 of Example 21 by using 3-bromo-1-propanol instead of iodoethane.

¹H-NMR (CDCl₃) δ:

0.92 (3H, t, J=7 Hz), 1.34-1.45 (2H, m), 1.55-1.65 (2H, m), 2.02-2.10 (2H, m), 2.15 (3H, s), 2.65 (2H, t, J=8 Hz), 3.80 (2H, t, J=6 Hz), 3.98 (2H, s), 4.26 (2H, t, J=6 Hz), 7.35-7.49 (6H, m), 7.61 (1H, td, J=8, 1 Hz), 7.73 (1H, dd, J=8, 1 Hz), 8.53 (2H, s).

The target compound was obtained according to the same reaction and treatment as the Process 3 of Example 1 by using 4'-{[4-butyl-1-[5-(3-hydroxypropoxy)pyrimidin-2-yl]-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.90 (3H, t, J=7 Hz), 1.31-1.42 (2H, m), 1.54-1.65 (2H, m), 1.81-1.89 (2H, m), 2.08 (3H, s), 2.60 (2H, t, J=8 Hz), 3.57-3.65 (2H, m), 3.81 (2H, s), 4.03-4.11 (2H, m), 5.15 (1H, br), 6.94 (2H, d, J=8 Hz), 7.04 (2H, d, J=8 Hz), 7.32-7.52 (3H, m), 7.8 (1H, d, J=7 Hz), 8.34 (2H, s).

Example 26

Production of 5-{[2'-(1H-tetrazol-5-yl)biphenyl-4-yl]methyl}-6-butyl-2-methyl-3-{5-[2-(methylthio)ethoxy]pyrimidin-2-yl}pyrimidin-4 (3H)-one

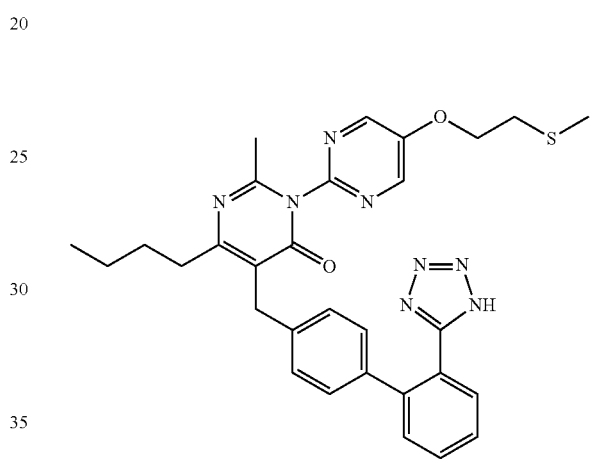

4'-{{4-butyl-2-methyl-1-{5-[2-(methylthio)ethoxy]pyrimidin-2-yl}-6-oxo-1,6-dihydropyrimidin-5-yl}methyl}biphenyl-2-carbonitrile was obtained according to the same reaction and treatment as the Process 2 of Example 1 by using 2-amino-5-[2-(methylthio)ethoxy]pyrimidine instead of 2-aminopyridine.

¹H-NMR (CDCl₃) δ:

0.93 (3H, t, J=7 Hz), 1.30-1.45 (2H, m), 1.50-1.65 (2H, m), 2.16 (3H, s), 2.24 (3H, s), 2.65 (2H, t, J=8 Hz), 2.95 (2H, t, J=7 Hz), 3.98 (2H, s), 4.32 (2H, t, J=7 Hz), 7.30-7.50 (6H, m), 7.61 (1H, td, J=8, 1 Hz), 7.73 (1H, d, J=8 Hz), 8.55 (2H, s).

The target compound was obtained according to the same reaction and treatment as the Process 3 of Example 1 by using 4'-{{4-butyl-2-methyl-1-{5-[2-(methylthio)ethoxy]pyrimidin-2-yl}-6-oxo-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.91 (3H, t, J=7 Hz), 1.30-1.47 (2H, m), 1.50-1.66 (2H, m), 2.10 (3H, s), 2.24 (3H, s), 2.59 (2H, t, J=8 Hz), 2.94 (2H, t, J=7 Hz), 3.84 (2H, s), 4.30 (2H, t, J=7 Hz), 6.99 (2H, d, J=8 Hz), 7.14 (2H, d, J=8 Hz), 7.39 (1H, d, J=8 Hz), 7.46 (1H, t, J=8 Hz), 7.55 (1H, t, J=7 Hz), 7.93 (1H, d, J=8 Hz), 8.46 (2H, s).

Example 27

Production of 5-{[2'-(1H-tetrazol-5-yl)biphenyl-4-yl] methyl}-6-butyl-2-methyl-3-{5-[2-(methylsulfonyl) ethoxy]pyrimidin-2-yl}pyrimidin-4 (3H)-one

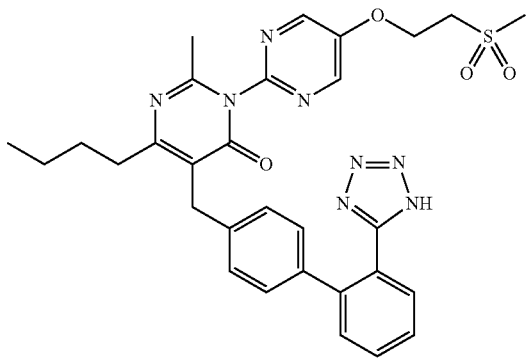 [SMILES: CCCCc1nc(C)n(-c2ncc(OCCS(C)(=O)=O)cn2)c(=O)c1Cc1ccc(-c2ccccc2-c2nnn[nH]2)cc1]

To the methanol (0.4 mL) solution of 5-{[2'-(1H-tetrazol-5-yl)biphenyl-4-yl]methyl}-6-butyl-2-methyl-3-{5-[2-(methylthio)ethoxy]pyrimidin-2-yl}pyrimidin-4 (3H)-one (15 mg, 0.027 mmol), methanol (0.4 mL) solution of hydrogen peroxide solution (30% solution, 15.3 mg, 0.135 mmol) and methanol (0.4 mL) solution of tantalum chloride (1.0 mg, 0.0027 mmol) were added. The mixture was stirred at room temperature for 12 hrs and then the solvent was distilled off. The resulting residues were subjected to silica gel column chromatography (chloroform:methanol=5:1) to obtain the target compound.

$^1$H-NMR (CDCl$_3$) δ:

0.93 (3H, t, J=7 Hz), 1.33-1.47 (2H, m), 1.52-1.68 (2H, m), 2.14 (3H, s), 2.64 (2H, t, J=8 Hz), 3.07 (3H, s), 3.51 (2H, t, J=7 Hz), 3.89 (2H, s), 4.59 (2H, t, J=7 Hz), 7.05 (2H, d, J=8 Hz), 7.21 (2H, d, J=8 Hz), 7.39 (1H, d, J=7 Hz), 7.43-7.59 (2H, m), 8.05 (1H, d, J=8 Hz), 8.53 (2H, s).

Example 28

Production of 5-{[2'-(1H-tetrazol-5-yl)biphenyl-4-yl] methyl}-6-butyl-3-[5-(cyclohexyloxy)pyrimidin-2-yl]-2-methylpyrimidin-4 (3H)-one

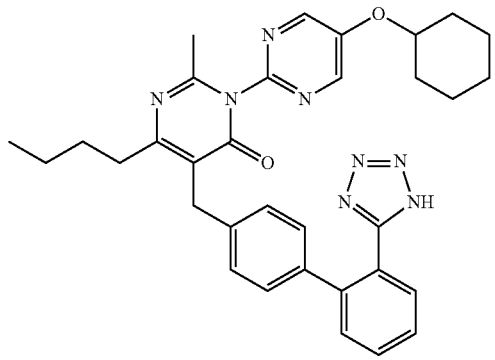 [SMILES: CCCCc1nc(C)n(-c2ncc(OC3CCCCC3)cn2)c(=O)c1Cc1ccc(-c2ccccc2-c2nnn[nH]2)cc1]

Process 1: 4'-{[4-butyl-1-(5-hydroxypyrimidin-2-yl)-2-methyl-6-oxo-1,6-dihydropyrimidin-5-yl]methyl}biphenyl-2-carbonitrile (27 mg, 0.060 mmol), cyclohexanol (12 mg, 0.120 mmol) and triphenylphosphine (32 mg, 0.122 mmol) were dried for 3 hrs in vacuo, purged with argon, added 1,4-dioxane (1 mL) and diethyl azodicarboxylic acid (2.2 mol/L toluene solution, 70 μL, 0.154 mmol), and then stirred at 80° C. for 3 hrs. The reaction mixture was added water and extracted with ethyl acetate. The organic layer was combined, washed with water and brine, dried over anhydrous sodium sulfate, and concentrated in vacuo. The resulting residues were subjected to silica gel column chromatography (chloroform:methanol=10:1) to obtain 4'-{{4-butyl-1-[5-(cyclohexyloxy)pyrimidin-2-yl]-2-methyl-6-oxo-1,6-dihydropyrimidin-5-yl}methyl}biphenyl-2-carbonitrile (18 mg, 56%).

$^1$H-NMR (CDCl$_3$) δ:

0.93 (3H, t, J=7 Hz), 1.42(2H, sextet, J=8 Hz), 1.35-1.60 (6H, m), 1.56-1.64 (2H, m), 1.65-1.80(2H, m), 1.90-2.10 (2H, m), 2.16 (3H, s), 2.63-2.67 (2H, m), 3.98 (2H, s), 4.42 (1H, m), 7.38-7.48(6H, m), 7.61(1H, t, J=6 Hz), 7.73(1H, d, J=7 Hz), 8.50 (2H, s).

Process 2: The target compound was obtained according to the same reaction and treatment as the Process 3 of Example 1 by using 4'-{{4-butyl-1-[5-(cyclohexyloxy)pyrimidin-2-yl]-2-methyl-6-oxo-1,6dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.95 (3H, t, J=7 Hz), 1.25-1.50(6H, m), 1.50-1.75(4H, m), 1.75-2.00(2H, m), 2.00-2.10(2H, m), 2.17(3H, s), 2.69-2.73 (2H, m), 3.92(2H, s), 4.42(1H, m), 7.11(2H, d, J=8 Hz), 7.29(2H, d, J=8 Hz), 7.38-7.59(3H, m), 8.14(1H, d, J=8 Hz), 8.47(2H, s).

Example 29

Production of 5-{[2'-(1H-tetrazol-5-yl)biphenyl-4-yl] methyl}-6-butyl-2-methyl-3-[5-(4-oxocyclohexyloxy)pyrimidin-2-yl]pyrimidin-4 (3H)-one

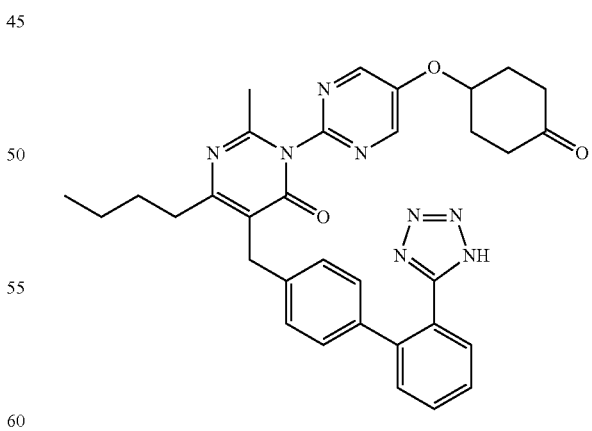

4'-{{4-butyl-1-{5-[4-(tert-butyldimethylsilyloxy)cyclohexyloxy)]pyrimidin-2-yl}-2-methyl-6-oxo-1,6-dihydropyrimidin-5-yl}methyl}biphenyl-2-carbonitrile was obtained according to the same reaction and treatment as the Process 1 of Example 28 by using 4-(tert-butyldimethylsilyloxy)cyclohexanol instead of cyclohexanol.

¹H-NMR (CDCl₃) δ:

0.070(6H, s), 0.089-0.094(12H, m), 1.38-1.45(2H, m), 1.50-2.10 (2H, m), 2.16 (3H, s), 2.63-2.67 (2H, m), 3.86 (1H, m), 3.97 (2H, s), 4.49 (0.5H, m), 5.57 (0.5H, m), 7.38-7.47 (6H, m), 7.61 (1H, td, J=8, 1 Hz), 7.73 (1H, d, J=8 Hz), 8.49 (1H, s), 8.51 (1H, s).

5-{[2'-(1H-tetrazol-5-yl)biphenyl-4-yl]methyl}-6-butyl-3-{5-[4-(tert-butyldimethylsilyloxy)cyclohexyloxy]pyrimidin-2-yl}-2-methylpyrimidin-4 (3H)-one was obtained according to the same reaction and treatment as the Process 3 of Example 1 by using 4'-{{4-butyl-1-{5-[4-(tert-butyldimethylsilyloxy)cyclohexyloxy]pyrimidin-2-yl}-2-methyl-6-oxo-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.063(6H, s), 0.89(4.5H, s), 0.90(4.5H, s), 0.95 (3H, t, J=7 Hz), 1.38 (2H, sextet, J=8 Hz), 1.56-2.06 (10H, m), 2.16 (3H, s), 2.68-2.72 (2H, m), 3.85 (1H, m), 3.91 (2H, s), 4.43 (0.5H, m), 4.49 (0.5H, m), 7.11 (2H, d, J=8 Hz), 7.25-7.30 (2H, m), 7.40-7.58 (3H, m), 8.14 (1H, d, J=8 Hz), 8.46 (1H, s), 8.48 (1H, s).

To the ethanol (1 mL) solution of 5-{[2'-(1H-tetrazol-5-yl)biphenyl-4-yl]methyl}-6-butyl-3-{5-[4-(tert-butyldimethylsilyloxy)cyclohexyloxy]pyrimidin-2-yl}-2-methylpyrimidin-4 (3H)-one (38 mg, 0.054 mmol), conc. HCl (30 mg, 0.823 mmol) was added and stirred at room temperature for 1 hr. The reaction mixture was concentrated in vacuo, and the resulting residues were subjected to silica gel column chromatography (chloroform:methanol=5:1) to obtain 5-{[2'-(1H-tetrazol-5-yl)biphenyl-4-yl]methyl}-6-butyl-3-[5-(4-hydroxycyclohexyloxy)pyrimidin-2-yl]-2-methylpyrimidin-4 (3H)-one.

¹H-NMR (CDCl₃) δ:

0.95 (3H, t, J=7 Hz), 1.25-2.20 (12H, m), 2.17 (3H, s), 2.68-2.72 (2H, m), 3.73 (0.5H, m), 3.79 (0.5H, m), 3.92 (2H, s), 4.39 (0.5H, m), 4.51 (0.5H, m), 7.11 (2H, d, J=8 Hz), 7.25 (2H, d, J=8 Hz), 7.42-7.59 (3H, m), 8.48 (1H, s), 8.50 (1H, s).

To the dichloromethane (0.5 mL) solution of 5-{[2'-(1H-tetrazol-5-yl)biphenyl-4-yl]methyl}-6-butyl-3-[5-(4-hydroxycyclohexyloxy)pyrimidin-2-yl]-2-methylpyrimidin-4 (3H)-one (10 mg, 0.017 mmol), Dess-Martin reagent (11 mg, 0.026 mmol) was added and stirred at room temperature for 1 hr. Dess-Martin reagent (11 mg, 0.026 mmol) was added, and further stirred at room temperature overnight. The reaction mixture was added water and extracted with chloroform. The organic layer was combined, washed with water and brine, dried over anhydrous sodium sulfate, and concentrated in vacuo. The resulting residues were subjected to silica gel column chromatography (chloroform:methanol=5:1) to obtain the target compound.

¹H-NMR (CDCl₃) δ:

0.96 (3H, t, J=8 Hz), 1.30-1.80(6H, m), 2.20(3H, s), 2.30-2.50(4H, m), 2.63-2.73(4H, m), 3.92(2H, s), 4.90(1H, brs), 7.13(2H, d, J=8 Hz), 7.28(2H, d, J=8 Hz), 7.40-7.60(3H, m), 8.16(1H, d, J=8 Hz), 8.59(2H, s).

Example 30

Production of 5-{[2'-(1H-tetrazol-5-yl)biphenyl-4-yl]methyl}-6-butyl-3-(4,6-dichloropyrimidin-2-yl)-2-methylpyrimidin-4 (3H)-one

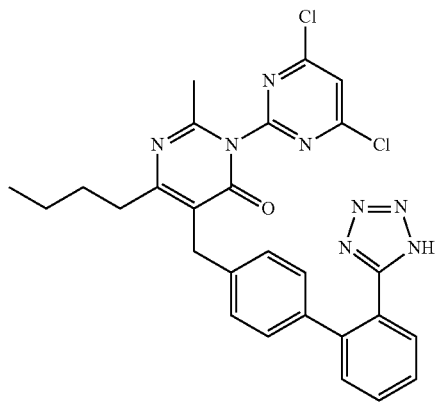 [SMILES: CCCCc1nc(C)n(-c2nc(Cl)cc(Cl)n2)c(=O)c1Cc1ccc(-c2ccccc2-c2nnn[nH]2)cc1]

4'-{[4-butyl-1-(4,6-dichloropyrimidin-2-yl)-2-methyl-6-oxo-1,6-dihydropyrimidin-5-yl]methyl}biphenyl-2-carbonitrile was obtained according to the same reaction and treatment as the Process 2 of Example 1 by using 2-amino-4,6-dichloropyrimidine instead of 2-aminopyridine.

¹H-NMR (CDCl₃) δ:

0.93 (3H, t, J=7 Hz), 1.40 (2H, sextet, J=8 Hz), 1.50-1.70 (2H, m), 2.22 (3H, s), 2.63-2.67 (2H, m), 3.96 (2H, s), 7.36-7.79 (9H, m).

The target compound was obtained according to the same reaction and treatment as the Process 3 of Example 1 by using 4'-{[4-butyl-1-(4,6-dichloropyrimidin-2-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.95 (3H, t, J=7 Hz), 1.42 (2H, sextet, J=8 Hz), 1.61-1.70 (2H, m), 2.23 (3H, s), 2.66-2.71(2H, m), 3.93 (2H, s), 7.14 (2H, d, J=8 Hz), 7.29-7.32 (2H, m), 7.41 (1H, d, J=8 Hz), 7.50-7.60(2H, m), 7.56 (1H, s), 8.19 (1H, d, J=8 Hz).

Example 31

Production of 5-{[2'-(1H-tetrazol-5-yl)biphenyl-4-yl]methyl}-6-butyl-2-methyl-3-{5-[5-methyl-2-phenyloxazol-4-yl)methoxy]pyrimidin-2-yl}pyrimidin-4 (3H)-one

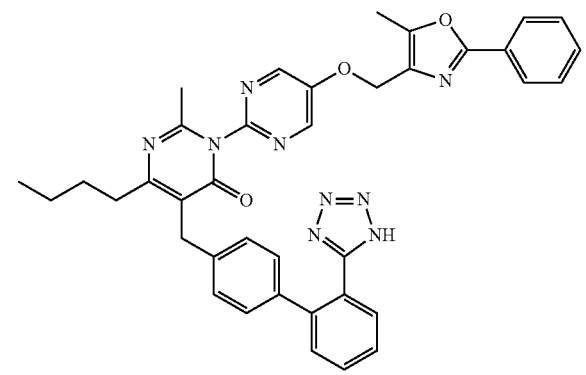 [SMILES: CCCCc1nc(C)n(-c2ncc(OCc3nc(-c4ccccc4)oc3C)cn2)c(=O)c1Cc1ccc(-c2ccccc2-c2nnn[nH]2)cc1]

4'-{{4-butyl-2-methyl-1-{5-[(5-methyl-2-phenyloxazol-4-yl)methoxy]pyrimidin-2-yl}-6-oxo-1,6-dihydropyrimidin-5-yl}methyl}biphenyl-2-carbonitrile was obtained according to the same reaction and treatment as the Process 1 of Example 21 by using 4-chloromethyl-5-methyl-2-phenyloxazole, which has been synthesized with reference to the method described in Synthesis, (17) 2825 (2004), and N,N-dimethylformamide instead of iodoethane and acetonitrile, respectively.

¹H-NMR (CDCl₃) δ:

0.92 (3H, t, J=7 Hz), 1.33-1.47 (2H, m), 1.51-1.67 (2H, m), 2.16 (3H, s), 2.49 (3H, s), 2.65 (2H, t, J=8 Hz), 3.97 (2H, s), 5.17 (2H, s), 7.34-7.52 (9H, m), 7.61 (1H, td, J=8, 2 Hz), 7.74 (1H, dd, J=8, 2 Hz), 7.94-8.08 (2H, m), 8.73 (2H, s).

The target compound was obtained according to the same reaction and treatment as the Process 3 of Example 1 by using 4'-{{4-butyl-2-methyl-1-{5-[(5-methyl-2-phenyloxazol-4-yl)methoxy]pyrimidin-2-yl}-6-oxo-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.90 (3H, t, J=7 Hz), 1.30-1.45 (2H, m), 1.56-1.70 (2H, m), 2.25 (3H, s), 2.52 (3H, s), 2.57 (2H, t, J=8 Hz), 3.92 (2H, s), 4.97 (2H, s), 6.94 (2H, d, J=8 Hz), 7.13 (2H, d, J=8 Hz), 7.25-7.57 (6H, m), 7.82 (2H, d, J=7 Hz), 8.05 (1H, t, J=5 Hz), 8.69 (2H,

Example 32

Production of 5-{[2'-(1H-tetrazol-5-yl)biphenyl-4-yl]methyl}-3-{5-{[2-(5-bromofuran-2-yl)-5-methyloxazol-4-yl]methoxy}pyrimidin-2-yl}-6-butyl-2-methylpyrimidin-4 (3H)-one

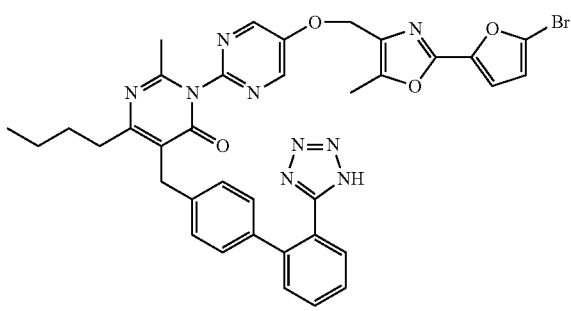 [SMILES: CCCCc1nc(C)n(-c2ncc(OCc3nc(-c4ccc(Br)o4)oc3C)cn2)c(=O)c1Cc1ccc(-c2ccccc2-c2nnn[nH]2)cc1]

The dichloromethane (150 mL) solution of furan-2-carboxylic acid (11.2 g, 100 mmol), 1-ethyl-3-(3-dimethylaminopropyl)carbodiimide hydrochloride salt (28.8 g, 150 mmol), N,N-dimethylaminopyridine (1.2 g, 10 mmol), and acetoin (9.69 g, 110 mmol) was stirred at room temperature for 5 hrs. The reaction mixture was added water and extracted with chloroform. The organic layer was combined, washed with water and brine, dried over anhydrous sodium sulfate, and concentrated in vacuo. The resulting residues were subjected to silica gel column chromatography (hexane/ethyl acetate) to obtain 3-oxobutan-2-yl furan-2-carboxylic acid (18.2 g, 100%) as a yellow oil.

¹H-NMR (CDCl₃) δ:

1.53 (3H, d, J=7 Hz), 2.24 (3H, s), 5.30 (1H, d, J=7 Hz), 6.55 (1H, dd, J=3, 2 Hz), 7.27 (1H, dd, J=3, 1 Hz), 7.63 (1H, dd, J=2, 1 Hz).

The acetic acid (180 mL) solution of 3-oxobutan-2-yl furan-2-carboxylic acid (18.2 g, 100 mmol) and ammonium acetate (38.6 g, 500 mmol) was stirred for 5 hrs under heating reflux condition. The reaction mixture was added water and extracted with ethyl acetate. The organic layer was combined, washed with water and brine, dried over anhydrous sodium sulfate, and concentrated in vacuo. The resulting residues were subjected to silica gel column chromatography (hexane/ethyl acetate) to obtain 2-(furan-2-yl)-4,5-dimethyloxazole (6.4 g, 40%) as a pale yellow oil.

¹H-NMR (CDCl₃) δ:

2.14 (3H, s), 2.29 (3H, s), 6.47-6.52 (1H, m), 6.94 (1H, d, J=3 Hz), 7.49-7.54 (1H, m).

The acetonitrile (16 mL) solution of 2-(furan-2-yl)-4,5-dimethyloxazole (1.63 g, 10 mmol) and N-bromosuccinimide (1.78 g, 10 mmol) was stirred at room temperature for 3 hrs. N-bromosuccinimide (1.78 g, 10 mmol) was added thereto and stirred overnight at room temperature. The reaction mixture was added water and extracted with ethyl acetate. The organic layer was combined, washed with water and brine, dried over anhydrous sodium sulfate, and concentrated in vacuo. The resulting residues were subjected to silica gel column chromatography (hexane/ethyl acetate) to obtain 2-(5-bromofuran-2-yl)-4-(bromomethyl)-5-methyloxazole (1.73 g, 54%) as a pale yellow solid.

¹H-NMR (CDCl₃) δ:

2.39 (3H, s), 4.40 (2H, s), 6.45 (1H, d, J=3 Hz), 6.93 (1H, d, J=3 Hz).

4'-{{1-{5-{[2-(5-bromofuran-2-yl)-5-methyloxazol-4-yl]methoxy}pyrimidin-2-yl}-4-butyl-2-methyl-6-oxo-1,6-dihydropyrimidin-5-yl}methyl}biphenyl-2-carbonitrile was obtained according to the same reaction and treatment as the Process 1 of Example 21 by using 2-(5-bromofuran-2-yl)-4-(bromomethyl)-5-methyloxazole instead of iodoethane.

¹H-NMR(CDCl₃) δ:

0.92 (3H, t, J=7 Hz), 1.34-1.45 (2H, m), 1.55-1.66 (2H, m), 2.16 (3H, s), 2.46 (3H, s), 2.65 (2H, t, J=8 Hz), 3.97 (2H, s), 5.14 (2H, s), 6.47 (1H, d, J=4 Hz), 6.95 (1H, d, J=4 Hz), 7.36-7.48 (6H, m), 7.61 (1H, td, J=8, 1 Hz), 7.73 (1H, dd, J=8, 1 Hz), 8.67 (2H, s).

The target compound was obtained according to the same reaction and treatment as the Process 3 of Example 1 by using 4'-{{1-{5-{[2-(5-bromofuran-2-yl)-5-methyloxazol-4-yl]methoxy}pyrimidin-2-yl}-4-butyl-2-methyl-6-oxo-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.87 (3H, t, J=7 Hz), 1.29-1.39 (2H, m), 1.53-1.65 (2H, m), 2.21 (3H, s), 2.45 (3H, m), 2.52 (2H, t, J=8 Hz), 3.84 (2H, s), 4.92 (2H, s), 6.39 (1H, d, J=3 Hz), 6.82 (1H, d, J=3 Hz), 6.87

(2H, d, J=8 Hz), 7.00 (2H, d, J=8 Hz), 7.33 (1H, d, J=8 Hz), 7.39-7.53 (2H, m), 7.92 (1H, d, J=8 Hz), 8.61 (2H, s).

Example 33

Production of 5-{[2'-(1H-tetrazol-5-yl)biphenyl-4-yl]methyl}-6-butyl-3-{5-{[2-(furan-2-yl)-5-methyloxazol-4-yl]methoxy}pyrimidin-2-yl}-2-methylpyrimidin-4 (3H)-one

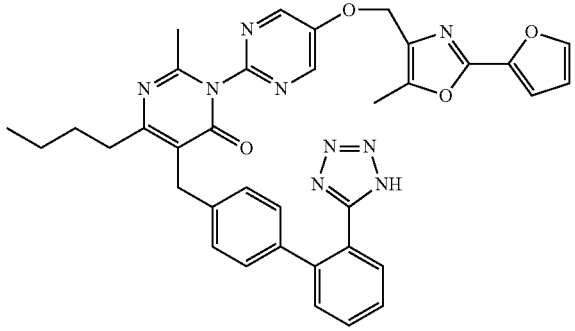 [SMILES: CCCCc1nc(C)n(-c2ncc(OCc3nc(-c4ccco4)oc3C)cn2)c(=O)c1Cc1ccc(-c2ccccc2-c2nnn[nH]2)cc1]

The N,N-dimethylformamide (1.5 mL) solution of 2-(5-bromofuran-2-yl)-4-(bromomethyl)-5-methyloxazole (32 mg, 0.1 mmol) and sodium acetate (12 g, 0.15 mmol) was stirred at 80° C. overnight. The reaction mixture was added water and extracted with ethyl acetate. The organic layer was combined, washed with water and brine, dried over anhydrous sodium sulfate, and concentrated in vacuo. The resulting residues were subjected to silica gel column chromatography (hexane/ethyl acetate) to obtain methyl {2-(5-bromofuran-2-yl)-5-methyloxazol-4-yl}acetate as a yellow oil (25 mg, 83%).

$^1$H-NMR (CDCl$_3$) δ:
2.09 (3H, s), 2.42 (3H, s), 5.00 (2H, s), 6.45 (1H, dd, J=3, 1 Hz), 6.93 (1H, dd, J=3, 1 Hz).

To the methanol (5 mL) solution of methyl {2-(5-bromofuran-2-yl)-5-methyloxazol-4-yl}acetate (420 mg, 1.4 mmol) and sodium carbonate (223 mg, 2.1 mmol), 10% Pd—C (containing 50% moisture, 210 mg) was added for 1.0 hydrogenation. After stirring at room temperature for 2 hrs, the reaction mixture was filtered through a pad of celite and washed with methanol. The filtrate was distilled off and the resulting residues were subjected to silica gel column chromatography (hexane/ethyl acetate) to obtain 2-(furan-2-yl)-5-methyloxazol-4-yl}methanol (186 mg, 76%) as a pale yellow amorphous.

$^1$H-NMR (CDCl$_3$) δ:
2.40 (3H, s), 4.58 (2H, d, J=6.0 Hz), 6.53 (1H, dd, J=3, 2 Hz), 6.97 (1H, dd, J=3, 1 Hz), 7.54 (1H, dd, J=2, 1 Hz).

The dichloromethane (1 mL) solution of {2-(furan-2-yl)-5-methyloxazol-4-yl}methanol (36 mg, 0.2 mmol), N,N-dimethylaminopyridine (37 mg, 0.3 mmol) and p-toluene sulfonyl chloride (57 mg, 0.3 mmol) was stirred at 60° C. for 2 hrs. The reaction mixture was added water and extracted with ethyl acetate. The organic layer was combined, washed with water and brine, dried over anhydrous sodium sulfate, and concentrated in vacuo. The resulting residues were subjected to silica gel column chromatography (hexane/ethyl acetate) to obtain 4-(chloromethyl)-2-(furan-2-yl)-5-methyloxazole (13 mg, 31%) as a transparent oil.

$^1$H-NMR (CDCl$_3$) δ:
2.42 (3H, s), 4.50 (2H, s), 6.52 (1H, dd, J=3, 2 Hz), 6.99 (1H, dd, J=3, 1 Hz), 7.54 (1H, dd, J=2, 1 Hz).

4'-{{4-butyl-1-{5-{[2-(furan-2-yl)-5-methyloxazol-4-yl]methoxy}pyrimidin-2-yl}-2-methyl-6-oxo-1,6-dihydropyrimidin-5-yl}methyl}biphenyl-2-carbonitrile was obtained according to the same reaction and treatment as the Process 1 of Example 21 by using 4-(chloromethyl)-2-(furan-2-yl)-5-methyloxazole instead of iodoethane.

$^1$H-NMR (CDCl$_3$) δ:
0.92 (3H, t, J=7 Hz), 1.34-1.44 (2H, m), 1.55-1.66 (2H, m), 2.16 (3H, s), 2.47 (3H, s), 2.65 (2H, t, J=8 Hz), 3.97 (2H, s), 5.15 (2H, s), 6.54 (1H, dd, J=3, 2 Hz), 7.00 (1H, d, J=3 Hz), 7.36-7.48 (6H, m), 7.55-7.64 (2H, m), 7.73 (1H, dd, J=1, 7 Hz), 8.68 (2H, s).

The target compound was obtained according to the same reaction and treatment as the Process 3 of Example 1 by using 4'-{{4-butyl-1-{5-{[2-(furan-2-yl)-5-methyloxazol-4-yl]methoxy}pyrimidin-2-yl}-2-methyl-6-oxo-1,6-dihydropyrimidin-5-yl}methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.89 (3H, t, J=7 Hz), 1.30-1.41 (2H, m), 1.54-1.66 (2H, m), 2.18 (3H, s), 2.40 (3H, s), 2.57 (2H, t, J=8 Hz), 3.83 (2H, s), 4.95 (2H, s), 6.46 (1H, dd, J=3, 2 Hz), 6.85-6.93 (3H, m), 6.97-7.04 (2H, m), 7.28-7.47 (4H, m), 7.91 (1H, brs), 8.58 (2H, s)

Example 34

Production of 5-{[2'-(1H-tetrazol-5-yl)biphenyl-4-yl]methyl}-6-butyl-2-methyl-3-{5-{[5-methyl-2-(naphthalen-2-yl)oxazol-4-yl]methoxy}pyrimidin-2-yl}-pyrimidin-4 (3H)-one

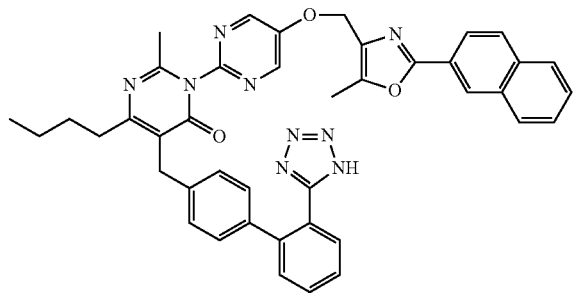 [SMILES: CCCCc1nc(C)n(-c2ncc(OCc3nc(-c4ccc5ccccc5c4)oc3C)cn2)c(=O)c1Cc1ccc(-c2ccccc2-c2nnn[nH]2)cc1]

4'-{{4-butyl-2-methyl-1-{5-{[5-methyl-2-(naphthalen-2-yl)oxazol-4-yl]methoxy}pyrimidin-2-yl}-6-oxo-1,6-dihydropyrimidin-5-yl}methyl}biphenyl-2-carbonitrile was obtained according to the same reaction and treatment as the Process 1 of Example 21 by using 4-bromomethyl-5-methyl-2-(naphthalen-2-yl)oxazole, which has been synthesized with reference to the method described in Synthesis, (17) 2825 (2004), instead of iodoethane.

$^1$H-NMR (CDCl$_3$) δ:
0.92 (3H, t, J=7 Hz), 1.35-1.45 (2H, m), 1.54-1.64 (2H, m), 2.17 (3H, s), 2.50 (3H, s), 2.65 (2H, t, J=8 Hz), 3.98 (2H, s), 5.18 (2H, s), 7.35-7.47 (6H, m), 7.51-7.61 (3H, m), 7.72 (1H, dd, J=8, 1 Hz), 7.81-7.95 (3H, m), 8.09 (1H, dd, J=9, 2 Hz), 8.50 (1H, brs), 8.74 (2H, s).

The target compound was obtained according to the same reaction and treatment as the Process 3 of Example 1 by using 4'-{{4-butyl-2-methyl-1-{5-{[5-methyl-2-(naphthalen-2-yl)oxazol-4-yl]methoxy}pyrimidin-2-yl}-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.87 (3H, t, J=7 Hz), 1.27-1.39 (2H, m), 1.54-1.66 (2H, m), 2.25 (3H, s), 2.48-2.58 (5H, m), 3.87 (2H, s), 4.96 (2H, s), 6.85 (2H, d, J=8 Hz), 7.02 (2H, d, J=8 Hz), 7.22 (1H, d, J=8 Hz), 7.34-7.56 (4H, m), 7.68-7.75 (2H, m), 7.80-7.88 (2H, m), 7.96 (1H, d, J=7 Hz), 8.31 (1H, s), 8.68 (2H, s).

Example 35

Production of 5-{[2'-(1H-tetrazol-5-yl)biphenyl-4-yl]methyl}-6-butyl-2-methyl-3-{5-[2-(5-methyl-2-phenyloxazol-4-yl)ethoxy]pyrimidin-2-yl}pyrimidin-4 (3H)-one

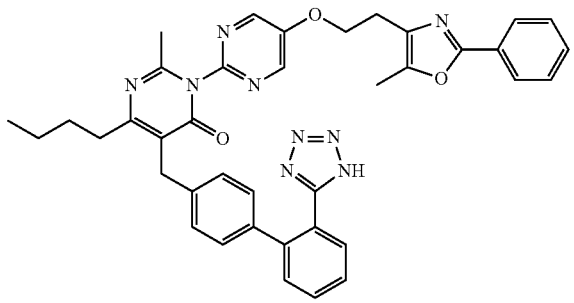 [SMILES: CCCCc1nc(C)n(-c2ncc(OCCc3nc(-c4ccccc4)oc3C)cn2)c(=O)c1Cc1ccc(-c2ccccc2-c2nnn[nH]2)cc1]

4'-{{4-butyl-2-methyl-1-{5-[(5-methyl-2-phenyloxazol-4-yl)ethoxy]pyrimidin-2-yl}-6-oxo-1,6-dihydropyrimidin-5-yl]methyl}biphenyl-2-carbonitrile was obtained according to the same reaction and treatment as the Process 1 of Example 21 by using 2-(5-methyl-2-phenyloxazol-4-yl)ethyl 4-methylbenzenesulfonate, which has been synthesized with reference to the method described in the pamphlet of International Publication No. 2008/062905, instead of iodoethane.

¹H-NMR (CDCl₃) δ:

0.92 (3H, t, J=7 Hz), 1.32-1.44 (2H, m), 1.53-1.63 (2H, m), 2.12 (3H, s), 2.40 (3H, s), 2.64 (2H, t, J=8 Hz), 3.05 (2H, t, J=7 Hz), 3.97 (2H, s), 4.46 (2H, t, J=7 Hz), 7.36-7.48 (9H, m), 7.60 (1H, td, J=8, 1 Hz), 7.73 (1H, dd, J=8, 1 Hz), 7.94-7.99 (2H, m), 8.54 (2H, s).

The target compound was obtained according to the same reaction and treatment as the Process 3 of Example 1 by using 4'-{{4-butyl-2-methyl-1-{5-[(5-methyl-2-phenyloxazol-4-yl)ethoxy]pyrimidin-2-yl}-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.90 (3H, t, J=7 Hz), 1.31-1.42 (2H, m), 1.54-1.65 (2H, m), 2.08 (3H, s), 2.37 (3H, s), 2.60 (2H, t, J=8 Hz), 2.97 (2H, t, J=6 Hz), 3.82 (2H, s), 4.38 (2H, t, J=6 Hz), 6.96 (2H, d, J=8 Hz), 7.11 (2H, d, J=8 Hz), 7.33-7.54 (6H, m), 7.88-7.97 (3H, m), 8.45 (2H, s).

Example 36

Production of 5-{[2'-(1H-tetrazol-5-yl)biphenyl-4-yl]methyl}-6-butyl-3-{5-[2-(5-ethylpyridin-2-yl)ethoxy]pyrimidin-2-yl}-2-methylpyrimidin-4 (3H)-one

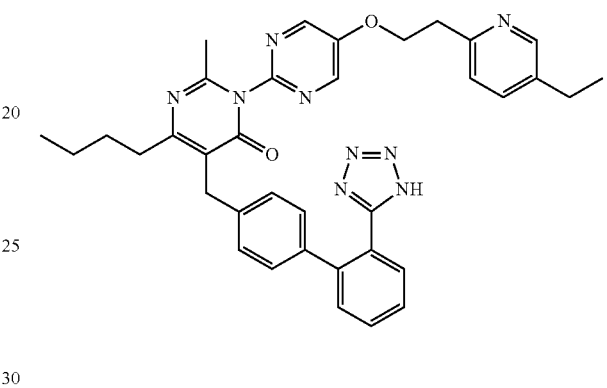

4'-{[4-butyl-1-(5-hydroxypyrimidin-2-yl)-2-methyl-6-oxo-1,6-dihydropyrimidin-5-yl]methyl}biphenyl-2-carbonitrile (50 mg, 0.111 mmol), 2-(5-ethylpyridin-2-yl)ethanol (16.8 mg, 0.111 mmol) and triphenylphosphine (44 mg, 0.167 mmol) were dried for 3 hrs in vacuo, purged with argon, added tetrahydrofuran (1 mL) and diethyl azodicarboxylic acid (2.2 mol/L toluene solution, 76 μL, 0.167 mmol), and stirred at room temperature for 2 hrs. The reaction mixture was added water and extracted with ethyl acetate. The organic layer was combined, washed with water and brine, dried over anhydrous sodium sulfate, and concentrated in vacuo. The resulting residues were subjected to silica gel column chromatography (hexane/ethyl acetate) to obtain 4'-{[4-butyl-1-{5-[2-(5-ethylpyridin-2-yl)ethoxy]pyrimidin-2-yl}-2-methyl-6-oxo-1,6-dihydropyrimidin-5-yl]methyl}biphenyl-2-carbonitrile (49 mg, 76%).

¹H-NMR (CDCl₃) δ:

0.92 (3H, t, J=7 Hz), 1.25 (3H, t, J=8 Hz), 1.32-1.45 (2H, m), 1.50-1.65 (2H, m), 2.14 (3H, s), 2.54-2.72 (4H, m), 3.30 (2H, t, J=7 Hz), 3.97 (2H, s), 4.56 (2H, t, J=7 Hz), 7.18 (1H, d, J=8 Hz), 7.32-7.52 (7H, m), 7.61 (1H, t, J=8 Hz), 7.73 (1H, d, J=8 Hz), 8.41 (1H, s), 8.52 (2H, s).

The target compound was obtained according to the same reaction and treatment as the Process 3 of Example 1 by using 4'-{{4-butyl-1-{5-[2-(5-ethylpyridin-2-yl)ethoxy]pyrimidin-2-yl}-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.90 (3H, t, J=7 Hz), 1.22 (3H, t, J=8 Hz) 1.30-1.43 (2H, m), 1.50-1.67 (2H, m), 2.12 (3H, s), 2.53-2.67 (4H, m), 3.16 (2H, t, J=6 Hz), 3.87 (2H, s), 4.48 (2H, t, J=6 Hz), 6.96 (2H, d, J=8 Hz), 7.14 (2H, d, J=8 Hz), 7.32-7.57 (5H, m), 7.95 (1H, d, J=8 Hz), 8.22 (1H, s), 8.44 (2H, s).

Example 37

Production of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}ethyl acetate

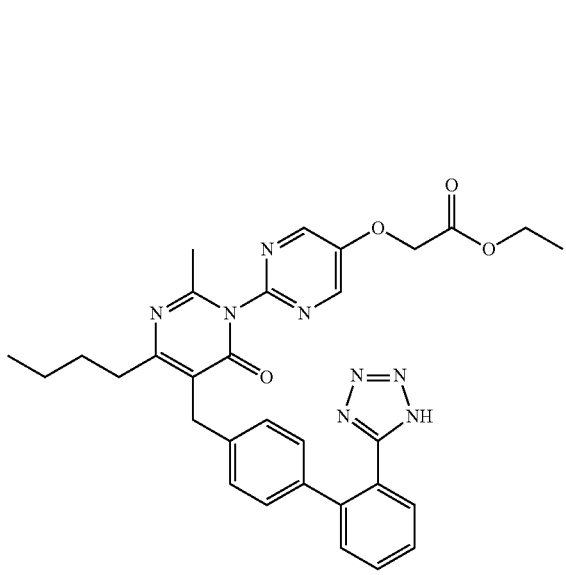 [SMILES: CCCCc1nc(C)n(-c2ncc(OCC(=O)OCC)cn2)c(=O)c1Cc1ccc(-c2ccccc2-c2nnn[nH]2)cc1]

2-{2-{(4-butyl-5-[(2'-cyanobiphenyl-4-yl)methyl]-2-methyl-6-oxopyrimidin-1(6H)-yl}pyrimidin-5-yl oxy}ethyl acetate was obtained according to the same reaction and treatment as the Process 1 of Example 21 by using bromo ethyl acetate instead of iodoethane.

¹H-NMR (CDCl₃) δ:
0.92 (3H, t, J=7 Hz), 1.31 (3H, t, J=7 Hz), 1.34-1.44 (2H, m), 1.54-1.65 (2H, m), 2.15 (3H, s), 2.65 (2H, t, J=8 Hz), 3.98 (2H, s), 4.30 (2H, q, J=7 Hz), 4.77 (2H, s), 7.35-7.48 (6H, m), 7.60 (1H, dt, J=1, 8 Hz), 7.73 (1H, dd, J=1, 8 Hz), 8.55 (2H, s).

The target compound was obtained according to the same reaction and treatment as the Process 3 of Example 1 by using 2-{2-{(4-butyl-5-[(2'-cyanobiphenyl-4-yl)methyl]-2-methyl-6-oxopyrimidin-1(6H)-yl}pyrimidin-5-yl oxy]ethyl acetate instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.92 (3H, t, J=7 Hz), 1.20-1.46 (5H, m), 1.56-1.68 (2H, m), 2.13 (3H, s), 2.64 (2H, t, J=8 Hz), 3.84 (2H, s), 4.23 (2H, q, J=7 Hz), 4.72 (2H, s), 6.96-7.06 (4H, m), 7.32-7.51 (3H, m), 7.96 (1H, brs), 8.47 (2H, brs).

Example 38

Production of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetic acid

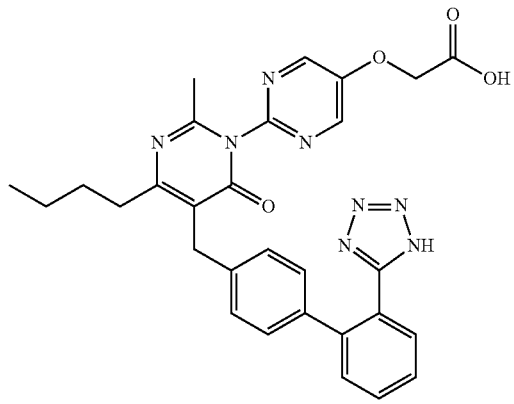 [SMILES: CCCCc1nc(C)n(-c2ncc(OCC(=O)O)cn2)c(=O)c1Cc1ccc(-c2ccccc2-c2nnn[nH]2)cc1]

To the mixture solution of tetrahydrofuran (2 mL) and water (2 mL) containing 2-{2-(5-{[2'-(1H-tetrazol-5-yl)biphenyl-4-yl]methyl}-4-butyl-2-methyl-6-oxopyrimidin-1(6H)-yl)pyrimidin-5-yl oxy}ethyl acetate (22 mg, 0.038 mmol), lithium hydroxide (8 mg, 0.29 mmol) was added and stirred at 50° C. for 1 hr. The reaction mixture was added water and extracted with chloroform. The organic layer was combined, washed with water and brine, dried over anhydrous sodium sulfate, and concentrated in vacuo. The resulting residues were subjected to silica gel column chromatography (chloroform/methanol) to obtain the target compound (15 mg, 72%) as a white solid.

¹H-NMR (CD₃OD) δ:
0.91 (3H, t, J=7 Hz), 1.32-1.41 (2H, m), 1.49-1.59 (2H, m), 2.13 (3H, s), 2.59 (2H, t, J=8 Hz), 3.87 (2H, s), 4.68 (2H, s), 7.02 (2H, d, J=8 Hz), 7.09 (2H, d, J=8 Hz), 7.38-7.55 (4H, m), 8.61 (2H, s).

Example 39

Production of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetamide

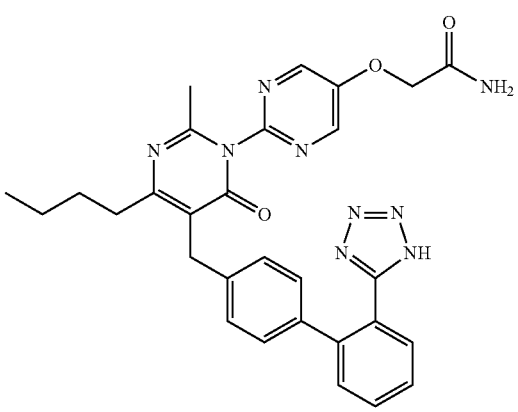 [SMILES: CCCCc1nc(C)n(-c2ncc(OCC(N)=O)cn2)c(=O)c1Cc1ccc(-c2ccccc2-c2nnn[nH]2)cc1]

Process 1: 2-{2-[4-butyl-5-[(2'-cyanobiphenyl-4-yl)methyl]-2-methyl-6-oxopyrimidin-1(6H)-yl]pyrimidin-5-yl oxy}acetic acid was obtained according to the same reaction and treatment as Example 38 by using 2-{2-{4-butyl-5-[2'-cyanobiphenyl-4-yl)methyl]-2-methyl-6-oxopyrimidin-1(6H)-yl}pyrimidin-5-yl oxy}ethyl acetate instead of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}ethyl acetate.

$^1$H-NMR (CD$_3$OD) δ:

0.90 (3H, t, J=7 Hz), 1.34-1.44 (2H, m), 1.51-1.61 (2H, m), 2.15 (3H, s), 2.66 (2H, t, J=8 Hz), 4.01 (2H, s), 4.96 (2H, s), 7.34 (2H, d, J=8 Hz), 7.45-7.59 (4H, m), 7.68-7.83 (2H, m), 8.71 (2H, s).

Process 2: The dichloromethane (3 mL) solution of 2-{2-[4-butyl-5-[(2'-cyanobiphenyl-4-yl)methyl]-2-methyl-6-oxopyrimidin-1(6H)-yl]pyrimidin-5-yl oxy}acetic acid (51 mg, 0.1 mmol), 1-ethyl-3-(3-dimethylaminopropyl)carbodiimide hydrochloride salt (29 mg, 0.15 mmol) and 1-hydroxybenzotriazol-hydrate (21 mg, 0.15 mmol) was stirred at room temperature for 1 hr. Ammonia (28% aqueous solution, 0.5 mL) was added thereto and stirred at room temperature for 4 hrs. The reaction mixture was added water and extracted with chloroform. The organic layer was combined, washed with water and brine, dried over anhydrous sodium sulfate, and concentrated in vacuo. The resulting residues were subjected to silica gel column chromatography (chloroform/methanol) to obtain 2-{2-{4-butyl-5-[(2'-cyanobiphenyl-4-yl)methyl]-2-methyl-6-oxopyrimidin-1(6H)-yl}pyrimidin-5-yl oxy}acetamide (35 mg, 69%) as a colorless and transparent oil.

$^1$H-NMR (CD$_3$OD) δ:

0.92 (3H, t, J=7 Hz), 1.35-1.45 (2H, m), 1.55-1.66 (2H, m), 2.14 (3H, s), 2.65 (2H, t, J=8 Hz), 3.97 (2H, s), 4.57 (2H, s), 6.06 (1H, brs), 6.68 (1H, brs), 7.34-7.48 (6H, m), 7.57-7.64 (1H, m), 7.73 (1H, d, J=8 Hz), 8.53 (2H, s).

Process 3: The target compound was obtained according to the same reaction and treatment as the Process 3 of Example 1 by using 2-{2-{4-butyl-5-[(2'-cyanobiphenyl-4-yl)methyl]-2-methyl-6-oxopyrimidin-1(6H)-yl]pyrimidin-5-yl oxy}acetamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CD$_3$OD) δ:

0.91 (3H, t, J=7 Hz), 1.30-1.42 (2H, m), 1.49-1.59 (2H, m), 2.13 (3H, s), 2.60 (2H, t, J=8 Hz), 3.89 (2H, s), 0.80 (2H, s), 7.02 (2H, d, J=8 Hz), 7.12 (2H, d, J=8 Hz), 7.42-7.60 (4H, m), 8.72 (2H, s). 2.13 (3H, s), 2.60 (2H, t, J=8 Hz), 3.89 (2H, s), 0.80 (2H, s), 7.02 (2H, d, J=8 Hz), 7.12 (2H, d, J=8 Hz), 7.42-7.60 (4H, m), 8.72 (2H, s).

Example 40

Production of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylacetamide

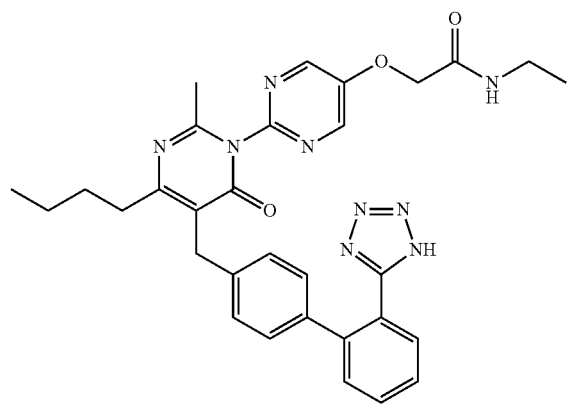 [SMILES: CCCCc1nc(C)n(-c2ncc(OCC(=O)NCC)cn2)c(=O)c1Cc1ccc(-c2ccccc2-c2nnn[nH]2)cc1]

2-{2-{4-butyl-5-[(2'-cyanobiphenyl-4-yl)methyl]-2-methyl-6-oxopyrimidin-1(6H)-yl}pyrimidin-5-yl oxy}-N-ethylacetamide was obtained according to the same reaction and treatment as the Process 2 of Example 39 by using ethylamine (70% aqueous solution) instead of ammonia.

$^1$H-NMR (CDCl$_3$) δ:

0.92 (3H, t, J=7 Hz), 1.14-1.23 (3H, m), 1.34-1.45 (2H, m), 1.55-1.66 (2H, m), 2.15 (3H, s), 2.65 (2H, t, J=8 Hz), 3.32-3.43 (2H, m), 3.98 (2H, s), 4.59 (2H, s), 6.65 (1H, brs), 7.35-7.48 (6H, m), 7.58-7.64 (1H, m), 7.73 (1H, d, J=8 Hz), 8.57 (2H, s).

The target compound was obtained according to the same reaction and treatment as the Process 3 of Example 1 by using 2-{2-{4-butyl-5-[(2'-cyanobiphenyl-4-yl)methyl]-2-methyl-6-oxopyrimidin-1(6H)-yl}pyrimidin-5-yl oxy}-N-ethylacetamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.90 (3H, t, J=7 Hz), 1.10 (3H, t, J=7 Hz), 1.30-1.43 (2H, m), 1.54-1.65 (2H, m), 2.09 (3H, s), 2.58 (2H, t, J=8 Hz), 3.22-3.34 (2H, m), 3.80 (2H, s), 4.52 (2H, s), 6.96 (2H, d, J=8 Hz), 7.05 (2H, d, J=8 Hz), 7.34-7.54 (3H, m), 7.86 (1H, d, J=8 Hz), 8.45 (2H, s).

Example 41

Production of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylacetamide

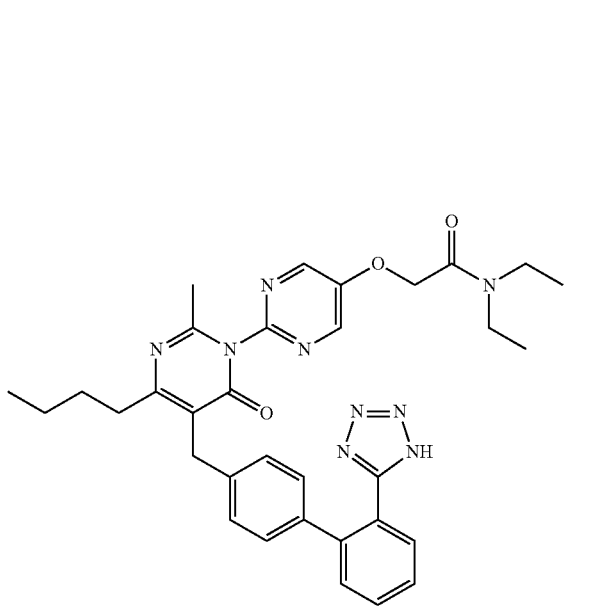 [SMILES: CCCCc1nc(C)n(-c2ncc(OCC(=O)N(CC)CC)cn2)c(=O)c1Cc1ccc(-c2ccccc2-c2nnn[nH]2)cc1]

2-{2-{4-butyl-5-[(2'-cyanobiphenyl-4-yl)methyl]-2-methyl-6-oxopyrimidin-1(6H)-yl}pyrimidin-5-yl oxy}-N,N-diethylacetamide was obtained according to the same reaction and treatment as the Process 2 of Example 39 by using diethylamine instead of ammonia.

$^1$H-NMR (CDCl$_3$) δ:

0.92 (3H, t, J=7 Hz), 1.12-1.28 (6H, m), 1.34-1.44 (2H, m), 1.55-1.65 (2H, m), 2.16 (3H, s), 2.64 (2H, t, J=8 Hz), 3.27-3.47 (4H, m), 3.97 (2H, s), 4.85 (2H, s), 7.36-7.48 (6H, m), 7.57-7.64 (1H, m), 7.73 (1H, d, J=8 Hz), 8.55 (2H, s).

The target compound was obtained according to the same reaction and treatment as the Process 3 of Example 1 by using 2-{2-{(4-butyl-5-[(2'-cyanobiphenyl-4-yl)methyl]-2-methyl-6-oxopyrimidin-1(6H)-yl}pyrimidin-5-yl oxy}-N,N-diethylacetamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.92 (3H, t, J=7 Hz), 1.09 (3H, t, J=7 Hz), 1.20 (3H, t, J=7 Hz), 1.31-1.43 (2H, m), 1.55-1.66 (2H, m), 2.12 (3H, s), 2.59 (2H, t, J=8 Hz), 3.27 (2H, q, J=7 Hz), 3.35 (2H, q, J=7 Hz), 3.79 (2H, s), 4.82 (2H, s), 6.95 (2H, d, J=8 Hz), 7.04 (2H, d, J=8 Hz), 7.32-7.52 (3H, m), 7.89 (1H, d, J=8 Hz), 8.45 (2H, s).

Example 42

Production of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetic acid

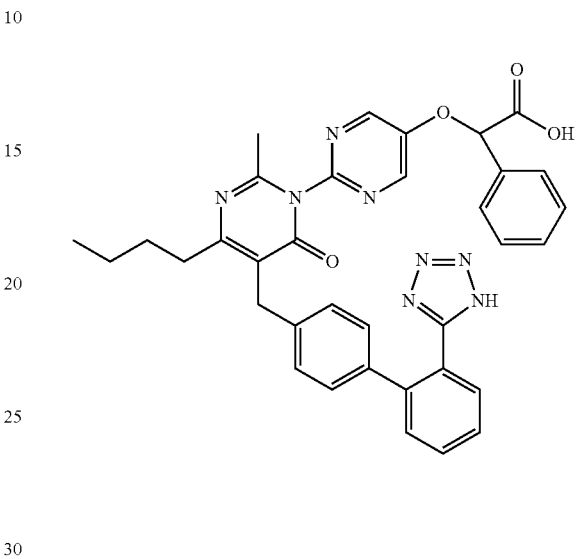

Methyl 2-{2-[4-butyl-5-[(2'-cyanobiphenyl-4-yl)methyl]-2-methyl-6-oxopyrimidin-1(6H)-yl]pyrimidin-5-yl oxy}-2-phenylacetate was obtained according to the same reaction and treatment as the Process 1 of Example 21 by using a-bromophenyl methyl acetate instead of iodoethane.

$^1$H-NMR (CDCl$_3$) δ: 0.92 (3H, t, J=7 Hz), 1.34-1.44 (2H, m), 1.55-1.65 (2H, m), 2.12 (3H, s), 2.64 (2H, t, J=8 Hz), 3.77 (3H, s), 3.97 (2H, s), 5.74 (1H, s), 7.34-7.74 (9H, m), 7.52-7.65 (3H, m), 7.72 (1H, d, J=8 Hz), 8.57 (2H, s).

2-{2-{5-{[2'-(1H-tetrazol-5-yl)biphenyl-4-yl]methyl}-4-butyl-2-methyl-6-oxopyrimidin-1,(6H)-yl}pyrimidin-5-yl oxy}-2-phenyl methyl acetate was obtained according to the same reaction and treatment as the Process 3 of Example 1 by using 2-{2-[4-butyl-5-[(2'-cyanobiphenyl-4-yl)methyl]-2-methyl-6-oxopyrimidin-1(6H)-yl]pyrimidin-5-yl oxy}-2-phenyl methyl acetate instead of 4'-{[4-butyl-2-methyl-6-oxo-1-(pyridin-2-yl)-1,6-dihydropyrimidin-5-yl]methyl}biphenyl-2-carbonitrile.

1H-NMR (CD$_3$OD) δ:

0.93 (3H, t, J=7 Hz), 1.33-1.46 (2H, m), 1.59-1.69 (2H, m), 2.12 (3H, s), 2.65 (2H, t, J=8 Hz), 3.76 (3H, s), 3.85 (2H, s), 5.77 (1H, s), 7.03 (2H, d, J=8 Hz), 7.17 (2H, d, J=8 Hz), 7.34-7.58 (8H, m), 8.05 (1H, d, J=8 Hz), 8.53 (2H, s).

The target compound was obtained according to the same reaction and treatment as Example 38 by using 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenyl methyl acetate instead of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}ethyl acetate.

$^1$H-NMR (CD$_3$OD) δ:

0.90 (3H, t, J=7 Hz), 1.30-1.41 (2H, m), 1.47-1.57 (2H, m), 2.10 (3H, s), 2.59 (2H, t, J=8 Hz), 3.24-3.47 (2H, m), 3.89 (2H, s), 5.31 (1H, dd, J=4, 8 Hz), 7.01 (2H, d, J=8 Hz), 7.16

(2H, d, J=8 Hz), 7.20-7.38 (5H, m), 7.52 (2H, t, J=8 Hz), 7.52 (2H, t, J=8 Hz), 7.61-7.68 (2H, m), 8.58 (2H, s).

Example 43

2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-3-phenylpropionic acid

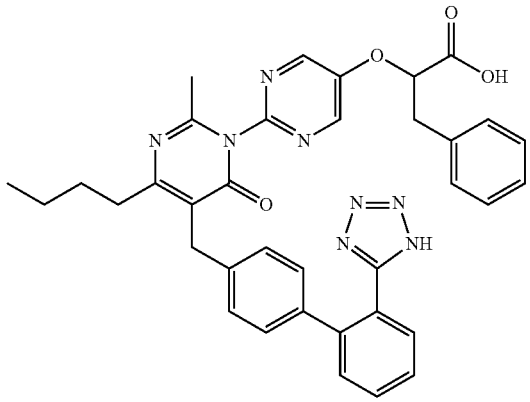 [SMILES: CCCCc1nc(C)n(-c2ncc(OC(Cc3ccccc3)C(=O)O)cn2)c(=O)c1Cc1ccc(-c2ccccc2-c2nnn[nH]2)cc1]

Methyl 2-{2-[4-butyl-5-[(2'-cyanobiphenyl-4-yl)methyl]-2-methyl-6-oxopyrimidin-1(6H)-yl]pyrimidin-5-yl Oxy}-3-phenylpropionate was obtained according to the same reaction and treatment as the Process 1 of Example 21 by using methyl 3-phenyl-2-(tosyloxy)propionate instead of iodoethane.

$^1$H-NMR (CDCl$_3$) δ:
0.92 (3H, t, J=7 Hz), 1.32-1.45 (2H, m), 1.54-1.64 (2H, m), 2.11 (3H, s), 2.64 (2H, t, J=8 Hz), 3.25-3.40 (2H, m), 3.79 (3H, s), 3.95 (2H, s), 4.90 (1H, dd, J=9, 4 Hz), 7.24-7.48 (11H, m), 7.60 (1H, td, J=8, 1 Hz), 7.77 (1H, d, J=8 Hz), 8.41 (2H, s).

Methyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-3-phenylpropionate was obtained according to the same reaction and treatment as the Process 3 of Example 1 by using methyl 2-{2-[4-butyl-5-[(2'-cyanobiphenyl-4-yl)methyl]-2-methyl-6-oxopyrimidin-1(6H)-yl]pyrimidin-5-yl oxy}-3-phenylpropionate instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.91 (3H, t, J=7 Hz), 1.31-1.44 (2H, m), 1.55-1.65 (2H, m), 2.08 (3H, s), 2.60 (2H, t, J=8.0 Hz), 3.23-3.39 (2H, m), 3.74 (3H, s), 3.81 (2H, s), 4.96 (1H, dd, J=8, 4 Hz), 6.97 (2H, d, J=8 Hz), 7.10 (2H, d, J=8 Hz), 7.24-7.54 (8H, m), 7.94 (1H, d, J=8 Hz), 8.36 (2H, s).

The target compound was obtained according to the same reaction and treatment as Example 38 by using methyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-3-phenylpropionate instead of ethyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetate.

$^1$H-NMR (CD$_3$OD) δ:
0.90 (3H, t, J=7 Hz), 1.30-1.41 (2H, m), 1.47-1.57 (2H, m), 2.10 (3H, s), 2.59 (2H, t, J=8 Hz), 3.24-3.47 (2H, m), 3.89 (2H, s), 5.31 (1H, dd, J=8, 4 Hz), 7.01 (2H, d, J=8 Hz), 7.16 (2H, d, J=8 Hz), 7.20-7.38 (5H, m), 7.52 (2H, t, J=8 Hz), 7.52 (2H, t, J=8 Hz), 7.61-7.68 (2H, m), 8.58 (2H, s).

Example 44

Production of 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetamide

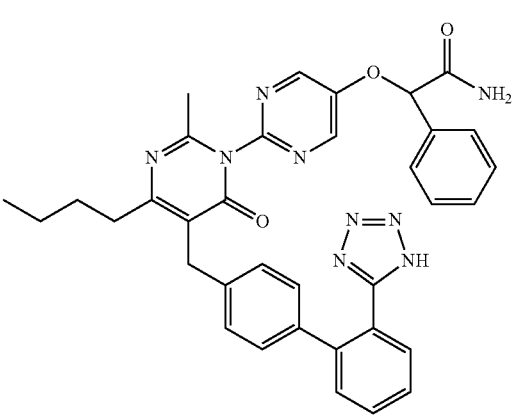 [SMILES: CCCCc1nc(C)n(-c2ncc(OC(C(N)=O)c3ccccc3)cn2)c(=O)c1Cc1ccc(-c2ccccc2-c2nnn[nH]2)cc1]

2-{2-[4-butyl-5-[(2'-cyanobiphenyl-4-yl)methyl]-2-methyl-6-oxopyrimidin-1(6H)-yl]pyrimidin-5-yl oxy}-2-phenylacetamide was obtained according to the same reaction and treatment as the Process 2 of Example 39 by using 2-{2-{4-butyl-5-[(2'-cyanobiphenyl-4-yl)methyl]-2-methyl-6-oxopyrimidin-1(6H)-yl}pyrimidin-5-yl oxy}-2-phenylacetic acid instead of 2-{2-[4-butyl-5-[(2'-cyanobiphenyl-4-yl)methyl]-2-methyl-6-oxopyrimidin-1(6H)-yl]pyrimidin-5-yl oxy}acetic acid.

$^1$H-NMR (CDCl$_3$) δ:
0.92 (3H, t, J=7 Hz), 1.32-1.45 (2H, m), 1.54-1.66(2H, m), 2.13 (3H, s), 2.64 (2H, t, J=8 Hz), 3.98 (2H, s), 5.66 (1H, s), 5.89 (1H, brs), 6.89 (1H, brs), 7.33-7.55 (11H, m), 7.59 (1H, t, J=8 Hz), 7.72 (1H, d, J=8 Hz), 8.53 (2H, s).

The target compound was obtained according to the same reaction and treatment as the Process 3 of Example 1 by using 2-{2-[4-butyl-5-[(2'-cyanobiphenyl-4-yl)methyl]-2-methyl-6-oxopyrimidin-1(6H)-yl]pyrimidin-5-yl oxy}-2-phenylacetamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CD$_3$Cl$_3$) δ:
0.90 (3H, t, J=7 Hz), 1.29-1.42 (2H, m), 1.52-1.66 (2H, m), 2.08 (3H, s), 2.53-2.62 (2H, m), 3.79 (2H, s), 5.64 (1H, s), 6.12 (1H, brs), 6.92 (3H, brs), 7.20-7.49 (10H, m), 7.86 (1H, brs), 8.39 (2H, s).

Example 45

Production of ethyl 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanoate

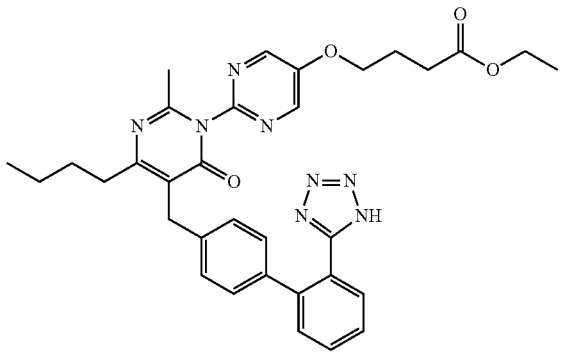 [SMILES: CCCCc1nc(C)n(-c2ncc(OCCCC(=O)OCC)cn2)c(=O)c1Cc1ccc(-c2ccccc2-c2nnn[nH]2)cc1]

Ethyl 4-{2-{(4-butyl-5-[(2'-cyanobiphenyl-4-yl)methyl]-2-methyl-6-oxopyrimidin-1(6H)-yl}pyrimidin-5-yl oxy}butanoate was obtained according to the same reaction and treatment as the Process 1 of Example 21 by using ethyl 4-bromobutanoate instead of iodoethane.

¹H-NMR (CDCl₃) δ:
0.92 (3H, t, J=7 Hz), 1.27 (3H, t, J=7 Hz), 1.34-1.45 (2H, m), 1.55-1.65 (2H, m), 2.15-2.21 (5H, m), 2.54 (2H, t, J=7 Hz), 2.65 (2H, t, J=8 Hz), 3.98 (2H, s), 4.13-4.24 (4H, m), 7.35-7.49 (6H, m), 7.61 (1H, td, J=8, 1 Hz), 7.73 (1H, dd, J=8, 1 Hz), 8.53 (2H, s).

The target compound was obtained according to the same reaction and treatment as the Process 3 of Example 1 by using ethyl 4-{2-{4-butyl-5-[(2'-cyanobiphenyl-4-yl)methyl]-2-methyl-6-oxopyrimidin-1(6H)-yl}pyrimidin-5-yl oxy}butanoate instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.89 (3H, t, J=7 Hz), 1.24 (3H, t, J=7 Hz), 1.30-1.40 (2H, m), 1.50-1.66 (2H, m), 2.06-2.16 (5H, m), 2.44-2.62 (4H, m), 3.77 (2H, s), 4.08-4.18 (4H, m), 6.81-6.94 (2H, m), 6.96-7.08 (2H, m), 7.32-7.52 (3H, m), 7.81 (1H, brs), 8.41 (2H, s).

Example 46

Production of 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanoic acid

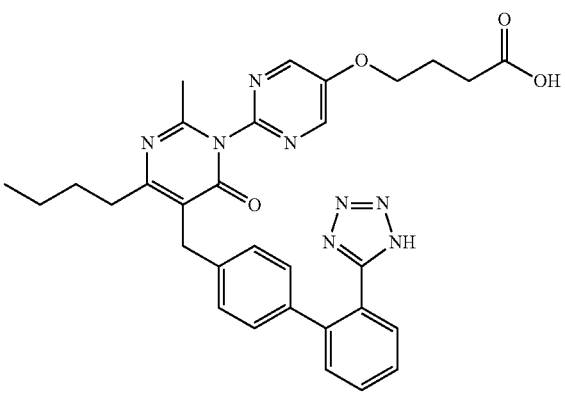 [SMILES: CCCCc1nc(C)n(-c2ncc(OCCCC(=O)O)cn2)c(=O)c1Cc1ccc(-c2ccccc2-c2nnn[nH]2)cc1]

The target compound was obtained according to the same reaction and treatment as Example 38 by using ethyl 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanoate instead of ethyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetate.

¹H-NMR (CDCl₃) δ:
0.90 (3H, t, J=7 Hz), 1.31-1.42 (2H, m), 1.54-1.64 (2H, m), 2.10 (3H, s), 2.10-2.18 (2H, m), 2.52 (2H, t, J=7 Hz), 2.60 (2H, t, J=8 Hz), 3.84 (2H, s), 4.19 (2H, t, J=6 Hz), 7.00 (2H, d, J=8 Hz), 7.14 (2H, d, J=8 Hz), 7.36-7.58 (3H, m), 7.90 (1H, d, J=8 Hz), 8.45 (2H, s).

Example 47

Production of 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanamide

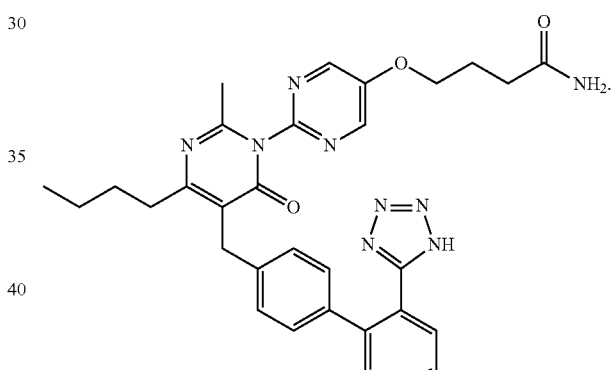

Process 1: 4-{2-[4-butyl-5-[(2'-cyanobiphenyl-4-yl)methyl]-2-methyl-6-oxopyrimidin-1(6H)-yl]pyrimidin-5-yl oxy}butanoic acid was obtained according to the same reaction and treatment as Example 38 by using ethyl 4-{2-{4-butyl-5-[(2'-cyanobiphenyl-4-yl)methyl]-2-methyl-6-oxopyrimidin-1(6H)-yl}pyrimidin-5-yl oxy}butanoate instead of ethyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetate.

¹H-NMR (CD₃OD) δ:
0.90 (3H, t, J=7 Hz), 1.31-1.42 (2H, m), 1.51-1.60 (2H, m), 2.13-2.20 (5H, s), 2.53 (2H, t, J=7 Hz), 2.66 (2H, t, J=8 Hz), 4.01 (2H, s), 4.30 (2H, t, J=6 Hz), 7.37 (2H, d, J=8 Hz), 7.45-7.58 (4H, m), 7.71 (1H, td, J=8, 1 Hz), 7.80 (1H, dd, J=8, 1 Hz), 8.69 (2H, s).

Process 2: 4-{2-{4-butyl-5-[(2'-cyanobiphenyl-4-yl)methyl]-2-methyl-6-oxopyrimidin-1(6H)-yl}pyrimidin-5-yl oxy}butanamide was obtained according to the same reaction and treatment as the Process 2 of Example 39 by using 4-{2-[4-butyl-5-[(2'-cyanobiphenyl-4-yl)methyl]-2-methyl-6-oxopyrimidin-1(6H)-yl]pyrimidin-5-yl oxy}butanoic acid instead of 2-{2-[4-butyl-5-[(2'-cyanobiphenyl-4-yl)methyl]-2-methyl-6-oxopyrimidin-1(6H)-yl]pyrimidin-5-yl oxy}acetic acid.

$^1$H-NMR (CD$_3$OD) δ:

0.92 (3H, t, J=7 Hz), 1.34-1.45 (2H, m), 1.55-1.66 (2H, m), 2.14-2.18 (5H, m), 2.38 (2H, t, J=6 Hz), 2.64 (2H, t, J=8 Hz), 3.97 (2H, s), 4.19 (2H, t, J=6 Hz), 5.72 (1H, brs), 5.89 (1H, brs), 7.34-7.49 (6H, m), 7.61 (1H, dt, J=1, 8 Hz), 7.73 (1H, dd, J=1, 8 Hz), 8.52 (2H, s).

Process 3: The target compound was obtained according to the same reaction and treatment as the Process 3 of Example 1 by using 4-{2-{4-butyl-5-[(2'-cyanobiphenyl-4-yl)methyl]-2-methyl-6-oxopyrimidin-1(6H)-yl}pyrimidin-5-yl oxy}butanamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR(CD$_3$OD) δ:

0.90 (3H, t, J=7 Hz), 1.30-1.41 (2H, m), 1.48-1.59 (2H, m), 2.10-2.19 (5H, m), 2.44 (2H, t, J=7 Hz), 2.59 (2H, t, J=8 Hz), 3.89 (2H, s), 4.27 (2H, t, J=6 Hz), 7.02 (2H, d, J=8 Hz), 7.14 (2H, d, J=8 Hz), 7.44-7.62 (4H, m), 8.67 (2H, s).

Example 48

Production of 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-methylbutanamide

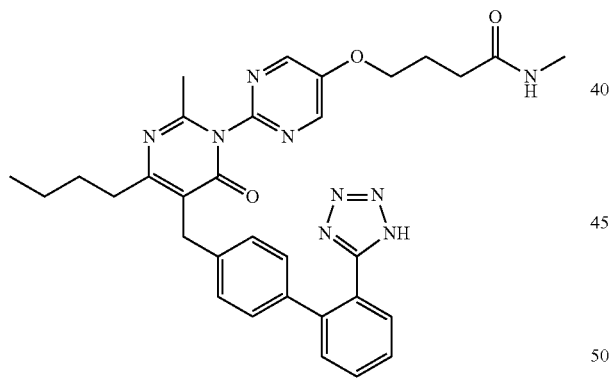

4-{2-{4-butyl-5-[(2'-cyanobiphenyl-4-yl)methyl]-2-methyl-6-oxopyrimidin-1(6H)-yl}pyrimidin-5-yl oxy}-N-methylbutanamide was obtained according to the same reaction and treatment as the Process 2 of Example 47 by using methylamine (2 mol/L tetrahydrofuran solution) instead of ammonia.

$^1$H-NMR (CDCl$_3$) δ:

0.84 (3H, t, J=7 Hz), 1.26-1.37 (2H, m), 1.45-1.57 (2H, m), 2.08-2.16 (5H, m), 2.31 (2H, t, J=7 Hz), 2.55-2.65 (2H, m), 2.71 (3H, s), 3.89 (2H, s), 4.13 (2H, t, J=6 Hz), 6.20 (1H, brs), 7.28-7.42 (6H, m), 7.51-7.59 (1H, m), 7.66 (1H, d, J=8 Hz), 8.45 (2H, s).

The target compound was obtained according to the same reaction and treatment as the Process 3 of Example 1 by using 4-{2-{4-butyl-5-[(2'-cyanobiphenyl-4-yl)methyl]-2-methyl-6-oxopyrimidin-1(6H)-yl}pyrimidin-5-yl oxy}-N-methylbutanamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CD$_3$OD) δ:

0.91 (3H, t, J=7 Hz), 1.34-1.44 (2H, m), 1.55-1.66 (2H, m), 1.92-1.99 (2H, m), 2.10 (3H, s), 2.14-2.20 (2H, m), 2.54-2.70 (5H, m), 3.81 (2H, m), 3.92-3.98 (2H, m), 6.84 (1H, brs), 6.96 (2H, d, J=8 Hz), 7.01 (2H, d, J=8 Hz), 7.31-7.48 (3H, m), 7.76-7.83 (1H, m), 8.31 (2H, s).

Example 49

Production of 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylbutanamide

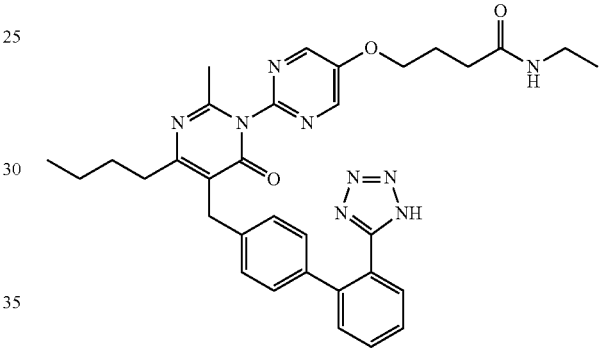

4-{2-{4-butyl-5-[(2'-cyanobiphenyl-4-yl)methyl]-2-methyl-6-oxopyrimidin-1(6H)-yl}pyrimidin-5-yl oxy}-N-ethylbutanamide was obtained according to the same reaction and treatment as the Process 2 of Example 47 by using ethylamine (70% aqueous solution) instead of ammonia.

$^1$H-NMR (CDCl$_3$) δ:

0.92 (3H, t, J=7 Hz), 1.12 (3H, t, J=7 Hz), 1.33-1.45 (2H, m), 1.54-1.65 (2H, m), 2.14-2.22 (5H, m), 2.35 (2H, t, J=7 Hz), 2.65 (2H, t, J=8 Hz), 3.21-3.33 (2H, m), 3.97 (2H, s), 4.20 (2H, t, J=6 Hz), 5.74 (1H, brs), 7.34-7.49 (6H, m), 7.61 (1H, td, J=9, 1 Hz), 7.73 (1H, dd, J=8, 1 Hz), 8.52 (2H, s).

The target compound was obtained according to the same reaction and treatment as the Process 3 of Example 1 by using 4-{2-{4-butyl-5-[(2'-cyanobiphenyl-4-yl)methyl]-2-methyl-6-oxopyrimidin-1(6H)-yl}pyrimidin-5-yl oxy}-N-ethylbutanamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.91 (3H, t, J=7 Hz), 1.03 (3H, t, J=7 Hz), 1.32-1.44 (2H, m), 1.56-1.66 (2H, m), 2.02-2.14 (5H, m), 2.23 (2H, t, J=7 Hz), 2.60 (2H, t, J=8 Hz), 3.10-3.21 (2H, m), 3.83 (2H, m), 4.03-4.12 (2H, m), 6.45 (1H, brs), 6.97 (2H, d, J=8 Hz), 7.06 (2H, d, J=8 Hz), 7.34-7.54 (3H, m), 7.87 (1H, d, J=7 Hz), 8.38 (2H, s).

Example 50

Production of 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-propylbutanamide

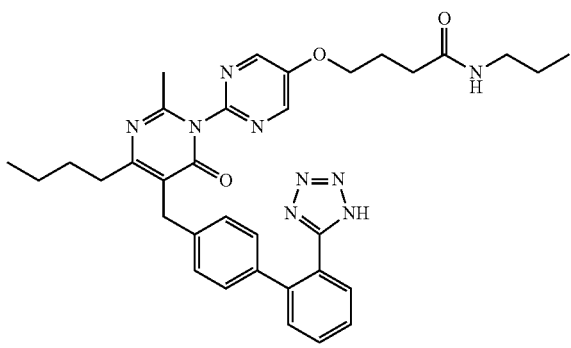 [SMILES: CCCCc1nc(C)n(-c2ncc(OCCCC(=O)NCCC)cn2)c(=O)c1Cc1ccc(-c2ccccc2-c2nnn[nH]2)cc1]

4-{2-{4-butyl-5-[(2'-cyanobiphenyl-4-yl)methyl]-2-methyl-6-oxopyrimidin-1(6H)-yl}pyrimidin-5-yl oxy}-N-propylbutanamide was obtained according to the same reaction and treatment as the Process 2 of Example 47 by using propylamine instead of ammonia.

$^1$H-NMR (CDCl$_3$) δ:

0.86-0.96 (6H, m), 1.34-1.45 (2H, m), 1.51-1.65 (4H, m), 2.13-2.24 (5H, m), 2.38 (2H, t, J=7 Hz), 2.65 (2H, t, J=8 Hz), 3.19-3.29 (2H, m), 3.97 (2H, s), 4.21 (2H, t, J=6 Hz), 5.62 (1H, brs), 7.35-7.48 (6H, m), 7.61 (1H, td, J=8, 1 Hz), 7.74 (1H, dd, J=8, 1 Hz), 8.53 (2H, s). The target compound was obtained according to the same reaction and treatment as the Process 3 of Example 1 by using 4-{2-{4-butyl-5-[(2'-cyanobiphenyl-4-yl)methyl]-2-methyl-6-oxopyrimidin-1(6H)-yl]pyrimidin-5-yl oxy]-N-propylbutanamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.84 (3H, t, J=7 Hz), 0.92 (3H, t, J=7 Hz), 1.34-1.48 (4H, m), 1.55-1.68 (2H, m), 2.01-2.10 (2H, m), 2.13 (3H, s), 2.22-2.29 (2H, m), 2.64 (2H, t, J=8 Hz), 3.07-3.15 (2H, m), 3.84 (2H, s), 4.01-4.10 (2H, m), 6.38 (1H, brs), 7.00 (2H, d, J=8 Hz), 7.09 (2H, d, J=8 Hz), 7.35-7.52 (3H, m), 7.86-7.94 (1H, m), 8.39 (2H, s).

Example 51

Production of 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-isopropylbutanamide

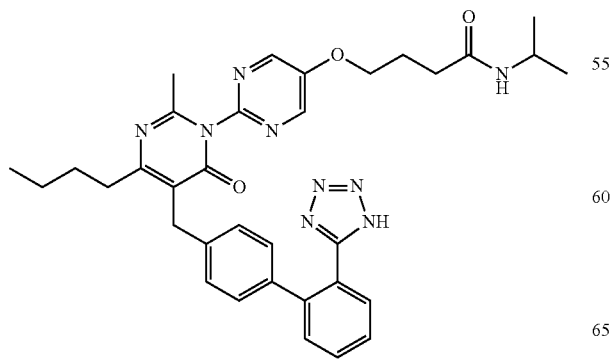

4-{2-{4-butyl-5-[(2'-cyanobiphenyl-4-yl)methyl]-2-methyl-6-oxopyrimidin-1(6H)-yl}pyrimidin-5-yl oxy}-N-isopropylbutanamide was obtained according to the same reaction and treatment as the Process 2 of Example 47 by using isopropylamine instead of ammonia.

$^1$H-NMR (CDCl$_3$) δ:

0.92 (3H, t, J=7 Hz), 1.15 (6H, t, J=7 Hz), 1.34-1.45 (2H, m), 1.55-1.66 (2H, m), 2.14-2.24 (5H, m), 2.35 (2H, t, J=7 Hz), 2.65 (2H, t, J=8 Hz), 3.97 (2H, s), 4.03-4.16 (1H, m), 4.21 (2H, t, J=6 Hz), 5.43 (1H, brs), 7.35-7.49 (6H, m), 7.61 (1H, td, J=8, 1 Hz), 7.74 (1H, dd, J=8, 1 Hz), 8.53 (2H, s).

The target compound was obtained according to the same reaction and treatment as the Process 3 of Example 1 by using 4-{2-{4-butyl-5-[(2'-cyanobiphenyl-4-yl)methyl]-2-methyl-6-oxopyrimidin-1(6H)-yl]pyrimidin-5-yl oxy]-N-isopropylbutanamide instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.92 (3H, t, J=7 Hz), 1.08 (6H, d, J=6 Hz), 1.34-1.44 (2H, m), 1.56-1.68 (2H, m), 2.02-2.11 (2H, m), 2.12 (3H, s), 2.21-2.26 (2H, m), 2.64 (2H, t, J=8 Hz), 3.84 (2H, s), 3.94-4.13 (3H, m), 6.11 (1H, brs), 7.00 (2H, d, J=8 Hz), 7.10 (2H, d, J=8 Hz), 7.33-7.54 (3H, m), 7.90 (1H, d, J=7 Hz), 8.41 (2H, s).

Example 52

Production of 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylbutanamide

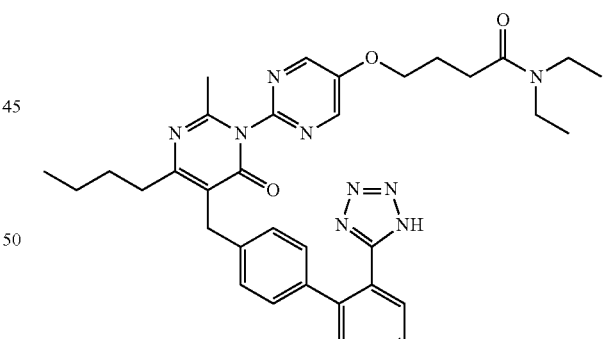

4-{2-{4-butyl-5-[(2'-cyanobiphenyl-4-yl)methyl]-2-methyl-6-oxopyrimidin-1 (6H)-yl}pyrimidin-5-yl oxy}-N,N-diethylbutanamide was obtained according to the same reaction and treatment as the Process 2 of Example 47 by using diethylamine instead of ammonia.

¹H-NMR (CDCl₃) δ:

0.92 (3H, t, J=7 Hz), 1.13 (3H, t, J=7 Hz), 1.19 (3H, t, J=7 Hz), 1.33-1.45 (2H, m), 1.55-1.68 (2H, m), 2.16 (3H, s), 2.19-2.26 (2H, m), 2.53 (2H, t, J=7 Hz), 2.65 (2H, t, J=8 Hz), 3.29-3.43 (4H, m), 3.97 (2H, s), 4.25 (2H, t, J=6 Hz), 7.35-7.48 (6H, m), 7.61 (1H, td, J=8, 1 Hz), 7.73 (1H, d, J=8 Hz), 8.54 (2H, s).

The target compound was obtained according to the same reaction and treatment as the Process 3 of Example 1 by using 4-{2-{4-butyl-5-[(2'-cyanobiphenyl-4-yl)methyl]-2-methyl-6-oxopyrimidin-1(6H)-yl]pyrimidin-5-yl oxy]-N,N-diethylbutanamide instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.91 (3H, t, J=7 Hz), 1.08 (3H, t, J=7 Hz), 1.16 (3H, t, J=7 Hz), 1.32-1.46 (2H, m), 1.55-1.66 (2H, m), 2.06-2.15 (5H, m), 2.46 (2H, t, J=7 Hz), 2.61 (2H, t, J=8 Hz), 3.26-3.38 (4H, m), 3.83 (2H, m), 4.12-4.19 (2H, m), 6.97 (2H, d, J=7 Hz), 7.10 (2H, d, J=7 Hz), 7.33-7.52 (3H, m), 7.92 (1H, brs), 8.44 (2H, s).

Example 53

Production of 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}pentanamide

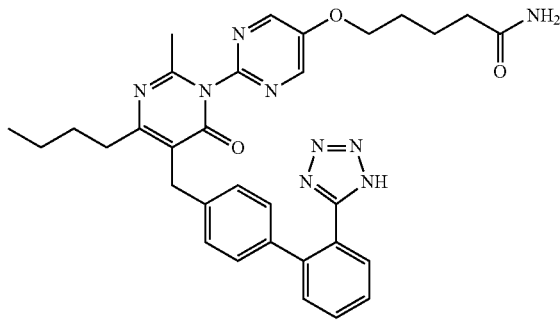 [SMILES: CCCCc1nc(C)n(-c2ncc(OCCCCC(N)=O)cn2)c(=O)c1Cc1ccc(-c2ccccc2-c2nnn[nH]2)cc1]

Process 1: Ethyl 5-{2-[4-butyl-5-[(2'-cyanobiphenyl-4-yl)methyl]-2-methyl-6-oxopyrimidin-1(6H)-yl]pyrimidin-5-yl oxy}pentanoate was obtained according to the same reaction and treatment as the Process 1 of Example 21 by using ethyl 5-bromopentanoate instead of iodoethane.

¹H-NMR (CDCl₃) δ:

0.93 (3H, t, J=7 Hz), 1.27 (3H, t, J=7 Hz), 1.34-1.44 (2H, m), 1.55-1.65 (2H, m), 1.75-1.96 (4H, m), 2.16 (3H, s), 2.41 (2H, t, J=7 Hz), 2.65 (2H, t, J=8 Hz), 3.98 (2H, s), 4.11-4.19 (4H, m), 7.34-7.49 (6H, m), 7.61 (1H, t, J=8 Hz), 7.73 (1H, d, J=8 Hz), 8.52 (2H, s).

Process 2: 5-{2-[4-butyl-5-[(2'-cyanobiphenyl-4-yl)methyl]-2-methyl-6-oxopyrimidin-1(6H)-yl]pyrimidin-5-yl oxy}pentanoic acid was obtained according to the same reaction and treatment as Example 38 by using ethyl 5-{2-[4-butyl-5-[(2'-cyanobiphenyl-4-yl)methyl]-2-methyl-6-oxopyrimidin-1(6H)-yl]pyrimidin-5-yl oxy}pentanoate instead of ethyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetate.

¹H-NMR (CD₃OD) δ:

0.88 (3H, t, J=7 Hz), 1.31-1.41 (2H, m), 1.49-1.59 (2H, m), 1.76-1.95 (4H, m), 2.12 (3H, s), 2.39 (2H, t, J=7 Hz), 2.63 (2H, t, J=8 Hz), 3.99 (2H, s), 4.22 (2H, t, J=6 Hz), 7.34-7.54 (6H, m), 7.66 (1H, td, J=8, 1 Hz), 7.77 (1H, dd, J=8, 1 Hz), 8.64 (2H, s).

Process 3: 5-{2-{4-butyl-5-[(2'-cyanobiphenyl-4-yl)methyl]-2-methyl-6-oxopyrimidin-1(6H)-yl}pyrimidin-5-yl oxy}pentanamide was obtained according to the same reaction and treatment as the Process 2 of Example 39 by using 5-{2-[4-butyl-5-[(2'-cyanobiphenyl-4-yl)methyl]-2-methyl-6-oxopyrimidin-1(6H)-yl]pyrimidin-5-yl oxy}pentanoic acid instead of 2-{2-[4-butyl-5-[(2'-cyanobiphenyl-4-yl)methyl]-2-methyl-6-oxopyrimidin-1(6H)-yl]pyrimidin-5-yl oxy}acetic acid.

¹H-NMR (CD₃OD) δ:

0.92 (3H, t, J=7 Hz), 1.33-1.44 (2H, m), 1.54-1.66 (2H, m), 1.80-1.95 (4H, m), 2.16 (3H, s), 2.25-2.32 (2H, m), 2.65 (2H, t, J=8 Hz), 3.97 (2H, s), 4.11-4.17 (2H, m), 5.65 (1H, brs), 5.78 (1H, brs), 7.35-7.49 (6H, m), 7.57-7.64 (1H, m), 7.73 (1H, d, J=8 Hz), 8.52 (2H, s).

Process 4: The target compound was obtained according to the same reaction and treatment as the Process 3 of Example 1 by using 5-{2-{4-butyl-5-[(2'-cyanobiphenyl-4-yl)methyl]-2-methyl-6-oxopyrimidin-1(6H)-yl}pyrimidin-5-yl oxy}pentanamide instead of 4'-{[4-butyl-2-methyl-6-oxo-1-(pyridin-2-yl)-1,6-dihydropyrimidin-5-yl]methyl}biphenyl-2-carbonitrile.

¹H-NMR (CD₃OD) δ: 0.90 (3H, t, J=7 Hz), 1.31-1.41 (2H, m), 1.43-1.66 (6H, m), 1.94-2.02 (2H, m), 2.09 (3H, s), 2.58 (2H, t, J=8 Hz), 3.76-3.86 (4H, m), 6.08 (1H, brs), 6.78 (1H, brs), 6.90-7.01 (4H, m), 7.26-7.44 (3H, m), 7.74 (1H, d, J=7 Hz), 8.29 (2H, s).

Example 54

Production of 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylpentanamide

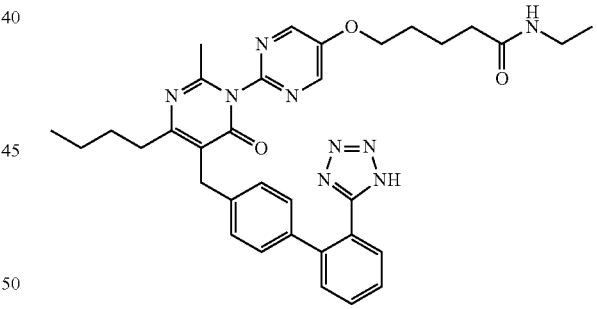

5-{2-{4-butyl-5-[(2'-cyanobiphenyl-4-yl)methyl]-2-methyl-6-oxopyrimidin-1(6H)-yl}pyrimidin-5-yl oxy}-N-ethylpentanamide was obtained according to the same reaction and treatment as the Process 3 of Example 53 by using ethylamine (70% aqueous solution) instead of ammonia.

¹H-NMR (CDCl₃) δ:

0.92 (3H, t, J=7 Hz), 1.13 (3H, t, J=7 Hz), 1.34-1.45 (2H, m), 1.54-1.65 (2H, m), 1.80-1.93 (4H, m), 2.16 (3H, s), 2.23 (2H, t, J=7 Hz), 2.65 (2H, t, J=8 Hz), 3.23-3.20 (2H, m), 3.98 (2H, s), 4.15 (2H, t, J=6 Hz), 5.77 (1H, brs), 7.35-7.49 (6H, m), 7.61 (1H, td, J=8, 1 Hz), 7.74 (1H, dd, J=8, 1 Hz), 8.51 (2H, s).

The target compound was obtained according to the same reaction and treatment as the Process 3 of Example 1 by using 5-{2-{4-butyl-5-[(2'-cyanobiphenyl-4-yl)methyl]-2-methyl- 6-oxopyrimidin-1(6H)-yl}pyrimidin-5-yl oxy}-N-ethylpentanamide instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.91 (3H, t, J=7 Hz), 1.04 (3H, t, J=7 Hz), 1.34-1.43 (2H, m), 1.57-1.67 (2H, m), 1.70-1.82 (4H, m), 2.08-2.14 (5H, m), 2.60 (2H, t, J=8 Hz), 3.12-3.20 (2H, m), 3.84 (2H, s), 3.98-4.07 (2H, m), 6.44 (1H, brs), 6.97 (2H, d, J=8 Hz), 7.06 (2H, d, J=8 Hz), 7.34-7.53 (3H, m), 7.84 (1H, d, J=7 Hz), 8.40 (2H, s).

Example 55

Production of 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylpentanamide

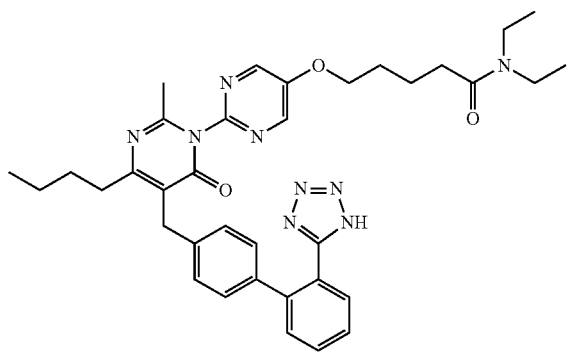 [SMILES: CCCCc1nc(C)n(-c2ncc(OCCCCC(=O)N(CC)CC)cn2)c(=O)c1Cc1ccc(-c2ccccc2-c2nnn[nH]2)cc1]

5-{2-{4-butyl-5-[(2'-cyanobiphenyl-4-yl)methyl]-2-methyl-6-oxopyrimidin-1(6H)-yl}pyrimidin-5-yl oxy}-N,N-diethylpentanamide was obtained according to the same reaction and treatment as the Process 3 of Example 53 by using diethylamine instead of ammonia.

¹H-NMR (CDCl₃) δ:

0.92 (3H, t, J=7 Hz), 1.12 (3H, t, J=7 Hz), 1.19 (3H, t, J=7 Hz), 1.34-1.45 (2H, m), 1.55-1.65 (2H, m), 1.83-1.97 (4H, m), 2.16 (3H, s), 2.39 (2H, t, J=7 Hz), 2.65 (2H, t, J=8 Hz), 3.28-3.42 (4H, m), 3.97 (2H, s), 4.18 (2H, t, J=6 Hz), 7.36-7.49 (6H, m), 7.61 (1H, td, J=8, 1 Hz), 7.73 (1H, dd, J=8, 1 Hz), 8.52 (2H, s).

The target compound was obtained according to the same reaction and treatment as the Process 3 of Example 1 by using 5-{2-{4-butyl-5-[(2'-cyanobiphenyl-4-yl)methyl]-2-methyl-6-oxopyrimidin-1(6H)-yl}pyrimidin-5-yl oxy}-N,N-diethylpentanamide instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.92 (3H, t, J=7 Hz), 1.08 (3H, t, J=7 Hz), 1.18 (3H, t, J=7 Hz), 1.35-1.45 (2H, m), 1.57-1.67 (2H, m), 1.75-1.91 (4H, m), 2.14 (3H, s), 2.35 (2H, t, J=7 Hz), 2.64 (2H, t, J=8 Hz), 3.28-3.37 (4H, m), 3.87 (2H, s), 4.06-4.15 (2H, m), 7.03 (2H, d, J=8 Hz), 7.17 (2H, d, J=8 Hz), 7.36-7.56 (3H, m), 7.98 (1H, d, J=8 Hz), 8.46 (2H, s).

Example 56

Production of N-{3-{2-{5-{[2'-(1H-tetrazol-5-yl)biphenyl-4-yl]methyl}-4-butyl-2-methyl-6-oxopyrimidin-1 (6H)-yl}pyrimidin-5-yl oxy}propyl}acetamide

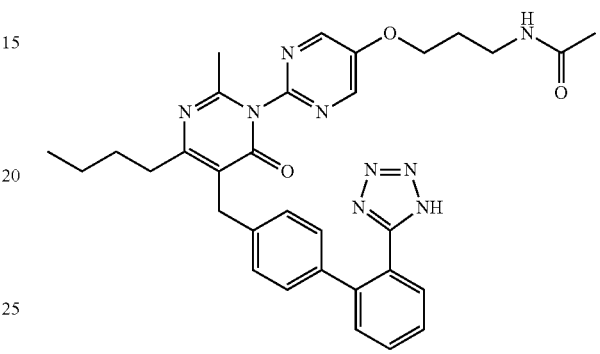

Process 1: Tert-butyl 3-{2-{4-butyl-5-[(2'-cyanobiphenyl-4-yl)methyl]-2-methyl-6-oxopyrimidin-1(6H)-yl}pyrimidin-5-yl oxy}propyl carbamate was obtained according to the same reaction and treatment as the Process 1 of Example 21 by using N-(3-bromopropyl)-tert-butyl carbamate instead of iodoethane.

¹H-NMR (CDCl₃) δ:

0.92 (3H, t, J=7 Hz), 1.33-1.48 (11H, m), 1.55-1.65 (2H, m), 2.04-2.09 (2H, m), 2.16 (3H, s), 2.65 (2H, t, J=8 Hz), 3.32-3.39 (2H, m), 3.97 (2H, s), 4.19 (2H, t, J=6 Hz), 4.77 (1H, brs), 7.36-7.49 (6H, m), 7.61 (1H, t, J=8 Hz), 7.74 (1H, d, J=8 Hz), 8.53 (2H, s).

Process 2: To the ethyl acetate (2 mL) solution of tert-butyl (3-{2-{4-butyl-5-[(2'-cyanobiphenyl-4-yl)methyl]-2-methyl-6-oxopyrimidin-1(6H)-yl}pyrimidin-5-yl oxy}propylcarbamate (183 mg, 0.3 mmol), hydrochloric acid mol/L ethyl acetate solution) was added and stirred at room temperature for 24 hrs. The reaction mixture was added saturated sodium hydrogen carbonate solution and extracted with ethyl acetate. The organic layer was combined, washed with water and brine, and dried over anhydrous sodium sulfate. The solvent was distilled off to obtain 4'-{{1-[5-(3-aminopropoxy)pyrimidin-2-yl]-4-butyl-2-methyl-6-oxo-1,6-dihydropyrimidin-5-yl}methyl}biphenyl-2-carbonitrile (153 mg) as a crude product.

¹H-NMR (CDCl₃) δ:

0.92 (3H, t, J=7 Hz), 1.33-1.44 (2H, m), 1.53-1.65 (2H, m), 1.92-2.04 (2H, m), 2.16 (3H, s), 2.65 (2H, t, J=8 Hz), 2.90-2.98 (2H, m), 3.97 (2H, s), 4.24 (2H, t, J=6 Hz), 7.35-7.48 (6H, m), 7.61 (1H, td, J=8, 1 Hz), 7.74 (1H, dd, J=8, 1 Hz), 8.54 (2H, s).

Process 3: To the dichloromethane (1 mL) solution of the crude product of 4'-{{1-[5-(3-aminopropoxy)pyrimidin-2-yl]-4-butyl-2-methyl-6-oxo-1,6-dihydropyrimidin-5-yl}methyl}biphenyl-2-carbonitrile (45 mg), pyridine (9.7 mg, 0.123 mmol) and acetyl chloride (8.3 mg, 0.106 mmol) were added and stirred at room temperature overnight. The reaction mixture was added water, and extracted with ethyl acetate. The organic layer was combined, washed with water and brine, and dried over anhydrous sodium sulfate. The solvent was distilled off to obtain N-{3-{2-{4-butyl-5-[(2'-cyanobiphenyl-4-yl)methyl]-2-methyl-6-oxopyrimidin-1(6H)-yl}pyrimidin-5-yl oxy}propyl}acetamide (35 mg) as a crude product.

Process 4: The target compound was obtained according to the same reaction and treatment as the Process 3 of Example 1 by using the crude product of N-{3-{2-{4-butyl-5-[(2'-cyanobiphenyl-4-yl)methyl]-2-methyl-6-oxopyrimidin-1(6H)-yl}pyrimidin-5-yl oxy}propyl}acetamide instead of 4'-{[4-butyl-2-methyl-6-oxo-1-(pyridin-2-yl)-1,6-dihydropyrimidin-5-yl]methyl}biphenyl-2-carbonitrile.

¹H-NMR(CDCl₃) δ:

0.92 (3H, t, J=7 Hz), 1.35-1.46 (2H, m), 1.54-1.65 (2H, m), 1.95 (3H, s), 2.01-2.09 (2H, m), 2.06 (3H, s), 2.65 (2H, t, J=8 Hz), 3.34-3.45 (2H, m), 3.97 (2H, s), 4.15 (2H, t, J=6 Hz), 6.05 (1H, brs), 7.35-7.49 (6H, m), 7.58-7.64 (1H, m), 7.74 (1H, dd, J=1, 8 Hz), 8.50 (2H, s).

Example 57

N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}methane sulfonamide

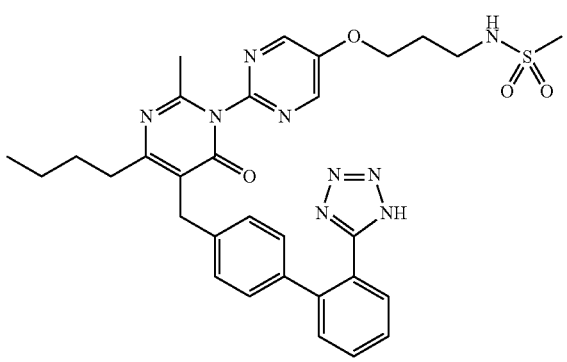 [SMILES: CCCCc1nc(C)n(-c2ncc(OCCCNS(C)(=O)=O)cn2)c(=O)c1Cc1ccc(-c2ccccc2-c2nnn[nH]2)cc1]

Crude product of N-{3-{2-{4-butyl-5-[(2'-cyanobiphenyl-4-yl)methyl]-2-methyl-6-oxopyrimidin-1(6H)-yl}pyrimidin-5-yl oxy}propyl}methane sulfonamide was obtained according to the same reaction and treatment as the Process 3 of Example 56 by using methane sulfonyl chloride instead of acetyl chloride.

The target compound was obtained according to the same reaction and treatment as the Process 3 of Example 1 by using the crude product of N-{3-{2-{4-butyl-5-[(2'-cyanobiphenyl-4-yl)methyl]-2-methyl-6-oxopyrimidin-1(6H)-yl}pyrimidin-5-yl oxy}propyl}methane sulfonamide instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.89 (3H, t, J=7 Hz), 1.30-1.42 (2H, m), 1.52-1.64 (2H, m), 1.85-1.95 (2H, m), 2.07 (3H, s), 2.58 (2H, t, J=8 Hz), 2.78 (3H, s), 3.20 (2H, brs), 3.78 (2H, s), 4.07 (2H, brs), 6.89 (2H, d, J=8 Hz), 6.97 (2H, d, J=8 Hz), 7.30-7.47 (3H, m), 7.75 (1H, d, J=7 Hz), 8.30 (2H, s).

Example 58

Production of N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}-1,1,1-trifluoromethane sulfonamide

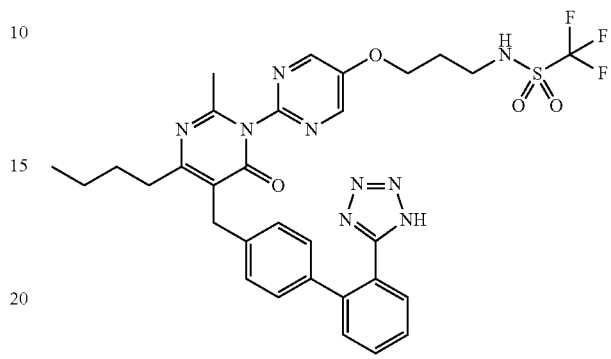

Crude product of N-{3-{2-{4-butyl-5-[(2'-cyanobiphenyl-4-yl)methyl]-2-methyl-6-oxopyrimidin-1(6H)-yl}pyrimidin-5-yl oxy}propyl}-1,1,1-trifluoromethane sulfonamide was obtained according to the same reaction and treatment as the Process 3 of Example 56 by using trifluoromethane sulfonyl chloride instead of acetyl chloride.

The target compound was obtained according to the same reaction and treatment as the Process 3 of Example 1 by using the crude product of N-{3-{2-{4-butyl-5-[(2'-cyanobiphenyl-4-yl)methyl]-2-methyl-6-oxopyrimidin-1(6H)-yl}pyrimidin-5-yl oxy}propyl}-1,1,1-trifluoromethane sulfonamide instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:

0.92 (3H, t, J=7 Hz), 1.33-1.44 (2H, m), 1.62-1.69 (2H, m), 1.89-1.97 (2H, m), 2.06 (3H, s), 2.63 (2H, t, J=8 Hz), 3.42-3.50 (2H, m), 3.83 (2H, s), 4.03-4.11 (2H, m), 6.76-6.87 (4H, m), 7.28-7.48 (3H, m), 7.8 (1H, d, J=7.1 Hz), 8.09 (2H, s).

Example 59

Production of 5-{[2'-(1H-tetrazol-5-yl)biphenyl-4-yl]-6-butyl-3-(2,6-dimethoxypyrimidin-4-yl)-2-methylpyrimidin-4(3H)-one

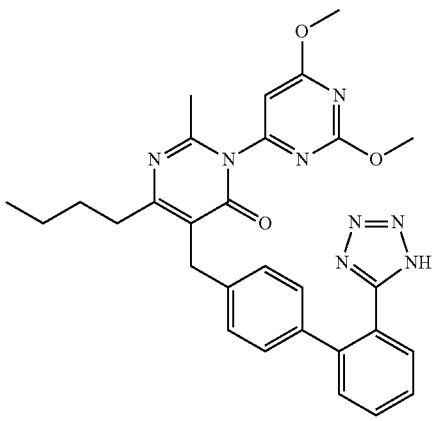 [SMILES: CCCCc1nc(C)n(-c2cc(OC)nc(OC)n2)c(=O)c1Cc1ccc(-c2ccccc2-c2nnn[nH]2)cc1]

4'-{[4-butyl-1-(2,6-dimethoxypyrimidin-4-yl)-2-methyl-6-oxo-1,6-dihydropyrimidin-5-yl]methyl}biphenyl-2-carbonitrile was obtained according to the same reaction and treatment as the Process 2 of Example 1 by using 4-amino-2,6-dimethoxypyrimidine instead of 2-aminopyridine.

¹H-NMR (CDCl₃) δ:
0.93 (3H, t, J=7 Hz), 1.40 (2H, sextet, J=8 Hz), 1.55-1.65 (2H, m), 2.27 (3H, s), 2.61-2.67 (2H, m), 3.96 (2H, s), 4.01 (3H, s), 4.03(3H, s), 7.36-7.49(7H, m), 7.62(1H, m), 7.74(1H, dd, J=7, 1 Hz).

The target compound was obtained according to the same reaction and treatment as the Process 3 of Example 1 by using 4'-{[4-butyl-1-(2,6-dimethoxypyrimidin-4-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.94 (3H, t, J=7 Hz), 1.42 (2H, sextet, J=8 Hz), 1.61-169 (2H, m), 2.27 (3H, s), 2.64-2.68(2H, m), 3.88 (2H, s), 3.99 (3H, s), 4.03(3H, s), 6.42(1H, s), 7.08 (2H, d, J=8 Hz), 7.18 (1H, m), 7.25 (1H, d, J=8 Hz), 7.40 (1H, dd, J=8, 1 Hz), 7.49-7.59(2H, m), 8.12 (1H, d, J=8 Hz).

Example 60

Production of 5-{[2'-(1H-tetrazol-5-yl)biphenyl-4-yl]methyl}-6-butyl-2-methyl-3-(pyrazin-2-yl)pyrimidin-4 (3H)-one

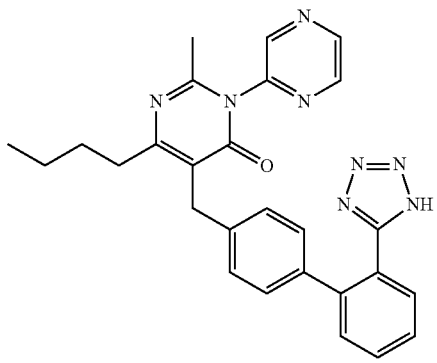 [SMILES: CCCCc1nc(C)n(-c2cnccn2)c(=O)c1Cc1ccc(-c2ccccc2-c2nnn[nH]2)cc1]

4'-{[4-butyl-2-methyl-6-oxo-1-(pyrazin-2-yl)-1,6-dihydropyrimidin-5-yl]methyl}biphenyl-2-carbonitrile was obtained according to the same reaction and treatment as the Process 2 of Example 1 by using 2-aminopyrazine instead of 2-aminopyridine.

¹H-NMR (CDCl₃) δ:
0.94 (3H, t, J=7 Hz), 1.34-1.52 (2H, m), 1.53-1.70 (2H, m), 2.18 (3H, s), 2.68 (2H, t, J=8 Hz), 3.98 (2H, s), 7.33-7.55 (6H, m), 7.62 (1H, t, J=8 Hz), 7.74 (1H, d, J=8 Hz), 8.61-8.78 (3H, m).

The target compound was obtained according to the same reaction and treatment as the Process 3 of Example 1 by using 4'-{[4-butyl-2-methyl-6-oxo-1-(pyrazin-2-yl)-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.93 (3H, t, J=7 Hz), 1.33-1.47 (2H, m), 1.52-1.69 (2H, m), 2.14 (3H, s), 2.64 (2H, t, J=8 Hz), 3.86 (2H, s), 7.01 (2H, d, J=8 Hz), 7.15 (2H, d, J=8 Hz), 7.39 (1H, d, J=8 Hz), 7.46 (1H, t, J=8 Hz), 7.54 (1H, t, J=8 Hz), 7.95 (1H, d, J=7 Hz), 8.54-8.69 (3H, m).

Example 61

Production of 5-{[2'-(1H-tetrazol-5-yl)biphenyl-4-yl]methyl}-6-butyl-3-(5,6-dimethyl-1,2,4-triazin-3-yl)-2-methylpyrimidin-4 (3H)-one

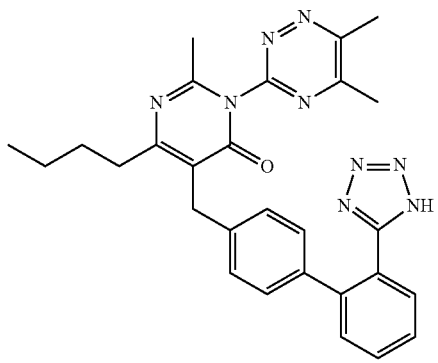 [SMILES: CCCCc1nc(C)n(-c2nnc(C)c(C)n2)c(=O)c1Cc1ccc(-c2ccccc2-c2nnn[nH]2)cc1]

4'-{[4-butyl-1-(5,6-dimethyl-1,2,4-triazin-3-yl)-2-methyl-6-oxo-1,6-dihydropyrimidin-5-yl]methyl}biphenyl-2-carbonitrile was obtained according to the same reaction and treatment as the Process 2 of Example 1 by using 3-amino-5,6-dimethyl-1,2,4-triazine instead of 2-aminopyridine.

¹H-NMR (CDCl₃) δ:
0.93 (3H, t, J=7 Hz), 1.41(2H, sextet, J=8 Hz), 1.57-1.65 (2H, m), 2.19 (3H, s), 2.66 (3H, s), 2.64-2.69 (2H, m), 2.80 (3H, s), 3.98 (2H, s), 7.37-7.48(6H, m), 7.61(1H, td, J=8, 1 Hz), 7.74(1H, dd, J=8, 1 Hz).

The target compound was obtained according to the same reaction and treatment as the Process 3 of Example 1 by using 4'-{[4-butyl-1-(5,6-dimethyl-1,2,4-triazin-3-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.94 (3H, t, J=7 Hz), 1.42(2H, sextet, J=7 Hz), 1.61-1.68 (2H, m), 2.16 (3H, s), 2.64(3H, s), 2.65-2.70(2H, m), 2.78 (3H, s), 3.91 (2H, s), 7.08 (2H, d, J=8 Hz), 7.21 (2H, d, J=8 Hz), 7.39-7.59(3H, m), 8.09 (1H, t, J=6 Hz).

Example 62

Production of 5-{[2'-(1H-tetrazol-5-yl)biphenyl-4-yl]methyl}-6-butyl-2-methyl-3-(thiazol-2-yl)pyrimidin-4 (3H)-one

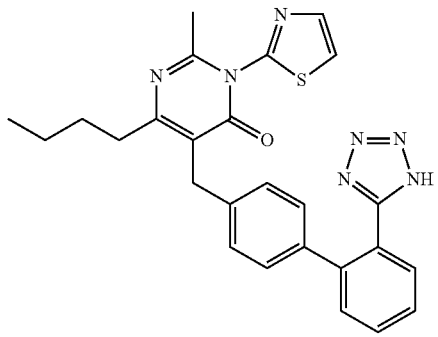 [SMILES: CCCCc1nc(C)n(-c2nccs2)c(=O)c1Cc1ccc(-c2ccccc2-c2nnn[nH]2)cc1]

4'-{[4-butyl-2-methyl-6-oxo-1-(thiazol-2-yl)-1,6-dihydropyrimidin-5-yl]methyl}biphenyl-2-carbonitrile was obtained according to the same reaction and treatment as the Process 2 of Example 1 by using 2-aminothiazole instead of 2-aminopyridine.

$^1$H-NMR (CDCl$_3$) δ:
0.94 (3H, t, J=7 Hz), 1.36-1.46 (2H, m), 1.54-1.64 (2H, m), 2.29 (3H, s), 2.64-2.68 (2H, m), 3.97 (2H, s), 7.38-7.77 (9H, m), 7.84 (1H, d, J=4 Hz).

The target compound was obtained according to the same reaction and treatment as the Process 3 of Example 1 by using 4'-{[4-butyl-2-methyl-6-oxo-1-(thiazol-2-yl)-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.95 (3H, t, J=7 Hz), 1.42 (2H, sextet, J=8 Hz), 1.60-1.68 (2H, m), 2.28 (3H, s), 2.65-2.69 (2H, m), 3.91(2H, s), 7.11 (2H, d, J=8 Hz), 7.30 (2H, d, J=8 Hz), 7.39 (1H, td J=8, 1 Hz), 7.50-7.60 (3H, m), 7.81 (1H, d, J=3 Hz), 8.15 (1H, dd, J=8, 2 Hz).

Example 63

Production of 5-{[2'-(1H-tetrazol-5-yl)biphenyl-4-yl]methyl}-6-butyl-3-(isoxazol-3-yl)-2-methylpyrimidin-4 (3H)-one

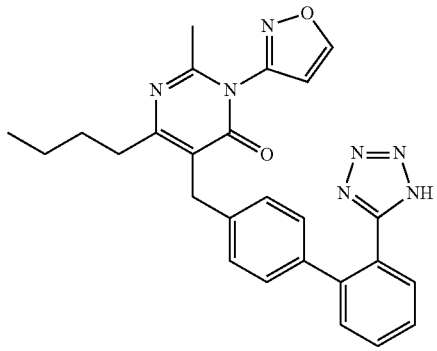 [SMILES: CCCCc1nc(C)n(-c2ccon2)c(=O)c1Cc1ccc(-c2ccccc2-c2nnn[nH]2)cc1]

4'-{[4-butyl-1-(isoxazol-3-yl)-2-methyl-6-oxo-1,6-dihydropyrimidin-5-yl]methyl}biphenyl-2-carbonitrile was obtained according to the same reaction and treatment as the Process 2 of Example 1 by using 3-aminoisoxazole instead of 2-aminopyridine.

$^1$H-NMR (CDCl$_3$) δ:
0.94 (3H, t, J=7 Hz), 1.41 (2H, sextet, J=8 Hz), 1.58-1.65 (2H, m), 2.31 (3H, s), 2.64-2.66 (2H, m), 3.96 (2H, s), 6.59 (1H, d, J=2 Hz), 7.37-7.50 (6H, m), 7.62 (1H, m), 7.74 (1H, d, J=8 Hz), 8.60 (1H, d, J=2 Hz).

The target compound was obtained according to the same reaction and treatment as the Process 3 of Example 1 by using 4'-{[4-butyl-1-(isoxazol-3-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR(CDCl$_3$) δ:
0.95 (3H, t, J=7 Hz), 1.43 (2H, sextet, J=8 Hz), 1.60-1.70 (2H, m), 2.31 (3H, s), 2.66-2.70 (2H, m), 3.92 (2H, s), 6.58 (1H, d, J=2 Hz), 7.12 (2H, d, J=8 Hz), 7.17-7.60 (5H, m), 8.16 (1H, m), 8.59 (1H, d, J=2 Hz).

Example 64

Production of 5-{[2'-(1H-tetrazol-5-yl)biphenyl-4-yl]methyl}-6-butyl-2-methyl-3-(1-methyl-1H-pyrazol-5-yl)pyrimidin-4 (3H)-one

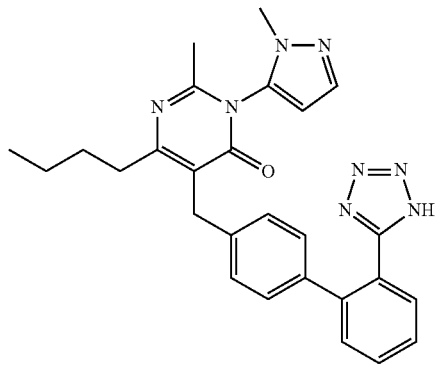 [SMILES: CCCCc1nc(C)n(-c2ccnn2C)c(=O)c1Cc1ccc(-c2ccccc2-c2nnn[nH]2)cc1]

4'-{[4-butyl-2-methyl-1-(1-methyl-1H-pyrazol-5-yl)-6-oxo-1,6-dihydropyrimidin-5-yl]methyl}biphenyl-2-carbonitrile was obtained according to the same reaction and treatment as the Process 2 of Example 1 by using 1-methyl-1H-pyrazol-5-amine instead of 2-aminopyridine.

$^1$H-NMR (CDCl$_3$) δ:
0.95 (3H, t, J=7 Hz), 1.42 (2H, sextet, J=8 Hz), 1.58-1.65 (2H, m), 2.20 (3H, s), 2.65-2.69 (2H, m), 3.67(3H, s), 3.94 (1H, d, J=15 Hz), 3.99 (2H, d, J=15 Hz), 6.29(1H, d, J=2 Hz), 7.37-7.51 (6H, m), 7.60-7.67 (2H, m), 7.75 (1H, d, J=8 Hz).

The target compound was obtained according to the same reaction and treatment as the Process 3 of Example 1 by using 4'-{[4-butyl-2-methyl-1-(1-methyl-1H-pyrazol-5-yl)-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.95 (3H, t, J=7 Hz), 1.43 (2H, sextet, J=8 Hz), 1.60-1.70 (2H, m), 2.20 (3H, s), 2.68 (2H, t, J=8 Hz), 3.61(3H, s), 3.88 (1H, d, J=15 Hz), 3.93 (2H, d, J=15 Hz), 6.26(1H, d, J=2 Hz), 7.09 (2H, d, J=8 Hz), 7.24 (2H, d, J=8 Hz), 7.41 (1H, d, J=7 Hz), 7.50-7.60 (3H, m), 8.08 (1H, d, J=7 Hz).

Example 65

Production of 5-{[2'-(1H-tetrazol-5-yl)biphenyl-4-yl]methyl}-6-butyl-2-methyl-3-(1-methyl-1H-1,2,4-triazol-3-yl)pyrimidin-4 (3H)-one

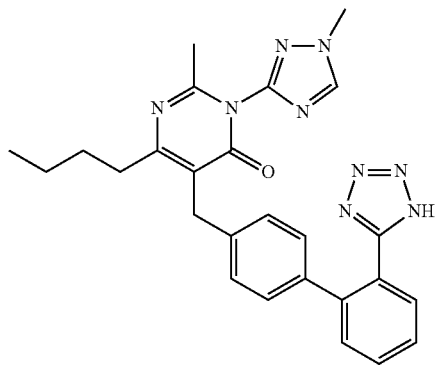 [SMILES: CCCCc1nc(C)n(-c2ncn(C)n2)c(=O)c1Cc1ccc(-c2ccccc2-c2nnn[nH]2)cc1]

4'-{[4-butyl-2-methyl-1-(1-methyl-1,2,4-triazol-3-yl)-6-oxo-1,6-dihydropyrimidin-5-yl]methyl}biphenyl-2-carbonitrile was obtained according to the same reaction and treatment as the Process 2 of Example 1 by using 1-methyl-1H-1,2,4-triazol-3-amine instead of 2-aminopyridine.

¹H-NMR (CDCl₃) δ:
0.92 (3H, t, J=7 Hz), 1.38 (2H, sextet, J=8 Hz), 1.55-1.62 (2H, m), 2.21 (3H, s), 2.62-2.66 (2H, m), 3.96 (2H, s), 4.01 (3H, s), 7.38-7.51(6H, m), 7.62 (1H, t, J=7 Hz), 7.74 (1H, d, J=7 Hz), 8.17 (1H, s).

The target compound was obtained according to the same reaction and treatment as the Process 3 of Example 1 by using 4'-{[4-butyl-2-methyl-1-(1-methyl-1,2,4-triazol-3-yl)-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR(CDCl₃) δ:
0.95 (3H, t, J=7 Hz), 1.42 (2H, sextet, J=8 Hz), 1.60-1.70 (2H, m), 2.21 (3H, s), 2.66-2.70 (2H, m), 3.89 (2H, s), 3.99 (3H, s), 7.10(2H, d, J=8 Hz), 7.27 (2H, d, J=8 Hz), 7.40 (1H, dd, J=8, 2 Hz), 7.48-7.60 (2H, m), 8.10-8.14(2H, m).

Example 66

Production of 5-{[2'-(1H-tetrazol-5-yl)biphenyl-4-yl]methyl}-6-butyl-2-methyl-3-(quinolin-2-yl)pyrimidin-4 (3H)-one

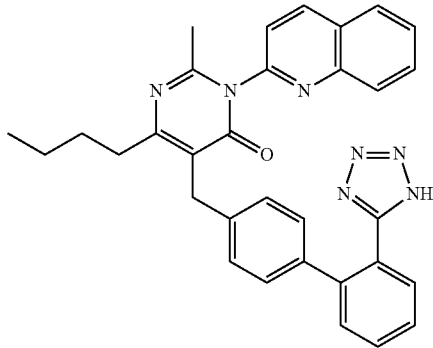 [SMILES: CCCCc1nc(C)n(-c2ccc3ccccc3n2)c(=O)c1Cc1ccc(-c2ccccc2-c2nnn[nH]2)cc1]

4'-{[4-butyl-2-methyl-6-oxo-1-(quinolin-2-yl)-1,6-dihydropyrimidin-5-yl]methyl}biphenyl-2-carbonitrile was obtained according to the same reaction and treatment as the Process 2 of Example 1 by using 2-aminoquinoline instead of 2-aminopyridine.

¹H-NMR (CDCl₃) δ:
0.95 (3H, t, J=7 Hz), 1.36-1.49 (2H, m), 1.57-1.70 (2H, m), 2.22 (3H, s), 2.70 (2H, t, J=8 Hz), 4.00 (2H, s), 7.34-7.50 (7H, m), 7.54-7.69 (2H, m), 7.70-7.83 (2H, m), 7.93 (1H, d, J=8 Hz), 8.10 (1H, d, J=9 Hz), 8.37 (1H, d, J=9 Hz).

The target compound was obtained according to the same reaction and treatment as the Process 3 of Example 1 by using 4'-{[4-butyl-2-methyl-6-oxo-1-(quinolin-2-yl)-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.93 (3H, t, J=7 Hz), 1.34-1.47 (2H, m), 1.52-1.72 (2H, m), 2.16 (3H, s), 2.52-2.72 (2H, m), 3.84 (2H, s), 6.85-7.03 (2H, m), 7.05-7.20 (2H, m), 7.27-7.43 (3H, m), 7.50 (1H, t, J=7 Hz), 7.65 (1H, t, J=7 Hz), 7.78 (2H, t, J=7 Hz), 7.90 (1H, d, J=8 Hz), 8.02 (1H, d, J=8 Hz), 8.30 (1H, d, 8 Hz).

Example 67

Production of 5-{[2'-(1H-tetrazol-5-yl)biphenyl-4-yl]methyl}-6-butyl-3-(isoquinolin-1-yl)-2-methylpyrimidin-4 (3H)-one

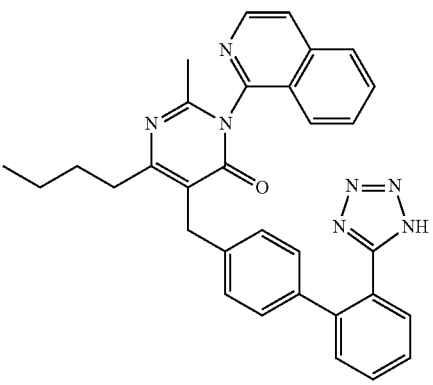 [SMILES: CCCCc1nc(C)n(-c2nccc3ccccc23)c(=O)c1Cc1ccc(-c2ccccc2-c2nnn[nH]2)cc1]

4'-{[4-butyl-1-(isoquinolin-1-yl)-2-methyl-6-oxo-1,6-dihydropyrimidin-5-yl]methyl}biphenyl-2-carbonitrile was obtained according to the same reaction and treatment as the Process 2 of Example 1 by using 1-aminoisoquinoline instead of 2-aminopyridine.

¹H-NMR (CDCl₃) δ:
0.97 (3H, t, J=7 Hz), 1.35-1.49 (2H, m), 1.56-1.77 (2H, m), 2.07 (3H, s), 2.64-2.81 (2H, m), 4.00 (1H, d, J=15 Hz), 4.04 (1H, d, J=15 Hz), 7.35-7.54 (6H, m), 7.54-7.69 (2H, m), 7.70-7.78 (2H, m), 7.82 (1H, d, J=6 Hz), 7.95 (1H, d, J=8 Hz), 8.56 (1H, d, J=6 Hz).

The target compound was obtained according to the same reaction and treatment as the Process 3 of Example 1 by using 4'-{[4-butyl-1-(isoquinolin-1-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

¹H-NMR (CDCl₃) δ:
0.95 (3H, t, J=7 Hz), 1.33-1.52 (2H, m), 1.55-1.77 (2H, m), 2.01 (3H, s), 2.55-2.77 (2H, m), 3.84 (1H, d, J=15 Hz), 3.92 (1H, d, J=15 Hz), 6.96 (2H, d, J=8 Hz), 7.15 (2H, d, J=8 Hz), 7.28-7.57 (4H, m), 7.60-7.78 (3H, m), 7.80-7.97 (2H, m), 8.42 (1H, d, J=6 Hz).

Example 68

Production of 5-{[2'-(1H-tetrazol-5-yl)biphenyl-4-yl]methyl}-6-butyl-3-(isoquinolin-3-yl)-2-methylpyrimidin-4 (3H)-one

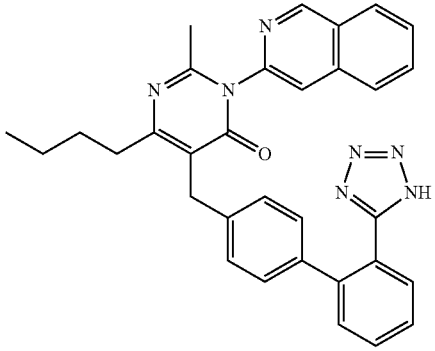 [SMILES: CCCCc1nc(C)n(-c2cc3ccccc3cn2)c(=O)c1Cc1ccc(-c2ccccc2-c2nnn[nH]2)cc1]

4'-{[4-butyl-1-(isoquinolin-3-yl)-2-methyl-6-oxo-1,6-dihydropyrimidin-5-yl]methyl}biphenyl-2-carbonitrile was obtained according to the same reaction and treatment as the Process 2 of Example 1 by using 3-aminoisoquinoline instead of 2-aminopyridine.

$^1$H-NMR (CDCl$_3$) δ:
0.95 (3H, t, J=7 Hz), 1.43 (2H, sextet, J=8 Hz), 1.60-1.68 (2H, m), 2.21 (3H, s), 2.68-2.71 (2H, m), 4.00 (2H, s), 7.39-7.52 (6H, m), 7.60-7.81 (5H, m), 7.91 (1H, d, J=8 Hz), 8.08 (1H, d, J=8 Hz), 9.31 (1H, s).

The target compound was obtained according to the same reaction and treatment as the Process 3 of Example 1 by using 4'-{[4-butyl-1-(isoquinolin-3-yl)-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.96 (3H, t, J=7 Hz), 1.45 (2H, sextet, J=8 Hz), 1.64-1.72 (2H, m), 2.18 (3H, s), 2.69-2.73 (2H, m), 3.93 (2H, s), 7.08 (2H, d, J=8 Hz), 7.30 (2H, d, J=8 Hz), 7.40-7.58 (3H, m), 7.70-7.80 (3H, m), 7.92 (1H, d, J=8 Hz), 8.01-8.07(2H, m), 9.23 (1H, s).

Example 69

Production of 5-{[2'-(1H-tetrazol-5-yl)biphenyl-4-yl]methyl}-6-butyl-2-methyl-3-(1-methyl-1H-benzimidazol-2-yl)pyrimidin-4 (3H)-one

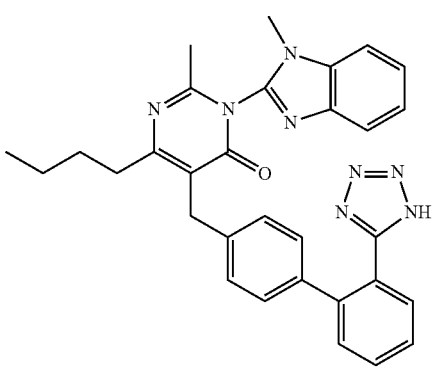 [SMILES: CCCCc1nc(C)n(-c2nc3ccccc3n2C)c(=O)c1Cc1ccc(-c2ccccc2-c2nnn[nH]2)cc1]

4'-{[4-butyl-2-methyl-1-(1-methyl-benzimidazol-2-yl)-6-oxo-1,6-dihydropyrimidin-5-yl]methyl}biphenyl-2-carbonitrile was obtained according to the same reaction and treatment as the Process 2 of Example 1 by using 2-amino-1-methylbenzimidazole instead of 2-aminopyridine.

$^1$H-NMR (CDCl$_3$) δ:
0.91 (3H, t, J=7 Hz), 1.41 (2H, sextet, J=8 Hz), 1.50-1.70 (2H, m), 2.21 (3H, s), 2.65-2.73 (2H, m), 3.51 (3H, s), 4.03 (2H, s), 7.18-7.29 (4H, m), 7.30-7.50 (6H, m), 7.64 (1H, m), 7.74 (1H, m).

The target compound was obtained according to the same reaction and treatment as the Process 3 of Example 1 by using 4'-{[4-butyl-2-methyl-1-(1-methyl-benzimidazol-2-yl)-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:
0.96 (3H, t, J=7 Hz), 1.43 (2H, sextet, J=8 Hz), 1.62-1.72 (2H, m), 2.23 (3H, s), 2.67-2.72 (2H, m), 3.62 (3H, s), 3.85 (1H, d, J=15 Hz), 3.95(1H, d, J=15 Hz), 7.02 (2H, d, J=8 Hz), 7.22 (2H, d, J=8 Hz), 7.25-7.60 (6H, m), 7.74 (1H, d, J=8 Hz), 8.03 (1H, d, J=8 Hz).

Example 70

Production of 5-{[2'-(1H-tetrazol-5-yl)biphenyl-4-yl]methyl}-3-(benzothiazol-2-yl)-6-butyl-2-methylpyrimidin-4 (3H)-one

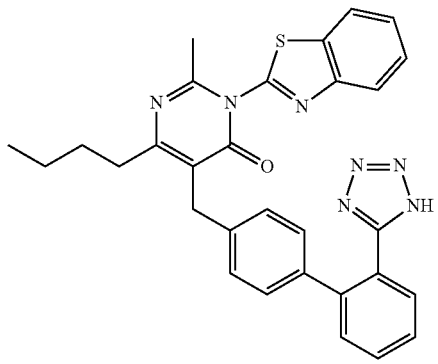 [SMILES: CCCCc1nc(C)n(-c2nc3ccccc3s2)c(=O)c1Cc1ccc(-c2ccccc2-c2nnn[nH]2)cc1]

4'-{[1-(Benzothiazol-2-yl)-4-butyl-2-methyl-6-oxo-1,6-dihydropyrimidin-5-yl]methyl}biphenyl-2-carbonitrile was obtained according to the same reaction and treatment as the Process 2 of Example 1 by using 2-aminobenzothiazole instead of 2-aminopyridine.

$^1$H-NMR (CDCl$_3$) δ:
0.95 (3H, t, J=7 Hz), 1.33-1.46 (2H, m), 1.55-1.67 (2H, m), 2.37 (3H, s), 2.68 (2H, t, J=8 Hz), 3.99 (2H, s), 7.33-7.65 (9H, m), 7.74 (1H, d, J=8 Hz), 7.93 (1H, d, J=8 Hz), 8.08 (1H, d, J=8 Hz).

The target compound was obtained according to the same reaction and treatment as the Process 3 of Example 1 by using 4'-{[1-(benzothiazol-2-yl)-4-butyl-2-methyl-6-oxo-1,6-dihydropyrimidin-5-yl]methyl}biphenyl-2-carbonitrile instead of 4'-{[4-butyl-2-methyl-6-oxo-1-(pyridin-2-yl)-1,6-dihydropyrimidin-5-yl]methyl}biphenyl-2-carbonitrile.

$^1$H-NMR (CDCl$_3$) δ:

0.94 (3H, t, J=7 Hz), 1.31-1.49 (2H, m), 1.53-1.65 (2H, m), 2.34 (3H, s), 2.65 (2H, t, J=8 Hz), 3.86 (2H, s), 7.02 (2H, d, J=8 Hz), 7.17 (2H, d, J=8 Hz), 7.32-7.62 (5H, m), 7.80-8.12 (3H, m).

Test example 1

Angiotensin II Antagonistic Activity in Isolated Rabbit Blood Vessels

By using a specimen of isolated rabbit blood vessels, antagonistic activity of the compounds of the invention against angiotensin II type 1 receptor was estimated from a dose-response curve of angiotensin II-induced blood vessel contraction.

Specifically, the specimen of thoracic aorta ring of a rabbit (New Zealand White: male, 2.4 to 3.0 kg) was suspended in a magnus bath filled with Krebs-Henseleite buffer (composition: 118 mM NaCl, 4.7 mM KCl, 2.55 mM CaCl$_2$, 1.18 mM MgSO$_4$, 1.18 mM KH$_2$PO$_4$, 24.88 mM NaHCO$_3$, and 11.1 mM D-glucose), and angiotensin II (10 nM)-induced contraction was obtained in the presence of the compounds of each example (1 nmol to 10 μmol/L). During the measurement, the inside temperature of the magnus bath was maintained at 37° C. and the bath was continuously ventilated with a sufficient amount of mixed gas (95% O$_2$ and 5% CO$_2$). The angiotensin II-induced contraction was converted into a relative value (%) that is based on the angiotensin II (10 nM)-induced contraction in the absence of the compounds of each example. From the concentration-response curve obtained therefrom, 50% inhibition concentration (IC$_{50}$ value) was calculated by using SAS Preclinical Package Ver5.0 (trade name, manufactured by SAS institute Japan Co., Tokyo, Japan), which is a statistical analysis program.

As a result, it was found that the compound described in each example has an angiotensin II inhibition activity at 10 μM concentration. Some compounds are described with their activity value in Table 1. As shown in Table 1, it was confirmed that the compounds of the invention have a potent angiotensin II antagonistic activity. In particular, the compounds of Example 1, 17, 18, 20, 27, 29, 38 to 43, 46 to 48, 51 to 53, 56, 57, and 60 have IC$_{50}$ value of less than 0.01 μM, indicating stronger angiotensin II antagonistic activity than telmisartan. Under the same condition, the angiotensin II antagonistic activity of telmisartan i.e., IC$_{50}$, was 0.025 μM.

TABLE 1

| Example No. | IC$_{50}$ (μM) |
| --- | --- |
| 1 | 0.0021 |
| 2 | 0.084 |
| 3 | 0.018 |
| 4 | 0.060 |
| 5 | 0.102 |
| 6 | 0.024 |
| 7 | 0.431 |
| 8 | 0.395 |
| 9 | 0.014 |
| 10 | 0.181 |
| 11 | 0.981 |
| 12 | 0.230 |

TABLE 1-continued

| Example No. | IC$_{50}$ (μM) |
| --- | --- |
| 13 | 0.026 |
| 14 | 0.546 |
| 16 | 0.014 |
| 17 | 0.0092 |
| 18 | 0.0027 |
| 19 | 0.396 |
| 20 | 0.0063 |
| 21 | 0.017 |
| 22 | 0.155 |
| 23 | 0.022 |
| 24 | 0.141 |
| 25 | 0.024 |
| 26 | 0.024 |
| 27 | 0.0050 |
| 28 | 0.049 |
| 29 | 0.0077 |
| 30 | 0.020 |
| 31 | 0.338 |
| 32 | 0.428 |
| 33 | 0.956 |
| 34 | 0.754 |
| 35 | 0.347 |
| 36 | 0.627 |
| 37 | 0.0252 |
| 38 | 0.0065 |
| 39 | 0.0010 |
| 40 | 0.0059 |
| 41 | 0.0087 |
| 42 | 0.0027 |
| 43 | 0.0055 |
| 44 | 0.963 |
| 45 | 0.242 |
| 46 | 0.0043 |
| 47 | 0.0026 |
| 48 | 0.0099 |
| 49 | 0.012 |
| 50 | 0.014 |
| 51 | 0.0058 |
| 52 | 0.0083 |
| 53 | 0.0085 |
| 54 | 0.025 |
| 55 | <0.1 |
| 56 | 0.0024 |
| 57 | 0.0036 |
| 58 | 0.352 |
| 59 | 0.013 |
| 60 | 0.0081 |
| 61 | 0.025 |
| 62 | 0.435 |
| 63 | 0.193 |
| 64 | 0.652 |
| 65 | 0.023 |
| 66 | 0.432 |
| 67 | <10 |
| 68 | 0.223 |
| 69 | 0.958 |

Test example 2

PPARγ Activation Activity

The agonistic activity of the compounds of the invention on PPARγ was measured based on the transfection assay using COS7 cells (DS Pharma Biomedical Co., Ltd., Osaka, Japan), which are the cell line derived from the kidney of the African green monkey. COS7 cells were cultured under 5% CO$_2$ concentration, and DMEM medium containing 10% fetal bovine serum, glutamic acid, and antibiotics was used as a medium.

As an expression vector, a chimera in which DNA binding domain of Gal4, which is a yeast transcription factor, and ligand binding domain of human PPAR$^{γ2}$ are fused, i.e., a fused product between the amino acids 1 to 147 of Gal4 transcription factor and the amino acids 182 to 505 of human PPARγ2, was used. Furthermore, as a reporter vector, a firefly luciferase containing five copies of Gal4 recognition sequence in the promoter region was used. Plasmid transfection to the cells was performed according to a method which uses jetPEI (trade name, manufactured by Funakoshi Co., Ltd., Tokyo, Japan). Furthermore, β-galactosidase expression vector was employed as an internal standard.

After the transfection of the cells, the medium was replaced with a DMEM medium (containing 1% serum) added with the compound, and the cells were further cultured for 16 hours. After that, the luciferase activity and β-galactosidase activity in the cell lysis solution were measured.

For the present test, dimethyl sulfoxide (DMSO) was used for dissolution and dilution of the test compounds, and during the cell treatment, the DMSO concentration in DMEM medium (containing 1% serum) was adjusted to 0.1%. As a positive compound, rosiglitazone (trade name, manufactured by ALEXIS Corporation, Switzerland) was used. The luciferase activity (%) of the test compounds (1 to 30 μmol/L) was calculated when the luciferase activity of rosiglitazone (3 to 10 μmol/L) is 100% and the luciferase activity in the absence of the test compound is 0%. The 50% effective concentration of the test compound ($EC_{50}$, 50% effect concentration) was calculated by using SAS Preclinical Package Ver5.0 (trade name, manufactured by SAS institute Japan Co., Tokyo, Japan), which is a statistical analysis program.

As a result, it was found that the each compound described in Example has a PPARγ activation activity at 30 μM concentration. Results obtained from some compounds are described in Table 2. As shown in Table 2, it was confirmed that the compounds of the invention have a potent PPARγ activation activity. In particular, the compounds of Example 4, 6 to 8, 11, 13, 16, 19, 21 to 24, 28, 47, 49, 52, 58, 59, and 66 to 70 have $EC_{50}$ value of less than 3 μM, indicating the PPARγ activation activity that is equivalent to telmisartan. Example 8, 13, 22 to 24, 47, 49, 52, 66, 67, and 70 have $EC_{50}$ value of less than 1 μM, indicating stronger PPARγ activation activity than telmisartan. Maximum activity strength of some compounds relative to the maximum activity of rosiglitazone is given in Table 3. As shown in Table 3, it was confirmed that the compounds of the invention have an activity that is 20 to 56% of the maximum activity of rosiglitazone and they have an agonist activity on PPARγ. In particular, the maximum activity of the compounds of Example 7, 11, 66 and 70 was the same or greater than that of telmisartan. Under the same condition, the PPARγ activation activity of telmisartan, i.e., $EC_{50}$, was 1 to 5 μM, and the maximum activity strength relative to the maximum activity of rosiglitazone (i.e., % MAX vs rosiglitazone) was 30 to 50%.

TABLE 2

| Example No. | $EC_{50}$ (μM) |
| --- | --- |
| 2 | 4.15 |
| 3 | 3.74 |
| 4 | 1.44 |
| 5 | 3.66 |
| 6 | 1.69 |
| 7 | 1.52 |
| 8 | 0.88 |
| 10 | 3.89 |
| 11 | 1.30 |
| 13 | 0.17 |
| 16 | 2.41 |
| 19 | 2.55 |
| 21 | 1.59 |
| 22 | 0.59 |

TABLE 2-continued

| Example No. | $EC_{50}$ (μM) |
| --- | --- |
| 23 | 0.89 |
| 24 | 0.86 |
| 26 | 3.89 |
| 28 | 1.23 |
| 36 | 3.77 |
| 42 | 4.22 |
| 47 | 0.08 |
| 49 | 0.07 |
| 52 | 0.14 |
| 58 | 1.91 |
| 59 | 1.24 |
| 62 | 3.39 |
| 63 | 3.67 |
| 64 | 3.30 |
| 66 | 0.82 |
| 67 | 0.74 |
| 68 | 2.61 |
| 69 | 2.69 |
| 70 | 0.69 |

TABLE 3

| Example. No. | % MAX vs Rosiglitazone |
| --- | --- |
| 2 | 24.1 |
| 5 | 27.6 |
| 6 | 20.3 |
| 7 | 54.6 |
| 8 | 27.7 |
| 11 | 48.6 |
| 22 | 22.8 |
| 16 | 35.5 |
| 22 | 22.8 |
| 28 | 28.9 |
| 66 | 55.5 |
| 69 | 31.6 |
| 70 | 39.7 |

From the results obtained above, it was confirmed that the compounds represented by the formula (I) have both a potent angiotensin II receptor antagonistic activity and a PPARγ activation activity. Thus, it was found that the compounds represented by the formula (I) and pharmaceutically acceptable salts thereof are useful as an effective component of a prophylactic and/or therapeutic agent for disorders involved with angiotensin II and PPARγ, for example, hypertension, heart diseases, angina pectoris, cerebrovascular disorders, cerebral circulatory disorders, ischemic peripheral circulatory disorders, renal diseases, arteriosclerosis, inflammatory diseases, type 2 diabetes, diabetic complications, insulin resistance syndrome, syndrome X, metabolic syndrome, and hyperinsulinemia.

Industrial Applicability

The invention provides a novel compound of 3-heteroarylpyrimidin-4 (3H)-one derivative represented by the formula (I) of the invention, or salt or solvate thereof, which has both an angiotensin II receptor antagonistic activity and a PPARγ activation activity. They can be used as an effective component of a novel pharmaceutical product, i.e., a prophylactic and/or therapeutic agent for disorders involved with angiotensin II and PPARγ, for example, hypertension, heart diseases, angina pectoris, cerebrovascular disorders, cerebral circulatory disorders, ischemic peripheral circulatory disorders, renal diseases, arteriosclerosis, inflammatory diseases, type 2 diabetes, diabetic complications, insulin resistance syndrome, syndrome X, metabolic syndrome, and hyperinsulinemia, and therefore have an industrial applicability.

The invention claimed is:
1. A 3-heteroarylpyrimidin-4(3H)-one derivative represented by the formula (I) below or salt thereof, or solvate thereof:

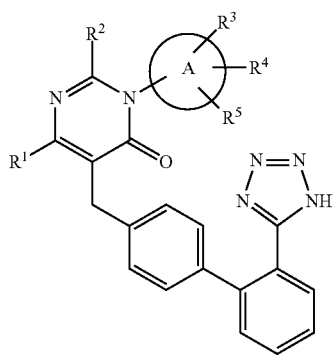

(I)

wherein A is a pyridyl group, a pyrimidinyl group, a pyrazinyl group, a triazinyl group, a thiazolyl group, an isoxazolyl group, a pyrazolyl group, a triazolyl group, a quinolynyl group, an isoquinolynyl group, a benzimidazolyl group, or a benzothiazolyl group,
wherein $R^1$ and $R^2$, which may be the same or different from each other, represent a $C_{1-6}$ alkyl group, and
wherein each of $R^3$, $R^4$, and $R^5$ is independently absent or represents a hydrogen atom, a halogen atom, a $C_{1-6}$ alkyl group, a halo $C_{1-6}$ alkyl group, a $C_{1-6}$ alkoxy group which may have a substituent group, a $C_{3-6}$ cycloalkyloxy group which may have a substituent group, a 5- to 10- membered heteroaryl group, a hydroxyl group, or a nitro group.

2. The 3-heteroarylpyrimidin-4(3H)-one derivative according to claim 1, or salt thereof, or solvate thereof, wherein a substituent group of the $C_{1-6}$ alkoxy group is selected from the group consisting of (i) a phenyl group; (ii) a hydroxyl group; (iii) a $C_{1-6}$ alkylthio group; (iv) a $C_{1-6}$ alkylsulfonyl group; (v) an oxazolyl group which may be substituted with a 5- to 10-membered heteroaryl group which may be substituted with a $C_{1-6}$ alkyl group, a $C_{6-10}$ aryl group, or a halogen atom; (vi) a pyridyl group which may be substituted with a $C_{1-6}$ alkyl group; (vii) a $C_{1-6}$ alkoxycarbonyl group; (viii) a carboxyl group; (ix) a carbamoyl group which may be substituted with a $C_{1-6}$ alkyl group; (x) a $C_{1-6}$ alkanoylamino group; (xi) a $C_{1-6}$ alkylsulfonylamino group; and (xii) halo $C_{1-6}$ alkylsulfonylamino group.

3. The 3-heteroarylpyrimidin-4(3H)-one derivative described in claim 1 or salt thereof, or solvate thereof, wherein a substituent group of the $C_{3-6}$ cycloalkyloxy group is an oxo group.

4. The 3-heteroarylpyrimidin-4(3H)-one derivative described in claim 1 or salt thereof, or solvate thereof, in which the compound represented by the formula (I) is a compound that is selected from a group consisting of:

5-{[2'-(1H-tetrazol-5-yl)biphenyl-4-yl]methyl}-6-butyl-2-methyl-3-(pyridin-2-yl)pyrimidin-4(3H)-one,
5-{[2'-(1H-tetrazol-5-yl)biphenyl-4-yl]methyl}-6-butyl-2-methyl-3-(5-methylpyridin-2-yl)pyrimidin-4(3H)-one,
5-{[2'-(1H-tetrazol-5-yl)biphenyl-4-yl]methyl}-6-butyl-3-(5-methoxypyridin-2-yl)-2-methylpyrimidin-4(3H)-one,
5-{[2'-(1H-tetrazol-5-yl)biphenyl-4-yl]methyl}-6-butyl-3-(3-fluoropyridin-2-yl)-2-methylpyrimidin-4(3H)-one,
5-{[2'-(1H-tetrazol-5-yl)biphenyl-4-yl]methyl}-6-butyl-3-(5-fluoropyridin-2-yl)-2-methylpyrimidin-4(3H)-one,
5-{[2'-(1H-tetrazol-5-yl)biphenyl-4-yl]methyl}-6-butyl-3-(3-chloropyridin-2-yl)-2-methylpyrimidin-4(3H)-one,
5-{[2'-(1H-tetrazol-5-yl)biphenyl-4-yl]methyl}-6-butyl-3-(5-chloropyridin-2-yl)-2-methylpyrimidin-4(3H)-one,
5-{[2'-(1H-tetrazol-5-yl)biphenyl-4-yl]methyl}-3-(6-bromopyridin-2-yl)-6-butyl-2-methylpyrimidin-4(3H)-one,
5-{[2'-(1H-tetrazol-5-yl)biphenyl-4-yl]methyl}-6-butyl-2-methyl-3-[3-(trifluoromethyl)pyridin-2-yl]pyrimidin-4(3H)-one,
5-{[2'-(1H-tetrazol-5-yl)biphenyl-4-yl]methyl}-6-butyl-2-methyl-3-[4-(trifluoromethyl)pyridin-2-yl]pyrimidin-4(3H)-one,
5-{[2'-(1H-tetrazol-5-yl)biphenyl-4-yl]methyl}-6-butyl-2-methyl-3-[5-(trifluoromethyl) pyridin-2-yl)pyrimidin-4(3H)-one,
5-{[2'-(1H-tetrazol-5-yl)biphenyl-4-yl]methyl}-6-butyl-2-methyl-3-[6-(trifluoromethyl)pyridin-2-yl]pyrimidin-4(3H)-one,
5-{[2'-(1H-tetrazol-5-yl)biphenyl-4-yl]methyl}-6-butyl-3-[3-chloro-5-(trifluoromethyl)pyridin-2-yl]-2-methylpyrimidin-4(3H)-one,
5-{[2'-(1H-tetrazol-5-yl)biphenyl-4-yl]methyl}-6-butyl-2-methyl-3-(5-nitropyridin-2-yl)pyrimidin-4(3H)-one,
5-{[2'-(1H-tetrazol-5-yl)biphenyl-4-yl]methyl}-3-[5-(1H-tetrazol-5-yl)pyridin-2-yl]-6-butyl-2-methylpyrimidin-4(3H)-one,
5-{[2'-(1H-tetrazol-5-yl)biphenyl-4-yl]methyl}-3-(5-bromopyrimidin-2-yl)-6-butyl-2-methylpyrimidin-4(3H)-one,
5-{[2'-(1H-tetrazol-5-yl)biphenyl-4-yl]methyl}-6-butyl-2-methyl-3-(pyrimidin-2-yl)pyrimidin-4(3H)-one,
5-{[2'-(1H-tetrazol-5-yl)biphenyl-4-yl]methyl}-6-butyl-3-(5-methoxypyrimidin-2-yl)-2-methylpyrimidin-4(3H)-one,
5-{[2'-(1H-tetrazol-5-yl)biphenyl-4-yl]methyl}-3-[5-(benzyloxy)pyrimidin-2-yl]-6-butyl-2-methylpyrimidin-4(3H)-one,
5-{[2'-(1H-tetrazol-5-yl)biphenyl-4-yl]methyl}-6-butyl-3-(5-hydroxypyrimidin-2-yl)-2-methylpyrimidin-4(3H)-one,
5-{[2'-(1H-tetrazol-5-yl)biphenyl-4-yl]methyl}-6-butyl-3-(5-ethoxypyrimidin-2-yl)-2-methylpyrimidin-4(3H)-one,
5-{[2'-(1H-tetrazol-5-yl)biphenyl-4-yl]methyl}-6-butyl-2-methyl-3-(5-propoxypyrimidin-2-yl)pyrimidin-4(3H)-one,
5-{[2'-(1H-tetrazol-5-yl)biphenyl-4-yl]methyl}-6-butyl-3-(5-isopropoxypyrimidin-2-yl)-2-methylpyrimidin-4(3H)-one,
5-{[2'-(1H-tetrazol-5-yl)biphenyl-4-yl]methyl}-3-(5-butoxypyrimidin-2-yl)-6-butyl-2-methylpyrimidin-4(3H)-one,
5-{[2'-(1H-tetrazol-5-yl)biphenyl-4-yl]methyl}-6-butyl-3-[5-(3-hydroxypropoxy)pyrimidin-2-yl]-2-methylpyrimidin-4(3H)-one,
5-{[2'-(1H-tetrazol-5-yl)biphenyl-4-yl]methyl}-6-butyl-2-methyl-3-{5-[2-(methylthio)ethoxy]pyrimidin-2-yl}pyrimidin-4(3H)-one, 5-{[2'-(1H-tetrazol-5-yl)biphenyl-4-yl]methyl}-6-butyl-2-methyl-3-{5-[2-(methylsulfonyl)ethoxy]pyrimidin-2-yl}pyrimidin-4(3H)-one, 5-{[2'-(1H-tetrazol-5-yl)biphenyl-4-yl]methyl}-6-butyl-3-[5-(cyclohexyloxy)pyrimidin-2-yl]-2-methylpyrimidin-4(3H)-one, 5-{[2'-(1H-tetrazol-5-yl)biphenyl-4-yl]methyl}-6-butyl-2-methyl-3-[5-(4-oxocyclohexyloxy)pyrimidin-2-yl]pyrimidin-4(3H)-one, 5-{[2'-(1H-tetrazol-5-yl)biphenyl-4-yl]methyl}-6-butyl-3-(4,6-dichloropyrimidin-2-yl)-2-methylpyrimidin-4(3H)-one, 5-{[2'-(1H-tetrazol-5-yl)biphenyl-4-yl]methyl}-6-butyl-2-methyl-3-{5-{5-methyl-2-phenyloxazol-4-methoxy]pyrimidin-2-yl}pyrimidin-4(3H)-one, 5-{[2'-(1H-tetrazol-5-yl)biphenyl-4-yl]methyl}-3-{5-{[2-(5-bromofuran-2-yl)-5-methyloxazol-4-yl]methoxyl}pyrimidin-2-yl}-6-butyl-2-methylpyrimidin-4(3H)-one, 5-{[2'-(1H-tetrazol-5-yl)biphenyl-4-yl]methyl}-6-butyl-3-{5-{[2-(furan-2-yl)-5-methyloxazol-4-yl]methoxy}pyrimidin-2-yl}-2-methylpyrimidin-4(3H)-one, 5-{[2'-(1H-tetrazol-5-yl)biphenyl-4-yl]methyl}6-butyl-2-methyl-3-{5-{[5-methyl-2-(naphthalen-2-yl)oxazol-4-yl]methoxyl pyrimidin-2-yl}-pyrimidin-4(3H)-one, 5-{[2'-(1H-tetrazol-5-yl)biphenyl-4-yl]methyl}-6-butyl-2-methyl-3-{5-[2-(5-methyl-2-phenyloxazol-4-yl)ethoxy]pyrimidin-2-yl}pyrimidin-4(3H)-one, 5-{[2'-(1H-tetrazol-5-yl)biphenyl-4-yl]methyl}-6-butyl-3-{5-[2-(5-ethylpyridin-2-yl)ethoxy]pyrimidin-2-yl}-2-methylpyrimidin-4(3H)-one, ethyl 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetate, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetic acid, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}acetamide, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylacetamide, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylacetamide, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetic acid, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-3-phenylpropionic acid, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetamide, ethyl 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanoate, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxyl}butanoic acid, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxyl}butanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-methylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-propylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-isopropylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylbutanamide, 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}pentanamide, 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylpentanamide, 5-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylpentanamide, N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}acetamide, N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}methane sulfonamide, N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}-1,1,1-trifluoromethane sulfonamide, 5-{[2'-(1H-tetrazol-5-yl)biphenyl-4-yl]-6-butyl-3-(2,6-dimethoxypyrimidin-4-yl)-2-methylpyrimidin-4(3H)-one, 5-{[2'-(1H-tetrazol-5-yl)biphenyl-4-yl]methyl}-6-buty-2-methyl-3-(pyrazin-2-yl)pyrimidin-4(3H)-one, 5-{[2'-(1H-tetrazol-5-yl)biphenyl-4-yl]methyl}-6-butyl-3-(5,6-dimethyl-1,2,4-triazin-3-yl)-2-methylpyrimidin-4(3H)-one, 5-{[2'-(1H-tetrazol-5-yl)biphenyl-4-yl]methyl}-6-butyl-2-methyl-3-(thiazol-2-yl)pyrimidin-4(3H)-one, 5-{[2'-(1H-tetrazol-5-yl)biphenyl-4-yl]methyl}-6-butyl-3-(isoxazol-3-yl)-2-methylpyrimidin-4(3H)-one, 5-{[2'-(1H-tetrazol-5-yl)biphenyl-4-yl]methyl}-6-butyl-2-methyl-3-(1-methyl-1H-pyrazol-5-yl)pyrimidin-4(3H)-one, 5-{[2'-(1H-tetrazol-5-yl)biphenyl-4-yl]methyl}-6-butyl-2-methyl-3-(1-methyl-1H-1,2,4-triazol-3-yl)pyrimidin-4(3H)-one, 5-{[2'-(1H-tetrazol-5-yl)biphenyl-4-yl]methyl}-6-butyl-2-methyl-3-(quinolin-2-yl)pyrimidin-4(3H)-one, 5-{[2'-(1H-tetrazol-5-yl)biphenyl-4-yl]methyl}-6-butyl-3-(isoquinolin-1-yl)-2-methylpyrimidin-4(3H)-one, 5-{[2'-(1H-tetrazol-5-yl)biphenyl-4-yl]methyl}-6-butyl-3-(isoquinolin-3-yl)-2-methylpyrimidin-4(3H)-one, 5-{[2'-(1H-tetrazol-5-yl)biphenyl-4-yl]methyl}-6-butyl-2-methyl-3-(1-methyl-1H-benzimidazol-2-yl)pyrimidin-4(3H)-one, and 5-{[2'-(1H-tetrazol-5-yl)biphenyl-4-yl]methyl}-3-(benzothiazol-2-yl)-6-butyl-2-methylpyrimidin-4(3H)-one.

5. The 3-heteroarylpyrimidin-4(3H)-one derivative described in claim 1 or salt thereof, or solvate thereof, in which the compound represented by the formula (I) is a compound that is selected from a group consisting of:

5-{[2'-(1H-tetrazol-5-yl)biphenyl-4-yl]methyl}-6-butyl-2-methyl-3-(5-methylpyridin-2-yl)pyrimidin-4(3H)-one, 5-{[2'-(1H-tetrazol-5-yl)biphenyl-4-yl]methyl}-6-butyl-3-(5-methoxypyridin-2-yl)-2-methylpyrimidin-4(3H)-one, 5-{[2'-(1H-tetrazol-5-yl)biphenyl-4-yl]methyl}-6-butyl-3-(3-fluoropyridin-2-yl)-2-methylpyrimidin-4(3H)-one, 5-{[2'-(1H-tetrazol-5-yl)biphenyl-4-yl]methyl}-6-butyl-3-(5-fluoropyridin-2-yl)-2-methylpyrimidin-4(3H)-one, 5-{[2'-(1H-tetrazol-5-yl)biphenyl-4-yl]methyl}-6-butyl-3-(3-chloropyridin-2-yl)-2-methylpyrimidin-4(3H)-one, 5-{[2'-(1H-tetrazol-5-yl)biphenyl-4-yl]methyl}-6-butyl-3-(5-chloropyridin-2-yl)-2-methylpyrimidin-4(3H)-one, 5-{[2'-(1H-tetrazol-5-yl)biphenyl-4-yl]methyl}-3-(6-bromopyridin-2-yl)-6-butyl-2-methylpyrimidin-4(3H)-one, 5-{[2'-(1H-tetrazol-5-yl)biphenyl-4-yl]methyl}-6-butyl-2-methyl-3-[4-(trifluoromethyl)pyridin-2-yl)pyrimidin-4(3H)-one, 5-{[2'-(1H-tetrazol-5-yl)biphenyl-4-yl]methyl}-6-butyl-2-methyl-3-[5-(trifluoromethyl)pyridin-2-yl)pyrimidin-4(3H)-one, 5-{[2'-(1H-tetrazol-5-yl)biphenyl-4-yl]methyl}-6-butyl-3-[3-chloro-5-(trifluoromethyl)pyridin-2-yl]-2-methylpyrimidin-4(3H)-one, 5-{[2'-(1H-tetrazol-5-yl)biphenyl-4-yl]methyl}-3-(5-bromopyrimidin-2-yl)-6-butyl-2-methylpyrimidin-4(3H)-one, 5-{[2'-(1H-tetrazol-5-yl)biphenyl-4-yl]methyl}-3-[5-(benzyloxy)pyrimidin-2-yl]-6-butyl-2-methylpyrimidin-4(3H)-one, 5-{[2'-(1H-tetrazol-5-yl)biphenyl-4-yl]methyl}-6-butyl-3-(5-ethoxypyrimidin-2-yl)-2-methylpyrimidin-4(3H)-one, 5-{[2'-(1H-tetrazol-5-yl)biphenyl-4-yl]methyl}-6-butyl-2-methyl-3-(5-propoxypyrimidin-2-yl)pyrimidin-4(3H)-one, 5-{[2'-(1H-tetrazol-5-yl)biphenyl-4-yl]methyl}-6-butyl-3-(5-isopropoxypyrimidin-2-yl)-2-methylpyrimidin-4(3H)-one, 5-{[2'-(1H-tetrazol-5-yl)biphenyl-4-yl]methyl}-3-(5-butoxypyrimidin-2-yl)-6-butyl-2-methylpyrimidin-4(3H)-one, 5-{[2'-(1H-tetrazol-5-yl)biphenyl-4-yl]methyl}-6-butyl-2-methyl-3-{5-[2-(methylthio)ethoxy]pyrimidin-2-yl}pyrimidin-4(3H)-one, 5-{[2'-(1H-tetrazol-5-yl)biphenyl-4-yl]methyl}-6-butyl-3-[5-(cyclohexyloxy)pyrimidin-2-yl]-2-methylpyrimidin-4(3H)-one, 5-{[2'-(1H-tetrazol-5-yl)biphenyl-4-yl]methyl}-6-butyl-3-{5-[2-(5-ethylpyridin-2-yl)ethoxy]pyrimidin-2-yl}-2-methylpyrimidin-4(3H)-one, 2-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-2-phenylacetic acid, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}butanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N-ethylbutanamide, 4-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}-N,N-diethylbutanamide, N-{3-{2-{5-{[2'-(1H-tetrazol-5-yl)biphenyl-4-yl]methyl}-4-butyl-2-methyl-6-oxopyrimidin-1(6H)-yl}pyrimidin-5-yl oxy}propyl}-1,1,1-trifluoromethanesulfonamide, 5-{[2'-(1H-tetrazol-5-yl)biphenyl-4-yl]-6-butyl-3-(2,6-dimethoxypyrimidin-4-yl)-2-methylpyrimidin-4(3H)-one, 5-{[2'-(1H-tetrazol-5-yl)biphenyl-4-yl]methyl}-6-butyl-2-methyl-3-(thiazol-2-yl)pyrimidin-4(3H)-one, 5-{[2'-(1H-tetrazol-5-yl)biphenyl-4-yl]methyl}-6-butyl-3-(isoxazol-3-yl)-2-methylpyrimidin-4(3H)-one, 5-{[2'-(1H-tetrazol-5-yl)biphenyl-4-yl]methyl}-6-butyl-2-methyl-3-(1-methyl-1H-pyrazol-5-yl)pyrimidin-4(3H)-one, 5-{[2'-(1H-tetrazol-5-yl)biphenyl-4-yl]methyl}-6-butyl-2-methyl-3-(quinolin-2-yl)pyrimidin-4(3H)-one, 5-{[2'-(1H-tetrazol-5-yl)biphenyl-4-yl]methyl}-6-butyl-3-(isoquinolin-1-yl)-2-methylpyrimidin-4(3H)-one, 5-{[2'-(1H-tetrazol-5-yl)biphenyl-4-yl]methyl}-6-butyl-3-(isoquinolin-3-yl)-2-methylpyrimidin-4(3H)-one, 5-{[2'-(1H-tetrazol-5-yl)biphenyl-4-yl]methyl}-6-butyl-2-methyl-3-(1-methyl-1H-benzimidazol-2-yl)pyrimidin-4(3H)-one, and 5-{[2'-(1H-tetrazol-5-yl)biphenyl-4-yl]methyl}-3-(benzothiazol-2-yl)-6-butyl-2-methylpyrimidin-4(3H)-one.

\* \* \* \* \*